(12) United States Patent
Smith et al.

(10) Patent No.: US 10,344,330 B2
(45) Date of Patent: Jul. 9, 2019

(54) GLATIRAMER ACETATE RESPONSE BIOMARKER MRNA POTENCY ASSAY

(71) Applicant: Mylan Inc., Canonsburg, PA (US)

(72) Inventors: Jeffrey P. Smith, Morgantown, WV (US); Peter E. Lipsky, Charlottesville, VA (US)

(73) Assignee: MYLAN INC., Canonsburg, PA (US)

( * ) Notice: Subject to any disclaimer, the term of this patent is extended or adjusted under 35 U.S.C. 154(b) by 174 days.

(21) Appl. No.: 14/206,681

(22) Filed: Mar. 12, 2014

(65) Prior Publication Data

US 2014/0272987 A1 Sep. 18, 2014

Related U.S. Application Data

(60) Provisional application No. 61/786,108, filed on Mar. 14, 2013.

(51) Int. Cl.
  *C12Q 1/6883* (2018.01)
  *C07H 21/04* (2006.01)

(52) U.S. Cl.
  CPC ..... *C12Q 1/6883* (2013.01); *C12Q 2600/136* (2013.01); *C12Q 2600/158* (2013.01)

(58) Field of Classification Search
  CPC ............ C12Q 1/6883; C12Q 2600/136; C12Q 2600/158
  See application file for complete search history.

(56) References Cited

U.S. PATENT DOCUMENTS

| | | | |
|---|---|---|---|
| 3,849,550 A | 11/1974 | Teitelbaum et al. | |
| 5,800,808 A | 9/1998 | Konfino et al. | |
| 5,958,707 A | 9/1999 | De et al. | |
| 5,981,589 A | 11/1999 | Konfino et al. | |
| 6,733,746 B2 | 5/2004 | Daley et al. | |
| 7,429,374 B2 | 9/2008 | Klinger | |
| 7,923,215 B2 | 4/2011 | Klinger | |
| 8,389,228 B2 | 3/2013 | Klinger | |
| 8,481,315 B2 | 7/2013 | Fong et al. | |
| 8,709,433 B2 | 4/2014 | Kasper et al. | |
| 8,759,302 B2 | 6/2014 | Dhib-Jalbut | |
| 2003/0170729 A1 | 9/2003 | Klinger | |
| 2009/0005419 A1 | 1/2009 | Auer et al. | |
| 2011/0053203 A1 | 3/2011 | D'Alessandro et al. | |
| 2011/0189706 A1 | 8/2011 | Klinger | |
| 2011/0295782 A1 | 12/2011 | Stojadinovic et al. | |
| 2013/0210054 A1 | 8/2013 | D'Alessandro | |
| 2014/0107208 A1 | 4/2014 | Comabella et al. | |
| 2014/0193827 A1 | 7/2014 | Schwartz et al. | |
| 2015/0141284 A1 | 5/2015 | Smith et al. | |

FOREIGN PATENT DOCUMENTS

| | | |
|---|---|---|
| AR | 098194 A1 | 5/2016 |
| CN | 1308683 C | 4/2007 |
| CN | 105377308 A | 3/2016 |
| EP | 1261361 A1 | 12/2002 |
| EP | 2971173 A2 | 1/2016 |
| EP | 3060684 A2 | 8/2016 |
| JP | 2003529335 A | 10/2003 |
| JP | 2005511060 A | 4/2005 |
| JP | 2016512432 A | 4/2016 |
| TW | 201447297 A | 12/2014 |
| TW | 201606305 A | 2/2016 |
| WO | WO-9914360 A1 | 3/1999 |
| WO | WO-0129251 A2 | 4/2001 |
| WO | WO-0160392 A1 | 8/2001 |
| WO | WO-03048735 A2 | 6/2003 |
| WO | WO-2003048735 | 6/2003 |
| WO | WO-2006029411 A2 | 3/2006 |
| WO | WO 2008/157697 A2 | 12/2008 |
| WO | WO 2013/120106 A2 | 8/2013 |
| WO | WO 2013/139728 A1 | 9/2013 |
| WO | WO 2014/107533 A2 | 7/2014 |
| WO | WO-2014/159685 | 10/2014 |
| WO | WO-2014159685 A2 | 10/2014 |
| WO | WO-2014159685 A3 | 12/2014 |
| WO | WO 2015/061610 | 4/2015 |
| WO | WO-2015061610 | 4/2015 |

OTHER PUBLICATIONS

Schrock, R.D., BioProcessing J., vol. 11, pp. 4-12 (2012).*
D'Alessandro, J.S. et al., PLoS One, vol. 10, e0140299, pp. 1-19 (2015).*
Vandesompele, J. et al., Genome Biol., vol. 3 (7), pp. 1-12 (2002).*
Alrbershardt, T.C. et al., J. Immunol. Meth., vol. 384, pp. 196-199 (2012).*
Reva Pharmaceuticals, Citizen Petition Requesting That FDA Refrain From Approving Any Abbreviated New Drug Application Referencing Copaxone® (glatiramer acetate injection) Until Certain Conditions Are Met, pp. 1-35; downloaded from www.fdanews.com/ext/resources/files/archives/0/06/06-20-12-briefs.pdf (Year: 2012).*
Bakshi, et al., "Gene expression analysis reveals functional pathways of glatiramer acetate activation," Expert Opin Ther Targets. Apr. 2013;17(4):351-362.
Biolegend.com web reference, "Mouse alloantigens." URL: http://www.biolegend.com/media_assets/support_resource/BioLegend_Mouse_Alloantigens.pdf ; file downloaded Mar. 5, 2014.
Bustin, et al., 2005, "Quantitative real-time RT-PCR—a perspective," Journal of Molecular Endocrinology, 34:597-601.
Duda et al, "Human and murine CD4 T cell reactivity to a complex antigen: recognition of the synthetic random polypeptide glatiramer acetate." J Immunol. Dec. 15, 2000;165(12):7300-7307.
Eppig JT and Strivens M, 1999, "Finding a mouse: the International Mouse Strain Resource (IMSR)." Trends in Genetics 15: 81-82.

(Continued)

Primary Examiner — Teresa E Strzelecka
(74) Attorney, Agent, or Firm — Wilson Sonsini Goodrich & Rosati

(57) ABSTRACT

The invention describes assays for determining the potency of a test lot of glatiramer acetate (GA) by quantitating and comparing the levels of mRNA response biomarkers produced in mouse T-cells in response to stimulation with the test lot or a reference standard lot of GA, wherein the T-cells are obtained from mice immunized with the test lot or the reference standard lot of GA. Methods for identifying mRNA response biomarkers useful in the assays of the invention also are described.

50 Claims, 13 Drawing Sheets

(56) References Cited

OTHER PUBLICATIONS

Friberg et al. "In vitro cytokine production by normal human peripheral blood mononuclear cells as a measure of immunocompetence or the state of activation." Clin Diagn Lab Immunol. May 1994;1(3):261-268.

Kersh et al., "Structural basis for T cell recognition of altered peptide ligands: a single T cell receptor can productively recognize a large continuum of related ligands." J Exp Med. Oct. 1, 1996:184(4):1259-1268.

Krensky, et al., 1982, "Long-term human cytolytic T-cell lines allospecific for HLA-DR6 antigen are OKT4+." Proc Natl Acad Sci. Apr. 1982;79(7):2365-2369.

Li et al., "RNA-Seq gene expression estimation with read mapping uncertainty." Bioinformatics. Feb. 15, 2010:26(4):493-500.

Nagalakshmi, et al., Jan. 2010, "RNA-Seq: A Method for Comprehensive Transcriptome Analysis," Current Protocols in Molecular Biology, Wiley Interscience, Unit 4.11, Supplement 89, Copyright 2010 John Wiley & Sons, Inc.

Overbergh, et al., 1999, "Quantification of murine cytokine mRNAs using real time quantitative reverse transcriptase PCR," Cytokine 11(4): 305-312.

Stern et al., "Peptide 15-mers of defined sequence that substitute for random amino acid copolymers in amelioration of experimental autoimmune encephalomyelitis." Proc Natl Acad Sci U S A. Feb. 1, 2005:102(5):1620-1625.

Towfic et al., "Comparing the biological impact of glatiramer acetate with the biological impact of a generic." PLoS One. Jan. 8, 2014;9(1):e83757.

Ucker et al., "Activation-driven T cell death. II. Quantitative differences alone distinguish stimuli triggering nontransformed T cell proliferation or death." J Immunol. Sep. 1, 1992:149(5):1583-1592.

Udvardi et al., "Eleven golden rules of quantitative RT-PCR." Plant Cell. Jul. 2008;20(7)1736-1737.

VanGuilder, et al., 2008, "Twenty-five years of quantitative PCR for gene expression analysis," Biotechniques 44: 619-626.

Wong and Medrano, 2005, Real-Time PCR for mRNA Quantitation, Biotechniques 39: 75-85.

Wucherpfennig et al., 1994, "Structural requirements for binding of an immunodominant myelin basic protein peptide to DR2 isotypes and for its recognition by human T cell clones." J Exp Med. Jan. 1, 1994;179(1):279-290.

Henri et al. The Dendritic Cell Populations of Mouse Lymph Nodes. The Journal of Immunology. 167:741-748 (2001).

Neuhaus et al. Multiple Sclerosis: Comparison of Copolymer-1-Reactive T Cell Lines from Treated and Untreated Subjects Reveals Cytokine Shift from T Helper 1 to Helper 2 Cells. PNAS. 97(13):7452-7457 (2000).

PCT/US14/62039 International Search Report and Written Opinion dated Apr. 20, 2015.

Seo et al. Activation of murine epidermal V gamma 5/V delta 1-TCR(+) T cell lines by Glu-Tyr polypeptides. Jour of Invest Derm. 116:880-885 (2001).

Anderson, et al. Demonstration of Equivalence between a Generic (M356) and Brand Comaxone (glatiramer acetate injection) (Apr. 20, 2015).

Anderson, et al. Demonstration of Equivalence between a Generic (M356) and Brand Copaxone (glatiramer acetate injection). Momenta Pharmaceuticals Poster P1.145 (Apr. 20, 2015).

D'Alessandro et al. Comparative Gene Expression Profiling between a Generic (Glatopa) and Brand Copaxone (glatiramer acetate injection). Momenta Pharmaceuticals (Apr. 20, 2015).

D'Alessandro et al. Comparative Gene Expression Profiling Between a Generic (Glatopa) and Brand Copaxone (glatiramer acetate injection). Momenta Pharmaceuticals Poster P1.144 (Apr. 20, 2015).

Kolitz et al. Gene expression studies of a human monocyte cell line identify dissimilarities between differently manufactured glatiramoids. Scientific Reports 5:1-14 (May 22, 2015).

Choi, et al., Nov. 1989, "Interaction of *Staphylococcus aureus* toxin 'superantigens' with human T cells," Proc Natl Acad Sci USA 86(22):8941-8945.

Good, et al. "Human T clones reactive to the sexual stages of Plasmodium falciparum malaria. High frequency of gamete-reactive T cells in peripheral blood from nonexposed donors." J Immunol. Jan. 1, 1987;138(1):306-311.

Gorski, et al., May 15, 1994, "Circulating T cell repertoire complexity in normal individuals and bone marrow recipients analyzed by CDR3 size spectratyping. Correlation with immune status," J Immunol. 152(10):5109-5119.

Imitola, et al, "Cytokines in multiple sclerosis: from bench to bedside." Pharmacol Ther. May 2005;106(2):163-177.

Lee, et al, "A novel strategy for rapid and efficient isolation of human tumor-specific CD4(+) and CD8(+) T-cell clones." J Immunol Methods. Feb. 29, 2008;331(1-2):13-26.

Mariotti, et al., "Generation of human T cell clones." Methods Mol Biol. 2009;514:65-93.

Miller, et al., "Treatment of multiple sclerosis with copolymer-1 (Copaxone): implicating mechanisms of Th1 to Th2/Th3 immune-deviation." J Neuroimmunol. Dec. 1, 1998;92(1-2):113-121.

Nie, et al., "Correlation between mRNA and protein abundance in Desulfovibrio vulgaris: a multiple regression to identify sources of variations." Biochem Biophys Res Commun. Jan. 13, 2006;339(2):603-610.

Oftung F., et al., 1994, "Mapping of multiple HLA class II restricted T-cell epitopes of the mycobacterial 70-kilodalton heat shock protein," Infect. Immun. 62:5411-5418.

Ota, et al. (1990).

PCT/US14/24748 International Search Report and Written Opinion dated Oct. 24, 2014.

Quah, et al., 2007, "Monitoring lymphocyte proliferation in vitro and in vivo with the intracellular fluorescent dye carboxyfluorescein diacetate succinimidyl ester," Nature Protocols 2(9):2049-2056.

Wiesemann, et al., "Glatiramer acetate (GA) induces IL-13/IL-5 secretion in naive T cells." J Neuroimmunol. Sep. 3, 2001;119(1):137-144.

Yang, J. "Peripheral immune response in chronic relapsing experimental autoimmune encephalomyelitis in SJL mice," Academic Dissertation, Nov. 14, 2003; available at URL: <http://ethesis.helsinki.fi/julkaisut/laa/haart/vk/yang/peripher.pdf>; accessed Nov. 6, 2014.

PCT/US2014/024748 International Preliminary Report on Patentability dated Sep. 24, 2015.

U.S. Appl. No. 14/522,521 Office Action dated Mar. 29, 2016.

U.S. Appl. No. 14/522,521 Restriction Requirement dated Oct. 8, 2015.

Achiron et al., Molecular profiling of glatiramer acetate early treatment effects in multiple sclerosis. Disease Markers, 27:63-73, 2009.

European Patent Application No. 14773936.1 Extended European Search Report dated Oct. 26, 2016.

PCT/US2014/062039 International Preliminary Report on Patentability dated May 6, 2016.

Yong. Differential mechanisms of action of interferon-beta and glatiramer acetate in MS. Neurology, 59:802-808, 2002.

Chinese Patent Application No. 2014800284162 First Office Action dated Jun. 26, 2017.

Dabbert et al., Glatiramer acetate (Copolymer-1)-specific, human T cell lines; cytokine profile and suppression of T cell lines reactive against myelin basic protein. Neuroscience Letters, 289:205-208, 2000.

Duda et al., Glatiramer acetate (Copaxone) induxces degenerate Th2-polarized immune responses in patients with multiple sclerosis. J.Clinical Investigation, 105:967-976, 2000.

European Patent Application No. 14856438.8 extended European search report dated May 10, 2017.

Henri et al., The Dendritic cell populations of mouse lymph nodes. J.Immunology, 167:741-748, 2001.

Johnson. Glatiramer acetate and the glatiramoid class of immunomodulator drugs in multiple sclerosis: an update. Expert Opinion on Drug Metabolism & Toxicology. 6:5, 643-660, 2010.

(56) References Cited

OTHER PUBLICATIONS

Neuhaus et al., Multiple sclerosis: Comparison of copolymer-1-reactive T cell lines from treated and untreated subjects reveals cytokine shift from T helper 1 to T helper 2 cells. PNAS, 97(13):7452-7457, 2000.

Nicholas et al., Multiple sclerosis. Neurology Clinical Practice, 3(5):404-412, 2013.

Qin et al., Characterization of T cell lines derived from glatiramer-acetate-treated multiple sclerosis patients. Journal of Neuroimmunology, 108:201-206, 2000.

Racke et al., The mechanism of action of glatiramer acetate treatment in multiple sclerosis. Neurology, 74(Suppl 1):S25-S30, 2010.

Seo et al., Activation of murine epidermal Vγ5/Vδ1-TCR+ T cell lines by Glu-Tyr polypeptides. Journal of Invest. Dermatology, 116:880-885, 2001.

U.S. Appl. No. 14/522,521 Office Action dated May 4, 2017.

Ziemssen et al., Glatiramer acetate-specific T-helper 1- and 2-type cell lines produce BDNF: implications for multiple sclerosis therapy. Brain, 125:2381-2391, 2002.

European Patent Application No. 14773936.1 Communication dated Dec. 21, 2017.

Johnson K.P., Copolymer 1 reduces relapse rate and improves disability in relapsing-remitting multiple sclerosis: Results of a phase III multicenter, double-blind, placebo-controlled trial. Neurology, 45:1268-1276, 1995.

Taiwan Patent Application No. 103109072 Official Letter with a Search Report dated Oct. 23, 2017.

Chinese Patent Application No. 2014800284162 Second Office Action dated Mar. 19, 2018.

Co-pending U.S. Appl. No. 15/921,487, filed Mar. 14, 2018.

Japanese Patent Application No. 2016-501627 Office Action dated Feb. 27, 2018.

Miller et al. Treatment of multiple sclerosis with copolymer-1 (Copaxone): implicating mechanisms of Th1 to Th2/Th3 immune-deviation. J Neuroimmunol 92:113-121, 1998.

\* cited by examiner

A.

B.

A.

B.

A.

B.

A.

B.

A.

B.

A.

B.

A.

B.

A.

B.

A.

B.

A.

B.

GLATIRAMER ACETATE RESPONSE BIOMARKER MRNA POTENCY ASSAY

This application claims the benefit under 35 U.S.C. 119(e) of U.S. Prov. Pat. App. No. 61/786,108, which was filed on Mar. 14, 2013, and is incorporated herein by reference in its entirety.

BACKGROUND OF THE INVENTION

Glatiramer acetate is a synthetic peptide drug approved for treating multiple sclerosis. It consists of the acetate salts of synthetic polypeptides containing the amino acids L-glutamic acid, L-alanine, L-tyrosine, and L-lysine. Currently sold as Copaxone®, glatiramer acetate injection is indicated for the reduction of the frequency of relapses in patients with Relapsing-Remitting Multiple Sclerosis (RRMS), including patients who have experienced a first clinical episode and have MRI features consistent with Multiple Sclerosis.

Glatiramer acetate is thought to act in multiple sclerosis by modifying immune processes responsible for the pathogenesis of the disease. In particular, it is believed that the mechanism of action of Copaxone® in Multiple Sclerosis is at least in part mediated by immunomodulation of T-cell activity.

During the manufacture of glatiramer acetate, fast, sensitive, reliable and cost-effective potency assays that take into account the drug's mechanism of action are needed for demonstrating consistent potency between drug lots for pharmaceutical use.

SUMMARY OF THE INVENTION

The present invention relates to a new potency assay for glatiramer acetate (GA), wherein the potency of a test lot of GA is determined by quantitating and comparing at least one response biomarker mRNA that is expressed by GA-specific T-cells in response to stimulation with the test lot of GA and a reference standard lot of GA. The GA-specific T-cells are obtained from mice immunized with the test lot or the reference standard lot of GA. Methods for identifying mRNA response biomarkers for use in the assay also are described.

In embodiments, the present invention relates to a process for determining the potency of a test lot of GA, the process comprising: immunizing a test animal with a defined amount of a GA reference standard lot; culturing lymph node cells removed from the immunized test animal; incubating at least one sample containing a predetermined number of the cultured lymph node cells in the presence of a predetermined amount of the GA reference standard lot, and at least one sample containing a predetermined number of the cultured lymph node cells in the presence of a predetermined amount of a test lot of GA; measuring the amount of at least one GA response biomarker mRNA in the lymph node cells incubated with the predetermined amount of the GA reference standard lot, and the amount of the least one GA response biomarker mRNA in the lymph node cells incubated with the predetermined amount of the test lot of GA, and; comparing the amount of the least one GA response biomarker mRNA measured in the lymph node cells incubated with the predetermined amount of the test lot of GA with the amount of the least one GA response biomarker mRNA measured in the lymph node cells incubated with the predetermined amount of the GA reference standard lot; thereby determining the relative potency of the test lot of GA.

In related embodiments, the test animal is a mouse. In certain embodiments, the mouse is a female SJL/J, BALB/cByJ, CD-1, C57BL/10J, or (SJL/J×BALB/c) F1 mouse. In embodiments, the at least one GA response biomarker mRNA is transcribed from a gene encoding a cytokine or a cytokine receptor. In related embodiments, the at least one GA response biomarker mRNA is transcribed from a gene encoding a cytokine, wherein the cytokine is IL-2, IL-4, IL-5, IL-10, IFN-γ, TNF-α, IL-1b, IL-13, IL-17, or any combination thereof. In certain embodiments, the at least one glatiramer acetate response biomarker mRNA is transcribed from a gene encoding IL-2, IL-4, IL-5, IL-10, IL-13, IL-17, IFN-γ, or any combination thereof. In other embodiments, the at least one glatiramer acetate response biomarker mRNA is transcribed from a gene encoding a cytokine receptor, wherein the cytokine receptor is CD69, CD25, or both. In embodiments, the at least one biomarker mRNA is measured in the culture of lymph node cells 9-11 days after immunization of the mouse with the GA reference standard lot.

In embodiments, the process of the invention further comprises determining whether the test lot of GA has a desired relative potency. In these embodiments, the desired relative potency is, e.g., at least about 90% to about 125% of the potency of the GA reference standard lot or the desired relative potency is at least about 95% to about 125% of the potency of the GA reference standard lot.

In embodiments of the invention, the at least one response biomarker mRNA is measured by Real-Time PCR. In related embodiments, the response biomarker mRNA is measured at about 4 to about 6 hours after the incubation is initiated. In certain embodiments, a protein synthesis inhibitor, e.g., cycloheximide, is added to the incubation of the lymph node cells with the GA reference standard lot, and to the incubation of the lymph node cells with the test lot of GA.

In embodiments of the process of the invention the reference standard lot is Copaxone.

The invention further relates to a process for determining the potency of a reference standard lot of GA, the process comprising: immunizing a test animal with a defined amount of a GA test lot; culturing lymph node cells removed from the immunized test animal; incubating at least one sample containing a predetermined number of the cultured lymph node cells in the presence of a predetermined amount of the GA test lot, and at least one sample containing a predetermined number of the cultured lymph node cells in the presence of a predetermined amount of a reference standard lot of GA; measuring the amount of at least one GA response biomarker mRNA in the lymph node cells incubated with the predetermined amount of the GA test lot, and the amount of the least one GA response biomarker mRNA in the lymph node cells incubated with the predetermined amount of the reference standard lot of GA, and; comparing the amount of the least one GA response biomarker mRNA measured in the lymph node cells incubated with the predetermined amount of the reference standard lot of GA with the amount of the least one GA response biomarker mRNA measured in the lymph node cells incubated with the predetermined amount of the GA test lot; thereby determining the relative potency of the reference standard lot of GA.

In related embodiments, the test animal is a mouse. In certain embodiments, the mouse is a female SJL/J, BALB/cByJ, CD-1, C57BL/10J, or (SJL/J×BALB/c) F1 mouse. In embodiments, the at least one GA response biomarker mRNA is transcribed from a gene encoding a cytokine or a cytokine receptor. In related embodiments, the at least one GA response biomarker mRNA is transcribed from a gene encoding a cytokine, wherein the cytokine is IL-2, IL-4, IL-5, IL-10, IFN-γ, TNF-αc, IL-1b, IL-13, IL-17, or any combination thereof. In certain embodiments, the at least one GA response biomarker mRNA is transcribed from a gene encoding IL-2, IL-4, IL-5, IL-10, IL-13, IL-17, IFN-γ, or any combination thereof. In other embodiments, the at least one GA response biomarker mRNA is transcribed from a gene encoding a cytokine receptor, wherein the cytokine receptor is CD69, CD25, or both. In embodiments, the at least one biomarker mRNA is measured in the culture of lymph node cells 9-11 days after immunization of the mouse with the GA reference standard lot.

In embodiments, the process of the invention further comprises determining whether the test lot of GA has a desired relative potency. In these embodiments, the desired relative potency is, e.g., at least about 90% to about 125% of the potency of the GA reference standard lot or the desired relative potency is at least about 95% to about 125% of the potency of the GA reference standard lot.

In embodiments of the invention, the at least one response biomarker mRNA is measured by Real-Time PCR. In related embodiments, the response biomarker mRNA is measured at about 4 to about 6 hours after the incubation is initiated. In certain embodiments, a protein synthesis inhibitor, e.g., cycloheximide, is added to the incubation of the lymph node cells with the GA reference standard lot, and to the incubation of the lymph node cells with the test lot of GA.

In embodiments of the process of the invention the reference standard lot is Copaxone.

Also provided is a process for preparing a pharmaceutical composition containing GA, wherein during the process a test lot of GA is tested to determine whether it has a desired potency relative to the potency of the GA reference standard lot, the process comprising determining the potency of the test lot of GA and comparing it to the potency of the reference standard lot, wherein the potencies of the test lot of GA and the reference standard lot are determined by measuring the amount of at least one GA response biomarker mRNA produced in a cell of a culture of lymph node cells removed from a test mammal that has been immunized with a defined amount of a GA reference standard lot, wherein at least one sample containing a predetermined number of the cultured lymph node cells is incubated in the presence of a predetermined amount of the GA reference standard lot, and wherein at least one sample containing a substantially identical predetermined number of the cultured lymph node cells is incubated in the presence of the same predetermined amount of the test lot of GA, and wherein the test lot of GA is admixed into the pharmaceutical composition only if the test lot of GA is determined to have the desired potency relative to the potency of the reference standard lot.

In related embodiments, the test animal is a mouse. In certain embodiments, the mouse is a female SJL/J, BALB/cByJ, CD-1, C57BL/10J, or (SJL/J×BALB/c) F1 mouse. In embodiments, the at least one GA response biomarker mRNA is transcribed from a gene encoding a cytokine or a cytokine receptor. In related embodiments, the at least one GA response biomarker mRNA is transcribed from a gene encoding a cytokine, wherein the cytokine is IL-2, IL-4, IL-5, IL-10, IFN-γ, TNF-α, IL-1b, IL-13, IL-17, or any combination thereof. In certain embodiments, the at least one GA response biomarker mRNA is transcribed from a gene encoding IL-2, IL-4, IL-5, IL-10, IL-13, IL-17, IFN-γ, or any combination thereof. In other embodiments, the at least one GA response biomarker mRNA is transcribed from a gene encoding a cytokine receptor, wherein the cytokine receptor is CD69, CD25, or both. In embodiments, the at least one biomarker mRNA is measured in the culture of lymph node cells 9-11 days after immunization of the mouse with the GA reference standard lot.

In embodiments, the process of the invention further comprises determining whether the test lot of GA has a desired relative potency. In these embodiments, the desired relative potency is, e.g., at least about 90% to about 125% of the potency of the glatiramer acetate reference standard lot or the desired relative potency is at least about 95% to about 125% of the potency of the glatiramer acetate reference standard lot.

In embodiments of the invention, the at least one response biomarker mRNA is measured by Real-Time PCR. In related embodiments, the response biomarker mRNA is measured at about 4 to about 6 hours after the incubation is initiated. In certain embodiments, a protein synthesis inhibitor, e.g., cycloheximide, is added to the incubation of the lymph node cells with the GA reference standard lot, and to the incubation of the lymph node cells with the test lot of GA.

In embodiments of the process of the invention the reference standard lot is Copaxone.

The invention further relates to a method for identifying a GA response biomarker mRNA for use in a GA T-cell potency assay, the method comprising: immunizing a test animal with a defined amount of GA; immunizing a test animal with a control antigen; culturing lymph node cells removed from the GA immunized test animal and separately culturing lymph node cells removed from the control antigen immunized test animal; incubating at least one sample containing a predetermined number of the cultured lymph node cells from the GA immunized test animal in the presence of a predetermined amount of the GA, and at least one sample containing a predetermined number of the cultured lymph node cells removed from the control antigen immunized test animal in the presence of a predetermined amount of a test lot of GA; measuring the amount of a candidate response biomarker mRNA in the incubated lymph node cells from the GA immunized test animal, and measuring the amount of the candidate response biomarker mRNA in the incubated lymph node cells from the control antigen immunized test animal, and; comparing the amount of the candidate response biomarker mRNA in the incubated lymph node cells from the GA immunized test animal with the amount of the candidate response biomarker mRNA in the incubated lymph node cells from the control antigen immunized test animal; wherein the candidate response biomarker mRNA is identified as a response biomarker mRNA if the amount of the candidate response biomarker mRNA measured in the incubated lymph node cells from the GA immunized test animal is significantly higher than the amount of the candidate response biomarker mRNA in the incubated lymph node cells from the control antigen immunized test animal.

In certain embodiments, the invention relates to a process for determining the potency and cross-potency of a test lot of GA, the process comprising: immunizing a first test animal with a defined amount of a GA reference standard lot; immunizing a second test animal with a defined amount of a GA test lot; culturing lymph node cells removed from the immunized first test animal, and separately culturing lymph node cells removed from the immunized second test animal; incubating at least one sample containing a predetermined number of the cultured lymph node cells from the immunized first test animal in the presence of a predetermined amount of the GA reference standard lot, and at least one sample containing a predetermined number of the cultured lymph node cells from the immunized first test animal in the presence of a predetermined amount of a test lot of GA; incubating at least one sample containing a predetermined number of the cultured lymph node cells from the immunized second test animal in the presence of a predetermined amount of the GA reference standard lot, and at least one sample containing a predetermined number of the cultured lymph node cells from the immunized second test animal in the presence of a predetermined amount of a test lot of GA; measuring the amount of at least one GA response biomarker mRNA in the lymph node cells from the immunized first test animal incubated with the predetermined amount of the GA reference standard lot, and the amount of the least one GA response biomarker mRNA in the lymph node cells from the immunized first test animal incubated with the predetermined amount of the test lot of GA; measuring the amount of at the least one GA response biomarker mRNA in the lymph node cells from the immunized second test animal incubated with the predetermined amount of the GA reference standard lot, and the amount of the least one GA response biomarker mRNA in the lymph node cells from the immunized second test animal incubated with the predetermined amount of the test lot of GA; comparing the amount of the least one GA response biomarker mRNA measured in the lymph node cells from the immunized first test animal incubated with the predetermined amount of the test lot of GA with the amount of the least one GA response biomarker mRNA measured in the lymph node cells from the immunized first test animal incubated with the predetermined amount of the GA reference standard lot, thereby determining the relative potency of the test lot of GA; comparing the amount of the least one GA response biomarker mRNA measured in the lymph node cells from the immunized second test animal incubated with the predetermined amount of the test lot of GA with the amount of the least one GA response biomarker mRNA measured in the lymph node cells from the immunized second test animal incubated with the predetermined amount of the GA reference standard lot; thereby determining the relative potency of the reference standard lot of GA; comparing the amount of the least one GA response biomarker mRNA measured in the lymph node cells from the immunized first test animal incubated with the predetermined amount of the test lot of GA with the amount of the least one GA response biomarker mRNA measured in the lymph node cells from the immunized second test animal incubated with the predetermined amount of the GA test lot; thereby determining the cross-potency of the test lot of GA.

In these embodiments, the first test animal and the second test animal can be selected from: mice of the same mouse strain: HLA-matched mice; littermates, and; twins. In embodiments, the first test animal and the second test animal are of the same mouse strain, and wherein the mouse strain is selected from: female CSJLF1/JRj, female SJL/J, female BALB/cByJ, female CD-1, female C57BL/10J, and female (SJL/J×BALB/c) F1. In embodiments, the at least one GA response biomarker mRNA is transcribed from a gene encoding a cytokine or a cytokine receptor. In related embodiments, the at least one GA response biomarker mRNA is transcribed from a gene encoding a cytokine, wherein the cytokine is IL-2, IL-4, IL-5, IL-10, IFN-γ, TNF-α, IL-1b, IL-13, IL-17, or any combination thereof. In certain embodiments, the at least one GA response biomarker mRNA is transcribed from a gene encoding IL-2, IL-4, IL-5, IL-10, IL-13, IL-17, IFN-γ, or any combination thereof. In other embodiments, the at least one GA response biomarker mRNA is transcribed from a gene encoding a cytokine receptor, wherein the cytokine receptor is CD69, CD25, or both. In embodiments, the at least one biomarker mRNA is measured in the culture of lymph node cells 9-11 days after immunization of the mouse with the GA reference standard lot.

In embodiments, the process of the invention further comprises determining whether the test lot of GA has a desired relative potency, a desired relative cross-potency, or both. In these embodiments, the desired relative potency or desired relative cross-potency is, e.g., at least about 90% to about 125% of the potency of the GA reference standard lot or the desired relative potency or desired relative cross-potency is at least about 95% to about 125% of the potency of the GA reference standard lot.

In embodiments of the invention, the at least one response biomarker mRNA is measured by Real-Time PCR. In related embodiments, the response biomarker mRNA is measured at about 4 to about 6 hours after the incubation is initiated. In certain embodiments, a protein synthesis inhibitor, e.g., cycloheximide, is added to the incubation of the lymph node cells with the GA reference standard lot, and to the incubation of the lymph node cells with the test lot of GA.

In embodiments of the process of the invention the reference standard lot is Copaxone.

The invention also provides a process for determining the potency of a second lot of GA, the process comprising: immunizing a test animal with a defined amount of a first GA lot; culturing lymph node cells removed from the immunized test animal; incubating at least one sample containing a predetermined number of the cultured lymph node cells in the presence of a predetermined amount of the first GA lot, and at least one sample containing a predetermined number of the cultured lymph node cells in the presence of a predetermined amount of a second lot of GA; measuring the amount of at least one GA response biomarker mRNA in the lymph node cells incubated with the predetermined amount of the first GA lot, and the amount of the least one GA response biomarker mRNA in the lymph node cells incubated with the predetermined amount of the second lot of GA, and; comparing the amount of the least one GA response biomarker mRNA measured in the lymph node cells incubated with the predetermined amount of the second lot of GA with the amount of the least one GA response biomarker mRNA measured in the lymph node cells incubated with the predetermined amount of the first GA lot; thereby determining the relative potency of the second lot of GA. In these embodiments, the first GA lot can be Copaxone, a reference standard lot of GA, or a test lot of GA. In these embodiments, the second GA lot can be Copaxone, a reference standard lot of GA, or a test lot of GA.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Glatiramer Acetate (GA)

Figure 1:
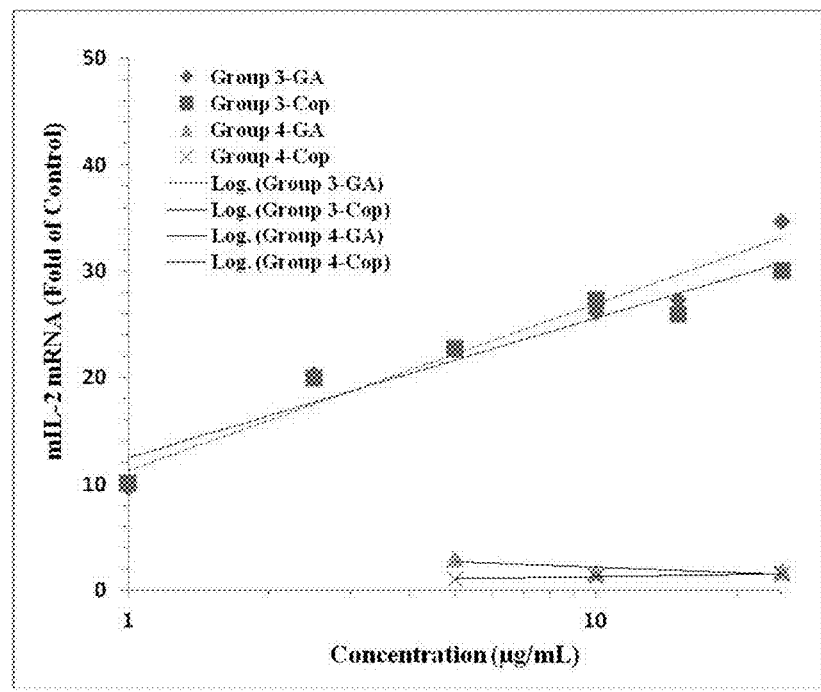
FIG. 1. mIL-2 mRNA Expressed in Primary LN Cells in Response to Different Concentrations of GA. This figure shows a graph of the data presented herein in Table 6. LN cells from GA-immunized mice were stimulated ex vivo with GA or Copaxone at different concentrations and mIL-2 mRNA was measured. IL-2 mRNA levels are expressed as fold increase relative to a DCCM1 (culture medium) control. A. Six GA concentrations (1, 2.5, 5, 10, 15 and 25 µg/mL) were used for stimulation of the LN cells. B. Five GA concentrations (1, 2.5, 5, 10 and 15 µg/mL) were used for stimulation of the LN cells. For both A and B, diamonds indicate expression of mIL-2 mRNA in Group 3 cells (from mice immunized with GA) stimulated with GMA (glatiramer acetate, Mylan Pharmaceuticals, Inc.) Squares indicate expression in Group 3 cells stimulated with Copaxone (Teva Pharmaceuticals USA, Inc.). Triangles indicate expression in Group 4 cells (from mice immunized with mannitol) stimulated with GMA. X's indicate Group 4 cells stimulated with Copaxone. The data are plotted on semi log. Additionally, a logarithmic trendline/regression was added to the plot. All $r^2$ values were >0.90 or 90%.
Figure 1:
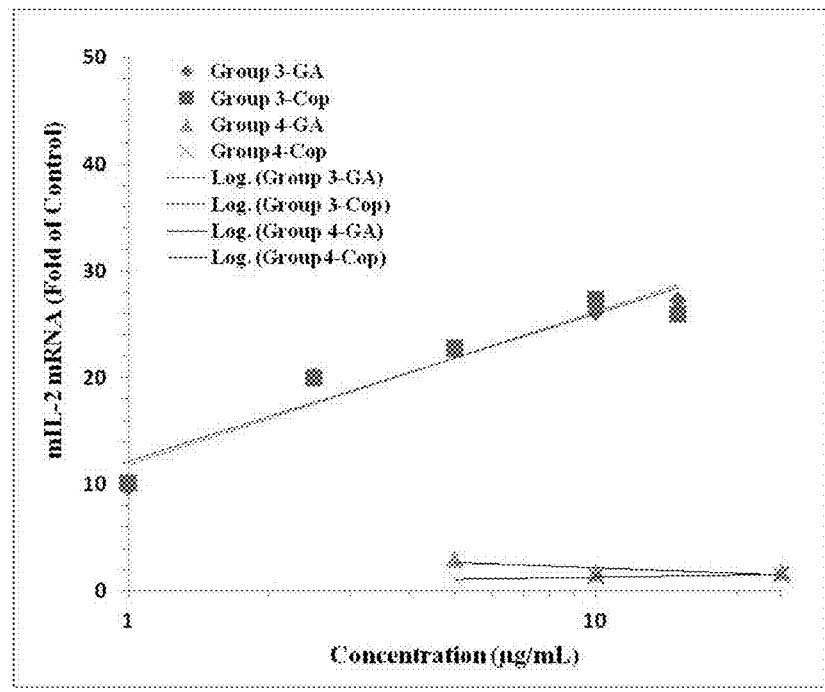

GA consists of the acetate salts of synthetic polypeptides that contain four naturally occurring amino acids: L-glutamic acid, L-alanine, L-tyrosine, and L-lysine with an average molar fraction of 0.141, 0.427, 0.095, and 0.338, respectively. The average molecular weight of GA is 5,000-9,000 daltons. Chemically, GA is designated L-glutamic acid polymer with L-alanine, L-lysine and L-tyrosine, acetate (salt).

The empirical formula of GA is $(C_5H_9NO_4 \cdot C_3H_7NO_2 \cdot C_6H_{14}N_2O_2 \cdot C_9H_{11}NO_3)_x \cdot xC_2H_4O_2$ (CAS-147245-92-9, Physician's Desk Reference).

As used herein, "GA" refers generally to GA, including, e.g., "GMA," GA produced by Mylan Pharmaceuticals, Inc., and "Cop," or "Copaxone," GA produced by Teva Pharmaceuticals USA, Inc., unless specifically stated.

Potency Assays for Testing Glatiramer Acetate Production Lots

The present invention relates to potency assays useful for demonstrating consistent potency among drug lots in the manufacture of GA acceptable for pharmaceutical use. It is typical for drug approval agencies to require potency testing of drugs during the approval process, and to require the development of potency assays that can be used to determine lot to lot consistency post-approval. Such assays are useful not only to ensure lot consistency during routine manufacturing, but also to evaluate drug lots following changes in manufacturing process.

Potency is a product-specific measurement, and assays must be evaluated for each product individually. The mechanism of action of GA in multiple sclerosis (MS) is believed to be in part mediated by immunomodulation of T-cell activity. The immunologic response of T-cells to GA is therefore a specific and sensitive measure of epitopes present in a GA solution. Because of the unique ability of T-cells to distinguish between different but very similar peptides present in a solution, analyzing the cytokine secretion profile and immunological activity of GA-specific T-cells in culture can distinguish immunologically relevant differences between lots of GA. In this regard, immunologic identity as shown by T-cell responses in animals primed with, e.g., a reference standard lot of GA, and challenged with, e.g., a test lot of GA, and/or vice versa can indicate that the reference standard lot and test lot are identical. Release of cytokines by primed T-cells in response to subsequent challenge is one additional measure of immunologic identity of T-cell responses. Release profiles of cytokines potentially can detect minute differences in the particular epitopes present in a given lot of GA.

In embodiments of the present invention, the relative potency of GA in a production or test lot is determined by comparing a value representing the immunologic response of T-cells to a test lot of GA, to a value representing the same response of T-cells to a reference standard lot of GA. This potency determination describes the stimulation capacity of a test lot of GA. In a method of the invention, a test animal is immunized with a defined, or predetermined, amount of a GA reference standard lot, and the lymph node cells from lymph nodes removed from the animal are cultured. A sample of the cultured lymph node cells is stimulated by incubation with a defined, or predetermined, amount of the GA reference standard lot, and a second sample of the cultured lymph node cells is stimulated by incubation with the same defined, or predetermined, amount of the GA production or test lot. The amount of a GA response biomarker mRNA is then measured in each sample, and the amounts compared to arrive at a relative potency.

In separate embodiments, the relative cross-potency of GA is determined. The relative cross-potency compares the potencies across immunizations, that is, it compares the potencies of test and/or reference standard GA-stimulated T-cells (or T-cells stimulated with any two lots of GA being compared) obtained from different animals, wherein each animal was immunized with either the test or reference standard lot of GA. This measure provides insight into the immunization capacity of the test lot of GA, e.g., the ability of the GA test lot to elicit an immune response. This measure also provides insight into the immunization capacity of the reference standard lot of GA. In these embodiments, the process comprises immunizing at least two test animals, a first with a GA reference standard lot, and a second with a defined amount of a GA test lot. The lymph node cells removed from the immunized first and second test animals are cultured separately. Separate samples of the cultured lymph node cells removed from each animal are generated, each containing a predetermined number of the cultured lymph node cells. Each sample is separately incubated with a predetermined amount of the GA reference standard lot and a predetermined amount of a test lot of GA. Therefore, at least four incubation or stimulation samples are generated, for example, as shown in Table A:

TABLE A

Samples for Use in Determining Cross-Potency of GA

| Test Animal | Immunizing Antigen | Incubation | Stimulating Antigen |
|---|---|---|---|
| 1 | Reference Std Lot | A | Reference Std Lot |
| 1 | Reference Std Lot | B | Test Lot |
| 2 | Test Lot | C | Reference Std Lot |
| 2 | Test Lot | D | Test Lot |

The amount of at least one GA response biomarker mRNA is measured in the lymph node cells from the immunized first test animal incubated with the predetermined amount of the GA reference standard lot (represented by incubation A), and the amount of the least one GA response biomarker mRNA is measured in the lymph node cells from the immunized first test animal incubated with the predetermined amount of the test lot of GA (represented by incubation B). Similarly, the amount of at the least one GA response biomarker mRNA is measured in the lymph node cells from the immunized second test animal incubated with the predetermined amount of the GA reference standard lot (represented by incubation C), and the amount of the least one GA response biomarker mRNA in the lymph node cells from the immunized second test animal incubated with the predetermined amount of the test lot of GA (represented by incubation D).

In embodiments, a potency determination is made as described above wherein the amount of the least one GA response biomarker mRNA in incubation B is compared to the amount of the least one GA response biomarker mRNA in incubation A. In embodiments, the amount of the least one GA response biomarker mRNA in incubation C is compared to the amount of the least one GA response biomarker mRNA in incubation D.

To determine the cross-potency, the amount of the least one GA response biomarker mRNA in incubation C is compared to the amount of the least one GA response biomarker mRNA in incubation A. In embodiments, the amount of the least one GA response biomarker mRNA in incubation B is compared to the amount of the least one GA response biomarker mRNA in incubation D.

For example, using data set forth in Table B, taken from the Examples presented herein in Tables 29 (IL-2), Table 31 (IL-4), and Table 35 (IL-13), a cross-potency calculation can be carried out as shown below.

TABLE B

Example Cross-Potency Calculation

| Incubation | Immunizing Antigen | Stimulating Antigen (5 µg/mL) | IL-2 fold-change | IL-4 fold-change | IL-13 fold-change |
|---|---|---|---|---|---|
| A | Copaxone | Copaxone | 20.0 | 22.6 | 13.5 |
| B | Copaxone | GMA | 16.9 | 18.8 | 8.6 |
| C | GMA | Copaxone | 17.5 | 21.8 | 17.5 |
| D | GMA | GMA | 15.7 | 18.3 | 11.5 |

For IL-2, the Copaxone cross-potency is calculated as follows:
C/A=17.5/20.0=0.875, or 87.5%.
For IL-2, the GMA cross-potency is calculated as follows:
B/D=16.9/15.7=1.08, or 108%.
For IL-4, the Copaxone cross-potency is calculated as follows:
C/A=21.8/22.6=0.965, or 96.5%
For IL-4, the GMA cross-potency is calculated as follows:
B/D=18.8/18.3=1.03, or 103%.
For IL-13, the Copaxone cross-potency is calculated as follows:
C/A=17.5/13.5=1.3, or 130%
For IL-13, the GMA cross-potency is calculated as follows:
B/D=8.6/11.5=0.748, or 74.8%.

In embodiments, the potency is based on the comparison of two production lots. In embodiments, the process of the invention is used before potential addition of a production lot of GA to a pharmaceutical composition of GA, after addition, or otherwise as deemed appropriate.

U.S. Pat. No. 7,429,374 (issued Sep. 30, 2008), U.S. Pat. No. 7,923,215, (issued Apr. 12, 2011), and U.S. Pat. App. Pub. No. 2011/0189706 (published Aug. 4, 2011), each titled, "Process for the Measurement of the Potency of Glatiramer Acetate," and each incorporated herein by reference in its entirety, describe a GA potency assay in which secreted cytokine (protein) levels are measured.

In the methods of the present invention, the expression level of one or more response biomarker mRNA is measured. The level of mRNA expression from does not necessarily parallel the protein expression. Therefore, the level of mRNA expression can be used to provide information on response biomarkers that is not available using a secreted protein assay. For example, one advantage of an mRNA assay is that mRNA can be available for detection much earlier than the secreted protein derived from the mRNA, resulting in a faster assay. In addition to timing issues, dose-response effects of certain response biomarkers have been observed to differ between the two types of assays. Importantly, cytokines described as undetectable by U.S. Pat. No. 7,429,374, following GA stimulation of cells from GA-immunized mice, unequivocally were detected by mRNA assay, as shown herein.

In embodiments, when quantitation is carried out by mRNA amplification, the data can be normalized to expression of an internal control, e.g., a reference or housekeeping gene such as GAPDH or β-actin. Furthermore, the potency or cross-potency can be expressed in terms of fold increase relative to a control, as described herein in the Examples, where the DCCM-1 unstimulated data is control. In embodiments, the potency or cross-potency is expressed as the fold change vs control for a GA response biomarker mRNA in a sample. In embodiments, the fold change vs control for a GA response biomarker mRNA in a sample is calculated by 1) normalizing the level of the response biomarker mRNA to a reference or housekeeping gene obtained using the same sample, and 2) dividing the normalized level of the response biomarker mRNA by a negative control level. In embodiments, the negative control level is a culture medium control.

In embodiments, for evaluation of potency or cross-potency, the statistical comparison of detailed dose response curves can be performed to demonstrate similarity of the dose response curves. Any method known in the literature or to one of skill in the art can be used to demonstrate similarity of the dose response curves. In embodiments, similarity between dose response curves is determined based on a percent variance of 0 to about 15% between or among the dose response curves. In embodiments, similarity between dose response curves is determined based on a percent variance of 0%, about 1%, about 2%, about 3%, about 4%, about 5%, about 6%, about 7%, about 8%, about 9%, about 10%, about 11%, about 12%, about 13%, about 14%, or about 15% between or among the dose response curves. In embodiments, similarity between dose response curves is determined based on a percent variance of 0% to about 3%, 0% to about 4%, 0% to about 5%, 0% to about 6%, 0% to about 7%, 0% to about 8%, 0% to about 9%, 0% to about 10%, 0% to about 11%, 0% to about 12%, 0% to about 13%, 0% to about 14%, about 1% to about 3%, about 1% to about 4%, about 1% to about 5%, about 1% to about 6%, about 1% to about 7%, about 1% to about 8%, about 1% to about 9%, about 1% to about 10%, about 1% to about 11%, about 1% to about 12%, about 1% to about 13%, about 1% to about 14%, about 2% to about 4%, about 2% to about 5%, about 2% to about 6%, about 2% to about 7%, about 2% to about 8%, about 2% to about 9%, about 2% to about 10%, about 2% to about 11%, about 2% to about 12%, about 2% to about 13%, about 2% to about 14%, about 2% to about 15%, about 3% to about 5%, about 3% to about 6%, about 3% to about 7%, about 3% to about 8%, about 3% to about 9%, about 3% to about 10%, about 3% to about 11%, about 3% to about 12%, about 3% to about 13%, about 3% to about 14%, about 3% to about 15%, about 4% to about 7%, about 4% to about 8%, about 4% to about 9%, about 4% to about 10%, about 4% to about 11%, about 4% to about 12%, about 4% to about 13%, about 4% to about 14%, about 4% to about 15%, about 5% to about 8%, about 5% to about 9%, about 5% to about 10%, about 5% to about 11%, about 5% to about 12%, about 5% to about 13%, about 5% to about 14%, about 5% to about 15%, about 6% to about 9%, about 6% to about 10%, about 6% to about 11%, about 6% to about 12%, about 6% to about 13%, about 6% to about 14%, about 6% to about 15%, about 7% to about 10%, about 7% to about 11%, about 7% to about 12%, about 7% to about 13%, about 7% to about 14%, about 7% to about 15%, about 8% to about 11%, about 8% to about 12%, about 8% to about 13%, about 8% to about 14%, about 8% to about 15%, about 9% to about 12%, about 9% to about 13%, about 9% to about 14%, about 9% to about 15%, about 10% to about 13%, about 10% to about 14%, about 10% to about 15%, about 11% to about 14%, about 11% to about 15%, about 1%, about 2%, about 3%, about 4%, about 5%, about 6%, about 7%, about 8%, about 9%, about 10%, about 11%, about 12%, about 13%, about 14%, or about 15%, between or among the dose response curves.

The use of any appropriate RT-PCR quantification method known in the art and described in the literature is contemplated. Quantification methods are described by, e.g., Wong and Medrano, 2005, Biotechniques 39: 57-85, "Real-Time PCR for mRNA Quantitation," incorporated herein by reference in its entirety.

In embodiments, any reference or housekeeping gene identified as useful by one of skill in the art by known methods is used in the methods of the invention. In embodiments, the reference or housekeeping gene used is selected from: GAPDH, β-actin, Atp5b, B2m, Cyc1, Hprt, Gapdh, 18S RNA, and Rpl13a.

In embodiments of the invention, the comparisons made to determine relative potency and relative cross-potency are expressed as ratios, proportions, or percentages of the amounts of mRNA biomarker expression observed.

In embodiments of the present invention, the potency or cross-potency of the test lot of GA is compared to the potency or cross-potency of a reference standard lot of GA to obtain the relative potency or cross-potency of the test lot of GA. In embodiments wherein the relative potency or cross-potency is 100% (which also can be expressed as 1.0), the potency or cross-potency of the test lot of GA and the reference standard lot of GA are equal. In embodiments, the desired relative potency is about 80% to about 120%. In embodiments, the desired relative potency is about 85% to about 115%. In embodiments, the desired relative potency is about 90% to about 110%. In embodiments, the desired relative cross-potency is about 70% to about 130%. In embodiments, a desired relative cross-potency is about 65% to about 135%. In certain embodiments, the desired potency or desired cross-potency relative to the potency or cross-potency of the reference standard lot (the desired relative potency or the desired relative cross-potency) is about or at least about 65%, about or at least about 66%, about or at least about 67%, about or at least about 68%, about or at least about 69%, about or at least about 70%, about or at least about 71%, about or at least about 72%, about or at least about 73%, about or at least about 74%, about or at least about 75%, about or at least about 75%, about or at least about 76%, about or at least about 77%, about or at least about 78%, about or at least about 79%, about or at least about 80%, about or at least about 81%, about or at least about 82%, about or at least about 83%, about or at least about 84%, about or at least about 85%, about or at least about 86%, about or at least about 87%, about or at least about 88%, about or at least about 89%, about or at least about 90%, about or at least about 91%, about or at least about 92%, about or at least about 93%, about or at least about 94%, about or at least about 95%, about or at least about 96%, about or at least about 97%, about or at least about 98%, about or at least about 99%, about or at least about 100%, about or at least about 101%, about or at least about 102%, about or at least about 103%, about or at least about 104%, about or at least about 105%, about or at least about 106%, about or at least about 107%, about or at least about 108%, about or at least about 109%, about or at least about 110%, about or at least about 111%, about or at least about 112%, about or at least about 113%, about or at least about 114%, about or at least about 115%, about or at least about 116%, about or at least about 117%, about or at least about 118%, about or at least about 119%, about or at least about 120%, about or at least about 121%, about or at least about 122%, about or at least about 123%, about or at least about 124%, about or at least about 125%, about or at least about 126%, about or at least about 127%, about or at least about 128%, about or at least about 129%, about or at least about 130%, about or at least about 131%, about or at least about 132%, about or at least about 133%, about or at least about 134%, or about or at least about 135%. In embodiments, the desired relative potency or cross-potency is about 68% to about 132%, about 70% to about 130%, about 72% to about 128%, about 75% to about 125%, about 80% to about 120%, about 85% to about 115%, about 65% to about 110%, about 68% to about 110%, about 70% to about 110%, about 72% to about 110%, about 78% to about 110%, about 80% to about 110%, about 90% to about 110%, about 95% to about 105%, about 85% to about 110%, about 90% to about 110%, about 95% to about 110%, about 96% to about 110%, about 97% to about 110%, about 98% to about 110%, about 99% to about 110%, about 100% to about 110%, about 65% to about 105%, about 68% to about 105%, about 70% to about 105%, about 72% to about 105%, about 80% to about 105%, about 85% to about 105%, about 90% to about 105%, about 95% to about 105%, about 96% to about 105%, about 97% to about 105%, about 98% to about 105%, about 99% to about 105%, about 100% to about 105%, about 65% to about 100%, about 68% to about 100%, about 70% to about 100%, about 72% to about 100%, about 75% to about 100%, about 78% to about 100%, about 80% to about 100%, about 81% to about 100%, about 82% to about 100%, about 83% to about 100%, about 84% to about 100%, about 85% to about 100%, about 86% to about 100%, about 87% to about 100%, about 88% to about 100%, about 89% to about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, about 99% to about 100%, about 95% to about 99%, about 96% to about 99%, about 97% to about 99%, about 70% to about 135%, about 75% to about 135%, about 80% to about 135%, about 85% to about 135%, about 90% to about 135%, about 75% to about 130%, about 80% to about 130%, about 85% to about 130%, about 90% to about 130%, about 80% to about 125%, about 85% to about 125%, about 90% to about 125%, about 85% to about 120%, about 90% to about 120%, or about 95% to about 120%.

Animals

A test animal or test mammal according to the invention is any animal that can be used for evaluation of the compound, e.g., mouse, rat, guinea pig, rabbit, dog, monkey, and the like.

An appropriate test animal can be identified according to methods known to those of skill in the art combined with the teachings provided herein in the Examples. For example, many mouse strains are known in the art and are commercially available from sources including Jackson Laboratories, Charles River, Taconic, etc. Information about available inbred mouse strains is available in the published literature and in databases including the International Mouse Strain Resource (Eppig J T and Strivens M, 1999, Finding a mouse: the International Mouse Strain Resource (IMSR). Trends in Genetics 15: 81-82). Evaluation of increased cytokine secretion levels in several mouse strains is described herein in the Examples. The Examples further describe evaluation of response biomarker mRNAs from genes encoding the cytokines for potential measurement in the methods of the present invention.

In embodiments, the test animal is a mouse. In embodiments, the mouse strain has an MHC haplotype b, d, or s2. In embodiments, the strain of mouse is CSJLF1/JRj, SJL/J, BALB/cByJ, CD-1, C57BL/10J, or (SJL/J×BALB/c) F1. In embodiments, the mice are female CSJLF1/JRj, female SJL/J, female BALB/cByJ, female CD-1, female C57BL/10J, or female (SJL/J×BALB/c)F1 mice.

In embodiments where cross-potency is determined by comparing response biomarker mRNA expression in samples from different mice, each immunized with a different lot of GA, the mice are of substantially the same genotype with regard to immunologically relevant loci. In embodiments, the mice are selected from: mice of the same mouse strain, HLA-matched mice; littermates, and; twins. In embodiments, the mice are genetically identical or substantially genetically identical.

Immunization

Animal immunization procedures useful in the methods of the present invention are described herein and in the published literature, e.g., in U.S. Pat. Nos. 7,429,374 and 7,923,215. Other effective immunization procedures that induce a T-cell response to GA are identifiable by one of skill in the art. In embodiments, mice are immunized with 250 µg of GA in CFA emulsion or mannitol in CFA emulsion via footpad (intraplantar) and or lower limb/hock injection. In embodiments, mice are immunized with about 200 to about 500 μg, about 200 to about 450 μg, about 200 to about 350 μg, about 200 to about 300 μg, about 200 to about 250 μg, about 250 to about 500 μg, about 250 to about 450 μg, about 250 to about 400 μg, about 250 to about 350 μg, or about 250 to about 300 μg of GA.

In embodiments, animals at 8 weeks of age are immunized by injection into each of four footpads using a 1 mL syringe with a 27-G, ½-inch needle. For intraplantar injection, mice can be immunized with a total injection volume of 0.1 mL (about 10 μL into each of the front footpads and 40 μL into each of the hind footpads). For subcutaneous (e.g., lower limb) injection, each mouse can be immunized with a total injection volume of 0.1 mL (e.g., about 25 μL into each of the front lower limbs and 25 μL into each hock of the hind limbs).

T-Cell Cultures

In the methods of the invention, ex vivo GA-stimulation of T-cells from any source in the test animal is contemplated. In embodiments, the T-cells are from lymph node, spleen, bone marrow, or peripheral blood. T-cells can be obtained as described herein in the examples or by any method known in the art or using published in the literature.

As an example, T-cells are obtained from the immunized mice, and a primary culture prepared as follows: ten days post-immunization, immunized animals are sacrificed via cervical dislocation. Lymph nodes in the axillary and popliteal regions from immunized mice are removed and pooled into petri dishes containing 5 mL of ice cold, sterile RPMI-1640 medium. The intact lymph nodes are washed three times in 5.0 mL ice cold, sterile RPMI 1640 medium. The LN cells are isolated by pressing the LN with the plunger end of a sterile syringe. The cell suspension is first passed through a 100 μm nylon cell strainer and then washed once with 40 mL of ice cold RPMI-1640 medium. After centrifugation at ca. 200×g for 10 minutes at 4° C., the cell pellet is re-suspended in 40 mL of RPMI-1640 medium for cell counting.

A Trypan blue exclusion method can be used to determine the cell density of viable cells in the suspension as follows: for cell counting, 0.1 mL of cell suspension is transferred to a clean, sterile microcentrifuge tube with 0.65 mL of 1×DPBS and 0.25 mL of 4% Trypan blue solution, followed by addition of 20 μL of the Trypan blue-cell suspension mixture to a counting chamber. The cell density and viability are measured using an Auto T4 Cellometer. After cell counting, the LN cells are centrifuged at ca. 200×g for 10 minutes at 4° C. and re-suspended in enriched DCCM-1 medium at a cell density of $1.0 \times 10^7$ cell/mL. The LN cells can be plated into a 24-well tissue culture plate for drug treatment (stimulation).

In embodiments, LN cells are obtained from mice after sufficient time for an immune response to the GA to develop, e.g., about 9-11 days post-immunization.

Glatiramer Acetate Stimulation

T-cells, e.g., LN cells, can be stimulated with antigen (GA) according to any suitable method known in the art or described in the literature. For example, a predetermined number of LN cells, e.g., 0.5 mL of cells ($5 \times 10^6$ cells/well) from an animal immunized with GA can be stimulated with a predetermined amount of a reference standard lot of GA as desired. In a separate sample, the same predetermined number of the LN cells can be stimulated with the same predetermined amount of a test lot of GA. GA dilution samples can be prepared by adding 100 μL of GA (20 mg/mL) to 19.9 mL of enriched DCCM-1 medium, yielding a 100 μg/mL stock solution useful for preparing GA samples at different concentrations as desired.

For example, in a 24-well tissue culture plate, a predetermined amount of test lot or reference standard lot of GA stock solution is added to a well containing a predetermined number of LN cells to give a desired concentration of GA. The same predetermined number of T-cells from control animals immunized with mannitol similarly can be treated with the same predetermined amount of the lot of GA using the same procedure.

In embodiments of the present invention, a test animal is immunized with a defined amount of a GA reference standard. At least one sample containing a predetermined number of the lymph node cells from the immunized animal is incubated in the presence of the GA reference standard, and at least one sample of the lymph node cells from the immunized animal is incubated in the presence of a test lot of GA. This stimulation can induce the expression of molecules involved in the immune response, e.g., mRNAs encoding cytokines and cytokine receptors.

In embodiments, a sample of lymph node cells is incubated with a concentration of GA of at least about 0.3 μg/mL to about 100 μg/mL. In embodiments, the concentration is at least about 0.3 μg/mL, at least about 0.4 μg/mL, at least about 0.5 μg/mL, at least about 0.6 μg/mL, at least about 0.7 μg/mL, at least about 0.8 μg/mL, at least about 0.9 μg/mL, at least about 1 μg/mL, at least about 1.5 μg/mL, at least about 2 μg/mL, at least about 2.5 μg/mL, at least about 3 μg/mL, at least about 3.5 μg/mL, at least about 4 μg/mL, at least about 4.5 μg/mL, at least about 5 μg/mL, at least about 5.5 μg/mL, at least about 6 μg/mL, at least about 6.5 μg/mL, at least about 7 μg/mL, at least about 7.5 μg/mL, at least about 8 μg/mL, at least about 8.5 μg/mL, at least about 9 μg/mL, at least about 9.5 μg/mL, at least about 10 μg/mL, at least about 10.5 μg/mL, at least about 11 μg/mL, at least about 11.5 μg/mL, at least about 12 μg/mL, at least about 12.5 μg/mL, at least about 13 μg/mL, at least about 13.5 μg/mL, at least about 14 μg/mL, at least about 14.5 μg/mL, at least about 15 μg/mL, at least about 15.5 μg/mL, at least about 16 μg/mL, at least about 16.5 μg/mL, at least about 17 μg/mL, at least about 17.5 μg/mL, at least about 18 μg/mL, at least about 18.5 μg/mL, at least about 19 μg/mL, at least about 19.5 μg/mL, at least about 20 μg/mL, at least about 21.5 μg/mL, at least about 22 μg/mL, at least about 22.5 μg/mL, at least about 23 μg/mL, at least about 24 μg/mL, at least about 24.5 μg/mL, at least about 25 μg/mL, at least about 25.5 μg/mL, at least about 26 μg/mL, at least about 26.5 μg/mL, at least about 27 μg/mL, at least about 27.5 μg/mL, at least about 28 μg/mL, at least about 28.5 μg/mL, at least about 29 μg/mL, at least about 29.5 μg/mL, at least about 30 μg/mL, at least about 35 μg/mL, at least about 40 μg/mL, at least about 45 μg/mL, at least about 50 μg/mL, at least about 55 μg/mL, at least about 60 μg/mL, at least about 65 μg/mL, at least about 70 μg/mL, at least about 75 μg/mL, at least about 80 μg/mL, at least about 85 μg/mL, at least about 90 μg/mL, at least about 95 μg/mL, or at least about 100 μg/mL. In embodiments, the concentration is about 0.3 to about 15 μg/mL, about 0.3 to about 10 μg/mL, about 0.3 to about 8 μg/mL, about 0.3 to about 6 μg/mL, about 0.3 to about 5 μg/mL, about 0.3 to about 4 μg/mL, about 0.3 to about 3 μg/mL, about 0.3 to about 2.5 μg/mL, about 0.3 to about 2 μg/mL, about 0.3 to about 1 μg/mL, about 1 to about 15 μg/mL, about 1 to about 10 μg/mL, about 1 to about 9 μg/mL, about 1 to about 8 μg/mL, about 1 to about 7 μg/mL, about 1 to about 6 μg/mL, about 1 to about 5 μg/mL, about 1 to about 4 μg/mL, about 1 to about 3 μg/mL, about 1 to about 2.5 µg/mL, about 1 to about 2 µg/mL, about 2 to about 30 µg/mL, about 2 to about 29 µg/mL, about 2 to about 28 µg/mL, about 2 to about 27 µg/mL, about 2 to about 26 µg/mL, about 2 to about 25 µg/mL, about 2 to about 24 µg/mL, about 2 to about 23 µg/mL, about 2 to about 22 µg/mL, about 2 to about 21 µg/mL, about 2 to about 20 µg/mL, about 2 to about 19 µg/mL, about 2 to about 18 µg/mL, about 2 to about 17 µg/mL, about 2 to about 16 µg/mL, about 2 to about 15 µg/mL, about 2 to about 14 µg/mL, about 2 to about 13 µg/mL, about 2 to about 12 µg/mL, about 2 to about 11 µg/mL, about 2 to about 10 µg/mL, about 2 to about 5 µg/mL, about 2.5 to about 30 µg/mL, about 2.5 to about 29 µg/mL, about 2.5 to about 28 µg/mL, about 2.5 to about 27 µg/mL, about 2.5 to about 26 µg/mL, about 2.5 to about 25 µg/mL, about 2.5 to about 24 µg/mL, about 2.5 to about 23 µg/mL, about 2.5 to about 22 µg/mL, about 2.5 to about 21 µg/mL, about 2.5 to about 20 µg/mL, about 2.5 to about 19 µg/mL, about 2.5 to about 18 µg/mL, about 2.5 to about 17 µg/mL, about 2.5 to about 16 µg/mL, about 2.5 to about 15 µg/mL, about 2.5 to about 14 µg/mL, about 2.5 to about 13 µg/mL, about 2.5 to about 12 µg/mL, about 2.5 to about 11 µg/mL, about 2.5 to about 10 µg/mL, about 2.5 to about 5 µg/mL, about 3 to about 30 µg/mL, about 3 to about 29 µg/mL, about 3 to about 28 µg/mL, about 3 to about 27 µg/mL, about 3 to about 26 µg/mL, about 3 to about 25 µg/mL, about 3 to about 24 µg/mL, about 3 to about 23 µg/mL, about 3 to about 22 µg/mL, about 3 to about 21 µg/mL, about 3 to about 20 µg/mL, about 3 to about 19 µg/mL, about 3 to about 18 µg/mL, about 3 to about 17 µg/mL, about 3 to about 16 µg/mL, about 3 to about 15 µg/mL, about 3 to about 14 µg/mL, about 3 to about 13 µg/mL, about 3 to about 12 µg/mL, about 3 to about 11 µg/mL, about 3 to about g/mL, about 3.5 to about 30 µg/mL, about 3.5 to about 29 µg/mL, about 3.5 to about 28 µg/mL, about 3.5 to about 27 µg/mL, about 3.5 to about 26 µg/mL, about 3.5 to about 25 µg/mL, about 3.5 to about 24 µg/mL, about 3.5 to about 23 µg/mL, about 3.5 to about 22 µg/mL, about 3.5 to about 21 µg/mL, about 3.5 to about 20 µg/mL, about 3.5 to about 19 µg/mL, about 3.5 to about 18 µg/mL, about 3.5 to about 17 µg/mL, about 3.5 to about 16 µg/mL, about 3.5 to about 15 µg/mL, about 3.5 to about 14 µg/mL, about 3.5 to about 13 µg/mL, about 3.5 to about 12 µg/mL, about 3.5 to about 11 µg/mL, about 3.5 to about 10 µg/mL, about 4 to about 30 µg/mL, about 4 to about 29 µg/mL, about 4 to about 28 µg/mL, about 4 to about 27 µg/mL, about 4 to about 26 µg/mL, about 4 to about 25 µg/mL, about 4 to about 24 µg/mL, about 4 to about 23 µg/mL, about 4 to about 22 µg/mL, about 4 to about 21 µg/mL, about 4 to about 20 µg/mL, about 4 to about 19 µg/mL, about 4 to about 18 µg/mL, about 4 to about 17 µg/mL, about 4 to about 16 µg/mL, about 4 to about 15 µg/mL, about 4 to about 14 µg/mL, about 4 to about 13 µg/mL, about 4 to about 12 µg/mL, about 4 to about 11 µg/mL, about 4 to about 10 µg/mL, about 4.5 to about 30 µg/mL, about 4.5 to about 29 µg/mL, about 4.5 to about 28 µg/mL, about 4.5 to about 27 µg/mL, about 4.5 to about 26 µg/mL, about 4.5 to about 25 µg/mL, about 4.5 to about 24 µg/mL, about 4.5 to about 23 µg/mL, about 4.5 to about 22 µg/mL, about 4.5 to about 21 µg/mL, about 4.5 to about 20 µg/mL, about 4.5 to about 19 µg/mL, about 4.5 to about 18 µg/mL, about 4.5 to about 17 µg/mL, about 4.5 to about 16 µg/mL, about 4.5 to about 15 µg/mL, about 4.5 to about 14 µg/mL, about 4.5 to about 13 µg/mL, about 4.5 to about 12 µg/mL, about 4.5 to about 11 µg/mL, about 4.5 to about 10 µg/mL, about 5 to about 75 µg/mL, about 5 to about 50 µg/mL, about 5 to about 40 µg/mL, about 5 to about 30 µg/mL, about 5 to about 29 µg/mL, about 5 to about 28 µg/mL, about 5 to about 27 µg/mL, about 5 to about 26 µg/mL, about 5 to about 25 µg/mL, about 5 to about 24 µg/mL, about 5 to about 23 µg/mL, about 5 to about 22 µg/mL, about 5 to about 21 µg/mL, about 5 to about 20 µg/mL, about 5 to about 19 µg/mL, about 5 to about 18 µg/mL, about 5 to about 17 µg/mL, about 5 to about 16 µg/mL, about 5 to about 15 µg/mL, about 5 to about 14 µg/mL, about 5 to about 13 µg/mL, about 5 to about 12 µg/mL, about 5 to about 11 µg/mL, about 5 to about 10 µg/mL, about 10 to about 75 µg/mL, about 10 to about 50 µg/mL, about 10 to about 50 µg/mL, about 10 to about 30 µg/mL, about 10 to about 25 µg/mL, about 10 to about 20 µg/mL, about 10 to about 15 µg/mL, about 15 to about 75 µg/mL, about 15 to about 50 µg/mL, about 15 to about 40 µg/mL, about 15 to about 30 µg/mL, about 15 to about 25 µg/mL, or about 15 to about 20 µg/mL.

In embodiments of the present invention, the reference standard lot of GA used for immunization is Copaxone or any other lot of GA as desired. In these embodiments, a separate sample of cells from the immunized animals are treated with the lot of GA that was used for immunization, and a second sample of the cells, are each treated with a second lot (a test lot) of GA. In embodiments, the reference standard lot of GA is not Copaxone. In these embodiments, the test lot can be Copaxone or any other lot of GA as desired. In embodiments, more than one test lot of GA is evaluated in parallel with the first test lot.

In embodiments, wherein cross-potency is determined, more than one mouse is immunized, each with a different lot of GA. Separate samples of LN cells obtained from each of the immunized mice are stimulated with the different lots of GA, such that cells from each immunization are separately stimulated with each different lot of GA.

Response Biomarker mRNA

An mRNA species potentially modulated by GA-stimulation is contemplated for use as a response biomarker in the methods of the present invention. In embodiments, a response biomarker is an mRNA transcribed from a gene encoding, e.g., CD25, CD69, CD71, CD86 (CD86 molecule), CD137, CD154, CD278 (ICOS, Inducible T-cell co-stimulator), CD279, HLA-DR, GATA3 (GATA binding protein 3), HLA-DMA (Major histocompatibility complex, class II, DM alpha), HLA-DMB (Major histocompatibility complex, class II, DM beta), IFN-γ (Interferon gamma), IFN-γR2 (Interferon gamma receptor), IL-2 (Interleukin 2), IL-4 (Interleukin 4), IL-5 (Interleukin 5), IL-6 (Interleukin 6), IL-8 (CXCL-8), RANTES (CCL5), CCL1, CXCL4, CXCL7, IL-10 (Interleukin 10), IL-13 (Interleukin 13), IL-18 (Interleukin 18), IL-12RB1 (Interleukin 12 receptor, beta), IL-17A (Interleukin 17A), IL-17F (Interleukin 17F), IL-18R1 (Interleukin 18 receptor 1), IL-2RA (Interleukin 2 receptor, alpha 2), IL-2RG (Interleukin 2 receptor, gamma), IL4-R (Interleukin 4 receptor), IL-6R (Interleukin 6 receptor), IL-21 (Interleukin 21), IL-22 (Interleukin 22), IL-13 (Interleukin 1-beta), Tbx21 (T-box 21), TGFBR2 (Transforming growth factor, beta receptor II), TNF (Tumor necrosis factor, TNF-α), TNF-β (LT), TGF-β, FOXP3 (Forkhead box P3), or IL-10RB (Interleukin 10 receptor, beta). Expression of these genes can be evaluated using commercially available services, reagents and/or kits, e.g., the MouseWG-6 v2.0 Expression BeadChip Kit (Illumina, Inc., San Diego, Calif.).

In embodiments, a response biomarker mRNA is transcribed from a gene encoding a cytokine selected from, e.g., IL-2, IL-4, IL-5, IL-6, IL-10, IL-13, or IL-17, IL-18, IL-21, IL-22, IFN-γ, TNF-α (TNF), TNF-β (LT), TGF-β, and IL-1β. In embodiments, a response biomarker mRNA is transcribed from a gene encoding an activation marker or cytokine receptor selected from, e.g., CD25, CD69, CD71, CD86, CD137, CD154, CD278, CD279, GATA3, Tbx21, HLA-DMA, HLA-DMB, IFN-γR2, IL-12RB1, IL-2RA, IL-2RG, IL-4R, IL-6R, IL-10RB, TGFBR2, FOXP3, and HLA-DR. In embodiments, a response biomarker mRNA is transcribed from a gene encoding a chemokine selected from, e.g., IL-8 (CXCL8), RANTES (CCL5), CCL1, CXCL4, and CXCL7. In embodiments, a response biomarker mRNA is transcribed from a gene encoding a Th1-associated cytokine, a Th2-associated cytokine, a Th17-associated cytokine, or a $T_{FH}$-associated cytokine. In embodiments, a response biomarker mRNA is transcribed from a gene encoding a Th1-associated cytokine and is IFN-γ, IL-2, IL-1β, TNF-α, or CXCL1. In embodiments, a response biomarker mRNA is transcribed from a gene encoding a Th2-associated cytokine selected from: IL-4, IL-5, IL-10, or IL-13. In embodiments, a response biomarker mRNA is transcribed from a gene encoding a Th17-associated cytokine selected from: IL-17, and IL-22. In embodiments, a response biomarker mRNA is transcribed from a gene encoding a $T_{FH}$-associated cytokine that is IL-21. In embodiments, a response biomarker mRNA is transcribed from a gene encoding a key regulatory associated cytokine selected from IL-10 and TGF-β.

In embodiments, a response biomarker mRNA is transcribed from a gene encoding IL-2, IL-4, IL-5, IL-6, IL-10, IL-13, IL-17, IL-22, IFN-γ, TNF-α, CD25, or IL11-β. In embodiments, a response biomarker mRNA is transcribed from a gene encoding IL-4, IL-5, IL-13, IL-17, IL-22, TNF-α, CD-25, or IL1-β. In embodiments, a response biomarker mRNA is transcribed from a gene encoding IL-4, IL-13, or TNF-α. In embodiments, a response biomarker mRNA is transcribed from a gene encoding IL-2, IL-4, IL-5, IL-13, IL-17, IL-22, IFN-γ, or CD25. In embodiments, a response biomarker mRNA is transcribed from a gene encoding IL-4, IL-5, IL-13, IL-17, or CD25. In embodiments, a response biomarker mRNA is transcribed from a gene encoding IL-2, IL-4, IL-5, IL-6, IL-13, IL-17, IL-22, IFN-γ, or TNF-α. In embodiments, a response biomarker mRNA is transcribed from a gene encoding IL-4, IL-5, IL-13, IL-17, IL-22, TNF-α. In embodiments, a response biomarker mRNA is transcribed from a gene encoding IL-4, IL-5, IL-13, IL-17, or IFN-γ. In embodiments, a response biomarker mRNA is transcribed from a gene encoding IL-4, IL-5, IL-13, or IL-17. In embodiments, a response biomarker mRNA is transcribed from a gene encoding CD25, IL-4, or IL-13. In embodiments, a response biomarker mRNA is transcribed from a gene encoding IL-4, or IL-13.

In embodiments, the mouse strain is CSJLF1/JRj, SJL/J, BALB/cByJ, CD-1, C57BL/10J, or (SJL/J×BALB/c)F1. In embodiments, the mouse strain is CSJLF1/JRj, SJL/J, BALB/cByJ, CD-1, C57BL/10J, or (SJL/J×BALB/c)F1, and the response biomarker mRNA is transcribed from a gene encoding murine IL-2, IL-4, IL-5, IL-6, IL-10, IL-13, or IL-17, IL-18, IL-21, IL-22, IFN-γ, TNF-α (TNF), TNF-β (LT), TGF-β, and IL-1β. In embodiments, more than one response biomarker mRNA is measured. In particular embodiments, more than one response biomarker mRNA is measured in the same sample, e.g., by multiplex PCR. In particular embodiments, the test animal is a SJL/J mouse, and the response biomarker mRNA is transcribed from a gene encoding mIL-2, mIL-4, mIl-5, mIL-13, or mIFN-γ. In particular embodiments, the test animal is a BALB/cByJ mouse, and the response biomarker mRNA is transcribed from a gene encoding mIL-2, mIFN-γ, mIL-4, mIL-5, mIL-10, or mIL-13. In other embodiments, the test animal is a CD-1 mouse, and the response biomarker mRNA is transcribed from a gene encoding mIL-2, mIFN-γ, mIL-5, mIL-10, or mIL-13. In certain embodiments, the test animal is a C57BL/10J mouse, and the response biomarker mRNA is transcribed from a gene encoding mIL-2 or mIFN-γ. In other embodiments, the test animal is an (SJL/J×BALB/C) F1 mouse, and the response biomarker mRNA is transcribed from a gene encoding mIFN-γ, mTNF-α, mIL-4, mIL-5, mIL-10, mIL-13, mIL-17, mCD69, or mCD25. In embodiments, the test animal is a CSJLF1/JRj mouse, and the response biomarker mRNA is transcribed from a gene encoding IL-4, IL-5, IL-13, or IL-17.

In specific embodiments of the present invention, the test animal is a BALB/cByJ mouse immunized by intraplantar injection, and the response biomarker measured is mIFN-γ, IL-4, or IL-5. In embodiments, the test animal is a BALB/cByJ mouse immunized by lower limb injection, and the response biomarker measured is IL-2. In other embodiments, the test animal is a CD-1 mouse immunized by intraplantar injection, and the response biomarker measured is IL-2, mIFN-γ, IL-4, IL-5, or IL-10.

The present invention also relates to methods for identifying response biomarker mRNA species that can be measured in the potency assays of the present invention. Additional response biomarker mRNAs can be identified by one of skill in the art in accordance with the teachings presented herein, which demonstrate identification of cytokine mRNA species that increase in response to GA stimulation of T-cells from mice immunized with GA. In embodiments, an appropriate response biomarker for use in the potency assays of the present invention is an mRNA species that is determined to be modulated in response to GA stimulation of T-cells from mice immunized with GA, and wherein the modulation is found to be consistent in two or more repeat tests. In embodiments, the mRNA species is modulated in response to GA stimulation by at least about 2-fold to about 50-fold, about 2-fold to about 45-fold, about 2-fold to about 40-fold, about 2-fold to about 35-fold, about 2-fold to about 30-fold, about 2-fold to about 25-fold, about 2-fold to about 22-fold, about 2-fold to about 20-fold, about 2-fold to about 15-fold, about 2-fold to about 12-fold, about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, 3-fold to about 50-fold, about 3-fold to about 45-fold, about 3-fold to about 40-fold, about 3-fold to about 35-fold, about 3-fold to about 30-fold, about 3-fold to about 25-fold, about 3-fold to about 22-fold, about 3-fold to about 20-fold, about 3-fold to about 15-fold, about 3-fold to about 12-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 4-fold to about 50-fold, about 4-fold to about 45-fold, about 4-fold to about 40-fold, about 4-fold to about 35-fold, about 4-fold to about 30-fold, about 4-fold to about 25-fold, about 4-fold to about 22-fold, about 4-fold to about 20-fold, about 4-fold to about 15-fold, about 4-fold to about 12-fold, about 4-fold to about 10-fold, about 4-fold to about 9-fold, about 4-fold to about 8-fold, about 4-fold to about 7-fold, about 4-fold to about 6-fold, about 5-fold to about 50-fold, about 5-fold to about 45-fold, about 5-fold to about 40-fold, about 5-fold to about 35-fold, about 5-fold to about 30-fold, about 5-fold to about 25-fold, about 5-fold to about 22-fold, about 5-fold to about 20-fold, about 5-fold to about 15-fold, about 5-fold to about 12-fold, about 5-fold to about 10-fold, about 5-fold to about 9-fold, about 5-fold to about 8-fold, about 5-fold to about 7-fold, about 7-fold to about 50-fold, about 7-fold to about 45-fold, about 7-fold to about 40-fold, about 7-fold to about 35-fold, about 7-fold to about 30-fold, about 7-fold to about 25-fold, about 7-fold to about 22-fold, about 7-fold to about 20-fold, about 7-fold to about 15-fold, about 7-fold to about 12-fold, about 7-fold to about 10-fold, about 7-fold to about 9-fold, about 10-fold to about 50-fold, about 10-fold to about 45-fold, about 10-fold to about 40-fold, about 10-fold to about 35-fold, about 10-fold to about 30-fold, about 10-fold to about 25-fold, about 10-fold to about 22-fold, about 10-fold to about 20-fold, about 10-fold to about 15-fold, about 15-fold to about 50-fold, about 15-fold to about 45-fold, about 15-fold to about 40-fold, about 15-fold to about 35-fold, about 15-fold to about 30-fold, about 15-fold to about 25-fold, about 15-fold to about 22-fold, about 15-fold to about 20-fold, about 20-fold to about 50-fold, about 20-fold to about 45-fold, about 20-fold to about 40-fold, about 20-fold to about 35-fold, about 20-fold to about 30-fold, about 20-fold to about 25-fold, about 25-fold to about 50-fold, about 25-fold to about 45-fold, about 25-fold to about 40-fold, about 25-fold to about 35-fold, about 25-fold to about 30-fold, about 30-fold to about 50-fold, about 30-fold to about 45-fold, about 30-fold to about 40-fold, about 30-fold to about 35-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 20-fold, at least about 25-fold, at least about 30-fold, at least about 2-fold, at least about 35-fold, at least about 40-fold, at least about 45-fold, or at least about 50-fold. Measurement of potential response biomarker mRNAs is described elsewhere herein.

Measurement of Response Biomarker mRNA

Response biomarker mRNA species can be quantitatively measured using any of a number of commercially available assay kits and systems, or according to any method described in the art. The use in the methods of the invention of any appropriate quantitative method for measuring mRNA expression levels known in the art is contemplated. For example, reverse transcription and amplification of mRNA can be carried out using PCR methods including RT-PCR, and real time reverse-transcription PCR (qRT-PCR). PCR methods for quantitating gene expression are described by, e.g., VanGuilder, et al., 2008, "Twenty-five years of quantitative PCR for gene expression analysis," Biotechniques 44: 619-626, and Bustin, et al., 2005, "Quantitative real-time RT-PCR—a perspective," Journal of Molecular Endocrinology, 34:597-601, each incorporated herein by reference in its entirety. Quantitative PCR of mouse cytokine mRNAs is described by, e.g., Overbergh, et al., 1999, "Quantification of murine cytokine mRNAs using real time quantitative reverse transcriptase PCR," Cytokine 11(4): 305-312, incorporated herein by reference, describing probes and primers for quantifying IL-1, IL-2, IL-4, IL-5, IL-6, IL-7, IL-10, IL-12, p40, IL-13, IL-15, IFN-γ, TNF-α, TGF-β and iNOS.

Murine cytokine RT-PCR kits are widely available, e.g., from Fisher Scientific, Life Technologies, and SABiosciences. For example, the Life Technologies Cytokine Mouse 20-Plex Panel simultaneously allows measurement of IP-10, MIP-1α, MCP-1, IL-13, IFN-γ, IL-1a, FGF-Basic, IL-10, IL-12, IL-17, MIG, GM-CSF, TNF-α, IL-11, IL-2, IL-4, IL-5, IL-6, VEGF, and KC. The SABiosciences Mouse Common Cytokines RT$^2$ Profiler™ PCR Array can be customized to measure subsets of 84 cytokine genes. In embodiments, TaqMan Universal PCR Master Mix (Cat. #4304437) and primers/probes for mouse cytokines IL-2 (Cat. #4331182; ID Mm00434256_m1), IL-4 (Cat. #4331182; ID Mm00445259_m1), IL-5 (Cat. #4331182; ID Mm00439646_m1), IL-10 (Cat. #4331182; ID Mm00439614_m1), IL-13 (Cat. #4331182; ID Mm00434204_m1), IFN-γ (Cat. #4331182; ID Mm01168134_m1) and TNF-α (Cat. #4331182; ID Mm00443260_g1) obtained from Life Technologies is used.

In embodiments, transcript levels are evaluated using the Illumina MouseWG-6 v2.0 Expression BeadChip Kit or the MouseRef-8 v2.0 Expression BeadChip Kit is used (Illumina, Inc., San Diego, Calif.). Transcriptome analyses can be carried out using other methods, e.g., RNA-Seq (Nagalakshmi, et al., January 2010, RNA-Seq: A Method for Comprehensive Transcriptome Analysis," Current Protocols in Molecular Biology, Wiley Interscience, Unit 4.11, Supplement 89, Copyright 2010 John Wiley & Sons, Inc., incorporated herein by reference in its entirety).

Acceptance criteria can include, e.g., analysis of each stimulation in triplicate, induction of a target gene by the positive control ConA that is greater than or equivalent to the induction by the highest concentration of GA, induction of a target gene by the negative control MBP that is less than 2 fold of medium control, and amplification of NTC (no template control) control that is below the detectable level. In embodiments, if a PCR run for a target gene does not meet the above acceptance criteria, the specific run will be repeated.

In the methods of the present invention, a response biomarker mRNA is measured to provide an indication of the potency of the test lot of GA. The potency of the test lot of GA is represented by its ability to effect a response that is relevant to the known or likely mechanism of GA action. It follows that specific induction of T-cell cytokine expression by GA-stimulation of T-cells can serve an indicator of GA test lot potency. In embodiments, the response biomarker mRNA is an RNA species transcribed from the biomarker gene. In embodiments, the measured response biomarker mRNA encodes the biomarker protein. In embodiments, detection methods measure any given portion of an mRNA transcript that is transcribed from a gene encoding the biomarker protein. In embodiments, measurement is carried out by nucleic acid amplification or other detection methods known in the art employing primers or probes that hybridize to any part of the mRNA transcript as suitable for producing a quantifiable signal.

The GA stimulation time is critical. In general, a timeframe is selected at which an easily detectable and highly reproducible increase or decrease in the biomarker mRNA level is observed. The optimal time after initiation of stimulation at which to measure a response to the incubation of the cells with GA is expected to vary based on the expression profile of the particular response biomarker mRNA. The effect of stimulation on expression of certain biomarker mRNAs has been observed to taper off with incubation time (see Examples), therefore later timepoints may not prove useful.

In embodiments of the methods of the present invention, the GA response biomarker mRNA is measured before about 24 hours after GA stimulation is initiated. In embodiments of the methods of the present invention, the GA response biomarker mRNA is measured before about 23, about 22, about 21, or about 20 hours after GA stimulation is initiated.

In embodiments of the methods of the invention, the GA response biomarker mRNA is measured at about 4 to about 6 hours following initiation of incubation (stimulation) of the LN cells with the GA test or reference standard lot. In embodiments of the methods of the invention, the GA response biomarker mRNA is measured at about 1 hour to about 24 hours following initiation of incubation of the LN cells with the GA test or reference standard lot. In embodiments, the GA response biomarker mRNA is measured at about 1 hour, at about 1.25 hours, at about 1.5 hours, at about 1.75 hours, at about 2 hours, at about 2.25 hours, at about 2.5 hours, at about 2.75 hours, at about 3 hours, at about 3.25 hours, at about 3.5 hours, at about 3.75 hours, at about 4 hours, at about 4.25 hours, at about 4.5 hours, at about 4.75 hours, at about 5 hours, at about 5.25 hours, at about 5.5 hours, at about 5.75 hours, at about 6 hours, at about 6.25 hours, at about 6.5 hours, at about 6.75 hours, at about 7 hours, at about 7.25 hours, at about 7.5 hours, at about 7.75 hours, at about 8 hours, at about 8.25 hours, at about 8.5 hours, at about 8.75 hours, at about 9 hours, at about 9.25 hours, at about 9.5 hours, at about 9.75 hours, at about 10 hours, at about 10.25 hours, at about 10.5 hours, at about 10.75 hours, at about 11 hours, at about 11.25 hours, at about 11.5 hours, at about 11.75 hours, at about 12 hours, at about 12.5 hours, at about 13 hours, at about 13.5 hours, at about 14 hours, at about 14.5 hours, at about 15 hours, at about 15.5 hours, at about 16 hours, at about 17 hours, at about 18 hours, at about 19 hours, at about 20 hours, at about 21 hours, at about 22 hours, at about 23, or at about 24 hours following initiation of incubation (stimulation) of the LN cells with the GA test or reference standard lot.

In embodiments, the GA response biomarker mRNA is measured at about 2 hours to about 16 hours, about 2 hours to about 15 hours about 2 hours to about 14 hours, about 2 hours to about 13 hours, about 2 hours to about 12 hours, about 2 hours to about 11 hours, about 2 hours to about 10 hours, about 2 hours to about 9 hours, about 2 hours to about 8 hours, about 2 hours to about 7 hours, about 2 hours to about 6 hours, about 2.5 hours to about 16 hours, about 2.5 hours to about 15 hours about 2.5 hours to about 14 hours, about 2.5 hours to about 13 hours, about 2.5 hours to about 12 hours, about 2.5 hours to about 11 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5.5 hours, about 2.5 hours to about 5 hours, about 2.5 hours to about 4 hours, about 3 hours to about 16 hours, about 3 hours to about 15 hours about 3 hours to about 14 hours, about 3 hours to about 13 hours, about 3 hours to about 12 hours, about 3 hours to about 11 hours, about 3 hours to about 10 hours, about 3 hours to about 9 hours, about 3 hours to about 8 hours, about 3 hours to about 7 hours, about 3 hours to about 6 hours, about 3 hours to about 5.5 hours, about 3 hours to about 5 hours, about 3 hours to about 4 hours, about 3.5 hours to about 16 hours, about 3.5 hours to about 15 hours about 3.5 hours to about 14 hours, about 3.5 hours to about 13 hours, about 3.5 hours to about 12 hours, about 3.5 hours to about 11 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5.5 hours, about 3.5 hours to about 5 hours, about 4 hours to about 16 hours, about 4 hours to about 15 hours, about 4 hours to about 14 hours, about 4 hours to about 13 hours, about 4 hours to about 12 hours, about 4 hours to about 11 hours, about 4 hours to about 10 hours, about 4 hours to about 9 hours, about 4 hours to about 8 hours, about 4 hours to about 7 hours, about 4 hours to about 6 hours, about 4 hours to about 5.5 hours, about 5 hours to about 16 hours, about 5 hours to about 15 hours, about 5 hours to about 14 hours, about 5 hours to about 13 hours, about 5 hours to about 12 hours, about 5 hours to about 11 hours, about 5 hours to about 10 hours, about 5 hours to about 9 hours, about 5 hours to about 8 hours, about 5 hours to about 7 hours, about 5 hours to about 6 hours, about 6 hours to about 16 hours, about 6 hours to about 15 hours, about 6 hours to about 14 hours, about 6 hours to about 13 hours, about 6 hours to about 12 hours, about 6 hours to about 11 hours, about 6 hours to about 10 hours, about 6 hours to about 9 hours, about 6 hours to about 8 hours, about 6 hours to about 7 hours, about 7 hours to about 16 hours, about 7 hours to about 15 hours, about 7 hours to about 14 hours, about 7 hours to about 13 hours, about 7 hours to about 12 hours, about 7 hours to about 11 hours, about 7 hours to about 10 hours, about 7 hours to about 9 hours, about 7 hours to about 8 hours, about 2 hours to about 24 hours, about 2 hours to about 20 hours, about 2 hours to about 18 hours, about 2 hours to about 16 hours, about 4 hours to about 24 hours, about 4 hours to about 20 hours, about 4 hours to about 18 hours, about 4 hours to about 16 hours, about 6 hours to about 24 hours, about 6 hours to about 20 hours, about 6 hours to about 18 hours, about 6 hours to about 16 hours, about 8 hours to about 24 hours, about 8 hours to about 20 hours, about 8 hours to about 18 hours, or about 8 hours to about 16 hours, following initiation of incubation (stimulation) of the LN cells with the GA test or reference standard lot.

Response Biomarker mRNA Panels

In embodiments, a panel of biomarker mRNA species is measured using the methods of the invention. In embodiments, the mRNAs in the panel are measured simultaneously, e.g., by multiplex PCR.

In embodiments, the invention relates to a composition comprising a panel of biomarker species.

In embodiments, a panel of biomarker mRNA species comprises at least two mRNA species. In embodiments, a panel of biomarker mRNA species comprises 2 to 50 mRNA species. In embodiments, a panel of biomarker mRNA species comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, or at least 50 mRNA species. In embodiments, a panel of biomarker mRNA species comprises 2 to 50, 2 to 5, 2 to 10, 2 to 12, 2 to 15, 2 to 20, 2 to 25, 2 to 30, 2 to 35, 2 to 40, 2 to 45, 3 to 50, 3 to 5, 3 to 10, 3 to 12, 3 to 15, 3 to 20, 3 to 25, 3 to 30, 3 to 35, 3 to 40, 3 to 45, 4 to 50, 4 to 10, 4 to 12, 4 to 15, 4 to 20, 4 to 25, 4 to 30, 4 to 35, 4 to 40, 4 to 45, 5 to 50, 5 to 10, 5 to 12, 5 to 15, 5 to 20, 5 to 25, 5 to 30, 5 to 35, 5 to 40, 5 to 45, 6 to 50, 6 to 12, 6 to 15, 6 to 20, 6 to 25, 6 to 30, 6 to 35, 6 to 40, 6 to 45, 7 to 50, 7 to 12, 7 to 15, 7 to 20, 7 to 25, 7 to 30, 7 to 35, 7 to 40, 7 to 45, 8 to 50, 8 to 15, 8 to 20, 8 to 25, 8 to 30, 8 to 35, 8 to 40, 8 to 45, 9 to 50, 9 to 15, 9 to 20, 9 to 25, 9 to 30, 9 to 35, 9 to 40, 9 to 45, 10 to 50, 10 to 15, 10 to 20, 10 to 25, 10 to 30, 10 to 35, 10 to 40, 10 to 45, 12 to 50, 12 to 20, 12 to 25, 12 to 30, 12 to 35, 12 to 40, 12 to 45, 15 to 50, 15 to 25, 15 to 30, 15 to 40, 20 to 50, 20 to 25, 20 to 30, 20 to 40, 25 to 50, 25 to 40, 30 to 50, or 30 to 45, mRNA species.

In embodiments, a panel of biomarker mRNA species comprises at least two mRNA species, each transcribed from a genes encoding CD25, CD69, CD71, CD86 (CD86 molecule), CD137, CD154, CD278 (ICOS, Inducible T-cell co-stimulator), CD279, HLA-DR, GATA3 (GATA binding protein 3), HLA-DMA (Major histocompatibility complex, class II, DM alpha), HLA-DMB (Major histocompatibility complex, class II, DM beta), IFN-γ (Interferon gamma), IFN-γR2 (Interferon gamma receptor), IL-2 (Interleukin 2), IL-4 (Interleukin 4), IL-5 (Interleukin 5), IL-6 (Interleukin 6), IL-8 (CXCL-8), RANTES (CCL5), CCL1, CXCL4, CXCL7, IL-10 (Interleukin 10), IL-13 (Interleukin 13), IL-18 (Interleukin 18), IL-12RB1 (Interleukin 12 receptor, beta), IL-17A (Interleukin 17A), IL-17F (Interleukin 17F), IL-18R1 (Interleukin 18 receptor 1), IL-2RA (Interleukin 2 receptor, alpha 2), IL-2RG (Interleukin 2 receptor, gamma), IL4-R (Interleukin 4 receptor), IL-6R (Interleukin 6 receptor), IL-21 (Interleukin 21), IL-22 (Interleukin 22), IL-1β (Interleukin 1-beta), TBX21 (T-box 21), TGFBR2 (Transforming growth factor, beta receptor II), TNF (Tumor necrosis factor, TNF-α), TNF-β (LT), TGF-β, FOXP3 (Forkhead box P3), or IL-10RB (Interleukin 10 receptor, beta). Expression of these genes can be evaluated using commercially available services, reagents and/or kits, e.g., the MouseWG-6 v2.0 Expression BeadChip Kit (Illumina, Inc., San Diego, Calif.).

In embodiments, the panel of biomarker mRNA species comprises at least one mRNA species transcribed from a gene encoding a cytokine selected from IL-2, IL-4, IL-5, IL-6, IL-10, IL-13, or IL-17, IL-21, IL-22, IFN-γ, TNF-α (TNF), TNF-β (LT), TGF-β, and IL-1b. In embodiments, the panel of biomarker mRNA species comprises at least one mRNA species transcribed from a gene encoding an activation markers or cytokine receptor selected from CD69, CD25, CD71, CD137, CD154, CD278, CD279, and HLA-DR. In embodiments, the panel of biomarker mRNA species comprises at least one mRNA species transcribed from a gene encoding a chemokine selected from IL-8 (CXCL8), RANTES (CCL5), CCL1, CXCL4, and CXCL7. In embodiments, the panel of biomarker mRNA species comprises at least one mRNA species selected from an mRNA species transcribed from a gene encoding a Th1-associated cytokine, an mRNA species transcribed from a gene encoding a Th2-associated cytokine, an mRNA species transcribed from a gene encoding a Th17-associated cytokine, and an mRNA species transcribed from a gene encoding a $T_{FH}$-associated cytokine. In embodiments, the panel of biomarker mRNA species comprises at least one mRNA species transcribed from a gene encoding a Th1-associated cytokine. In embodiments, the Th1-associated cytokine is IFN-γ, IL-2, IL-10, TNF-α, or CXCL1. In embodiments, the panel of biomarker mRNA species comprises at least one mRNA species transcribed from a gene encoding a Th2-associated cytokine. In embodiments, the Th1-associated cytokine is IL-4, IL-5, IL-10, or IL-13. In embodiments, the panel of biomarker mRNA species comprises at least one mRNA species transcribed from a gene encoding a Th17-associated cytokine. In embodiments, the Th17-associated cytokine is IL-17 or IL-22. In embodiments, the panel of biomarker mRNA species comprises at least one response biomarker mRNA transcribed from a gene encoding a $T_{FH}$-associated cytokine. In embodiments, the $T_{FH}$-associated cytokine is IL-21. In embodiments, the panel of biomarker mRNA species comprises at least one mRNA species transcribed from a gene encoding a key regulatory associated cytokine. In embodiments, key regulatory associated cytokine is selected from IL-10 and TGF-β.

In embodiments, the panel of biomarker mRNA species comprises mRNA species transcribed from genes encoding IL-2, IL-4, IL-5, IL-6, IL-10, IL-13, IL-17, IL-22, IFN-γ, TNF-α, CD-25, and IL1-β. In embodiments, the panel of biomarker mRNA species comprises mRNA species transcribed from genes encoding IL-4, IL-5, IL-13, IL-17, IL-22, TNF-α, CD-25, and IL1-β. In embodiments, the panel of biomarker mRNA species comprises mRNA species transcribed from genes encoding IL-4, IL-13, and TNF-α.

In embodiments, the panel of biomarker mRNA species comprises mRNA species transcribed from genes encoding IL-2, IL-4, IL-5, IL-13, IL-17, IL-22, IFN-γ, or CD25. In embodiments, the panel of biomarker mRNA species comprises mRNA species transcribed from genes encoding IL-4, IL-5, IL-13, IL-17, or CD25. In embodiments, the panel of biomarker mRNA species comprises mRNA species transcribed from genes encoding IL-2, IL-4, IL-5, IL-6, IL-13, IL-17, IL-22, IFN-γ, and TNF-α. In embodiments, the panel of biomarker mRNA species comprises mRNA species transcribed from genes encoding IL-4, IL-5, IL-13, IL-17, IL-22, and TNF-α. In embodiments, the panel of biomarker mRNA species comprises mRNA species transcribed from genes encoding IL-4, IL-5, IL-13, IL-17, and IFN-γ. In embodiments, the panel of biomarker mRNA species comprises mRNA species transcribed from genes encoding IL-4, IL-5, IL-13, and IL-17. In embodiments, the panel of biomarker mRNA species comprises mRNA species transcribed from genes encoding CD25, IL-4, and IL-13. In embodiments, the panel of biomarker mRNA species comprises mRNA species transcribed from genes encoding IL-4 and IL-13.

In embodiments, the mRNA species in the panel of biomarker mRNA species are measured at about 4 to about 6 hours following initiation of incubation (stimulation) of the LN cells with the GA test or reference standard lot.

In embodiments, the mRNA species in the panel of biomarker mRNA species are measured at about 6 hours following initiation of incubation (stimulation) of the LN cells with the GA test or reference standard lot.

In embodiments of the methods of the present invention, the mRNA species in the panel of response biomarker mRNA species are measured before about 24 hours after GA stimulation is initiated. In embodiments of the methods of the present invention, the mRNA species in the panel of response biomarker mRNA species are measured before about 23, about 22, about 21, or about 20 hours after GA stimulation is initiated.

In embodiments of the methods of the invention, the mRNA species in the panel of response biomarker mRNA species are measured at about 4 to about 6 hours following initiation of incubation (stimulation) of the LN cells with the GA test or reference standard lot. In embodiments of the methods of the invention, the GA response biomarker mRNA is measured at about 1 hour to about 24 hours following initiation of incubation of the LN cells with the GA test or reference standard lot. In embodiments, the GA response biomarker mRNA is measured at about 1 hour, at about 1.25 hours, at about 1.5 hours, at about 1.75 hours, at about 2 hours, at about 2.25 hours, at about 2.5 hours, at about 2.75 hours, at about 3 hours, at about 3.25 hours, at about 3.5 hours, at about 3.75 hours, at about 4 hours, at about 4.25 hours, at about 4.5 hours, at about 4.75 hours, at about 5 hours, at about 5.25 hours, at about 5.5 hours, at about 5.75 hours, at about 6 hours, at about 6.25 hours, at about 6.5 hours, at about 6.75 hours, at about 7 hours, at about 7.25 hours, at about 7.5 hours, at about 7.75 hours, at about 8 hours, at about 8.25 hours, at about 8.5 hours, at about 8.75 hours, at about 9 hours, at about 9.25 hours, at about 9.5 hours, at about 9.75 hours, at about 10 hours, at about 10.25 hours, at about 10.5 hours, at about 10.75 hours, at about 11 hours, at about 11.25 hours, at about 11.5 hours, at about 11.75 hours, at about 12 hours, at about 12.5 hours, at about 13 hours, at about 13.5 hours, at about 14 hours, at about 14.5 hours, at about 15 hours, at about 15.5 hours, at about 16 hours, at about 17 hours, at about 18 hours, at about 19 hours, at about 20 hours, at about 21 hours, at about 22 hours, at about 23, or at about 24 hours following initiation of incubation (stimulation) of the LN cells with the GA test or reference standard lot.

In embodiments, the mRNA species in the panel of response biomarker mRNA species are measured at about 2 hours to about 16 hours, about 2 hours to about 15 hours about 2 hours to about 14 hours, about 2 hours to about 13 hours, about 2 hours to about 12 hours, about 2 hours to about 11 hours, about 2 hours to about 10 hours, about 2 hours to about 9 hours, about 2 hours to about 8 hours, about 2 hours to about 7 hours, about 2 hours to about 6 hours, about 2.5 hours to about 16 hours, about 2.5 hours to about 15 hours about 2.5 hours to about 14 hours, about 2.5 hours to about 13 hours, about 2.5 hours to about 12 hours, about 2.5 hours to about 11 hours, about 2.5 hours to about 10 hours, about 2.5 hours to about 9 hours, about 2.5 hours to about 8 hours, about 2.5 hours to about 7 hours, about 2.5 hours to about 6 hours, about 2.5 hours to about 5.5 hours, about 2.5 hours to about 5 hours, about 2.5 hours to about 4 hours, about 3 hours to about 16 hours, about 3 hours to about 15 hours about 3 hours to about 14 hours, about 3 hours to about 13 hours, about 3 hours to about 12 hours, about 3 hours to about 11 hours, about 3 hours to about 10 hours, about 3 hours to about 9 hours, about 3 hours to about 8 hours, about 3 hours to about 7 hours, about 3 hours to about 6 hours, about 3 hours to about 5.5 hours, about 3 hours to about 5 hours, about 3 hours to about 4 hours, about 3.5 hours to about 16 hours, about 3.5 hours to about 15 hours about 3.5 hours to about 14 hours, about 3.5 hours to about 13 hours, about 3.5 hours to about 12 hours, about 3.5 hours to about 11 hours, about 3.5 hours to about 10 hours, about 3.5 hours to about 9 hours, about 3.5 hours to about 8 hours, about 3.5 hours to about 7 hours, about 3.5 hours to about 6 hours, about 3.5 hours to about 5.5 hours, about 3.5 hours to about 5 hours, about 4 hours to about 16 hours, about 4 hours to about 15 hours, about 4 hours to about 14 hours, about 4 hours to about 13 hours, about 4 hours to about 12 hours, about 4 hours to about 11 hours, about 4 hours to about 10 hours, about 4 hours to about 9 hours, about 4 hours to about 8 hours, about 4 hours to about 7 hours, about 4 hours to about 6 hours, about 4 hours to about 5.5 hours, about 5 hours to about 16 hours, about 5 hours to about 15 hours, about 5 hours to about 14 hours, about 5 hours to about 13 hours, about 5 hours to about 12 hours, about 5 hours to about 11 hours, about 5 hours to about 10 hours, about 5 hours to about 9 hours, about 5 hours to about 8 hours, about 5 hours to about 7 hours, about 5 hours to about 6 hours, about 6 hours to about 16 hours, about 6 hours to about 15 hours, about 6 hours to about 14 hours, about 6 hours to about 13 hours, about 6 hours to about 12 hours, about 6 hours to about 11 hours, about 6 hours to about 10 hours, about 6 hours to about 9 hours, about 6 hours to about 8 hours, about 6 hours to about 7 hours, about 7 hours to about 16 hours, about 7 hours to about 15 hours, about 7 hours to about 14 hours, about 7 hours to about 13 hours, about 7 hours to about 12 hours, about 7 hours to about 11 hours, about 7 hours to about 10 hours, about 7 hours to about 9 hours, about 7 hours to about 8 hours, about 2 hours to about 24 hours, about 2 hours to about 20 hours, about 2 hours to about 18 hours, about 2 hours to about 16 hours, about 4 hours to about 24 hours, about 4 hours to about 20 hours, about 4 hours to about 18 hours, about 4 hours to about 16 hours, about 6 hours to about 24 hours, about 6 hours to about 20 hours, about 6 hours to about 18 hours, about 6 hours to about 16 hours, about 8 hours to about 24 hours, about 8 hours to about 20 hours, about 8 hours to about 18 hours, or about 8 hours to about 16 hours, following initiation of incubation (stimulation) of the LN cells with the GA test or reference standard lot.

In embodiments, the LN cells are treated with an inhibitor of protein synthesis, e.g., cycloheximide, after or upon stimulation with GA.

EXAMPLES

Example I. Development of a Glatiramer Acetate Potency Assay that Measures Response Biomarker mRNA in Lymph Node Cells from Glatiramer Acetate-Immunized Mice Following Challenge with Glatiramer Acetate A potency assay for glatiramer acetate (GA) that measures response biomarker mRNA expression levels following GA challenge of T-cells from a (SJL/J×BALB/C)F1 mouse strain immunized with GA was developed. LN cells obtained from the immunized mice demonstrated substantial increases in cytokine mRNA levels in response to GA stimulation as early as 2 hours, and certainly by 4 hours, after the stimulation.

Assay Development

Three experiments were carried out to evaluate different timepoints, response biomarker mRNAs, assay format, and reagents for use in the potency assay. Table 1 shows the experiment design for three studies, and the immunizations carried out in each.

TABLE 1

Immunizations for Evaluation of Response Biomarker mRNA in (SJL/J × BALB/C)F1 Mouse Strain

| Experiment ID | Group | Dose Route | # Animals/ Gender | Immunization (CFA+) | Dose of GA/mouse (Day 0) |
|---|---|---|---|---|---|
| Experiment 1 Time Course & Cytokines | 1A | Inject into four footpads | 6/F | GA | 250 µg |
| Experiment 2 Plate Format and RNA Isolation Kit Comparison | 2A | Inject into four footpads | 6/F | GA | 250 µg |
| Experiment 3 Concentration | 3A | Inject into four footpads | 6/F | GA | 250 µg |

TABLE 1-continued

Immunizations for Evaluation of Response Biomarker mRNA in (SJL/J × BALB/C)F1 Mouse Strain

| Experiment ID | Group | Dose Route | # Animals/ Gender | Immunization (CFA+) | Dose of GA/mouse (Day 0) |
|---|---|---|---|---|---|
| Study | 4A | Inject into four footpads | 5/F | Mannitol | 0 µg |

GA = Glatiramer Acetate (GMA, Mylan Pharmaceuticals, Inc.);
CFA = Complete Freund's Adjuvant For each of the three experiments summarized in Table 1, female (SJL/J×BALB/C) F1 hybrid (Jackson Laboratory) mice were immunized by footpad injection with either 250 µg GMA (Mylan Pharmaceuticals, Inc.) and CFA (Sigma Aldrich), or Mannitol and CFA (as a negative control). The GA solution was diluted to 5 mg/mL with Dulbecco's Phosphate-buffered saline. A dose solution was then prepared by mixing the diluted GA solution (5 mg/mL) and CFA (1:1) until well-emulsified. Each mouse received a total injection volume of 0.1 mL (250 µg GA). Animals were immunized on Day 0. Immunized animals were sacrificed via cervical dislocation on Day 10 following immunization. Lymph nodes in the axillary and popliteal regions were removed aseptically in a purifier clean bench, and transferred into a sterile petri dish containing about 5 mL of sterile RPMI 1640 medium. The LN were washed 3 times with ~5 mL of RPMI medium, and the LN cells isolated by pressing the LN with a syringe plunger. The cell suspension was transferred to a sterile 50 mL conical tube, washed in about 40 mL of RPMI medium by centrifuging at about 200×g for 10 minutes at about 4° C., and re-suspended in RPMI 1640 medium for cell counting. The cell suspension was centrifuged at about 200×g for 10 minutes at about 4° C. and re-suspended in ice cold enriched DCCM-1 medium. The LN cells ($2.5 \times 10^6$ cells/cm$^2$) were plated in the wells of a 48-well tissue culture plate and stimulated with GA or controls.

After incubation at about 37° C. in a humidified $CO_2$ incubator for the indicated time, total RNA was isolated from the treated cells using the RNeasy Mini Kit (Qiagen, Cat. #74104). Cells were lysed in RNA lysis buffer, transferred to Qiagen spin columns, washed, and the RNA eluted with DEPC-treated water from the column. cDNA was synthesized from each RNA sample using the High Capacity cDNA Reverse Transcription Kit (Applied Biosystems, Cat. #4368814). The PCR reactions were carried out using Taq-Man Universal PCR Master Mix (Applied Biosystems, Cat. #4304437) and specific primers/probe for the target cytokine and reference internal controls. Primers/probes for mouse cytokines IL-2 (Cat. #4331182; ID Mm00434256_m1), IL-4 (Cat. #4331182; ID Mm00445259_m1), IL-5 (Cat. #4331182; ID Mm00439646_m1), IFN-γ (Cat. #4331182; ID Mm01168134_m1), IL-10 (ID Mm00439614_m1), and TNF-α (Mm00443260_g1) were obtained from Life Technologies. Expression of cytokine mRNA was quantitatively analyzed using a Real-Time PCR system (7500, Applied Biosystems).

The stimulations and the mRNA expression results used in Experiment 1 (Group 1A mice) are shown in Tables 2-5. The fold-change vs control for each cytokine was calculated by 1) normalizing the level of the mouse cytokine amplicon to an internal probe for GAPDH from the same samples, and 2) dividing mRNA expression level of the cytokine by the level observed in a DCCM1 (medium) control. (DCCM1 from Beit Haemek Ltd.; Cat. No. 05 010 1A). There was no MBP treatment for the 2-hour groups. (MBP from Bachem; Cat No. H-1964.0001) For each evaluation time DCCM1 was studied and compared, i.e. 2 hours represents 2 hours with DCCM1, 4 hours=4 hours, etc., and served as representative control for each timepoint.

Table 2 shows the murine IL-2 mRNA levels detected in the LN cells at 2, 4, 6, and 24 hours following the indicated stimulation. About a 5.3-fold to about a 20.8-fold increase in mIL-2 mRNA expression relative to the DCCM1 negative control was observed at these timepoints, with the greatest increase at 6 hours. By 24 hours the increase had dropped to below that observed at 2 hours.

TABLE 2

Evaluation of mIL-2 Expression in a Time Course Study (Experiment 1)

| Hours Post Stimulation | Stimulation | mIL-2 mRNA Level (fold change vs control) | SD | n |
|---|---|---|---|---|
| 2 hour | DCCM1 | 1.0 | 0.1 | 3 |
|  | GA-10 µg/mL | 5.3 | 0.8 | 3 |
|  | ConA-2.5 µg/mL | 183.4 | 14.6 | 3 |
| 4 hour | DCCM1 | 1.0 | 0.0 | 3 |
|  | MBP-10 µg/mL | 1.0 | 0.1 | 3 |
|  | GA-10 µg/mL | 12.2 | 0.6 | 3 |
|  | ConA-2.5 µg/mL | 131.5 | 9.3 | 3 |
| 6 hour | DCCM1 | 1.0 | NA | 2 |
|  | MBP-10 µg/mL | 0.3 | NA | 2 |
|  | GA-10 µg/mL | 20.8 | 2.9 | 3 |
|  | ConA-2.5 µg/mL | 105.0 | 12.1 | 3 |
| 24 hour | DCCM1 | 1.1 | 0.5 | 3 |
|  | MBP-10 µg/mL | 0.6 | 0.2 | 3 |
|  | GA-10 µg/mL | 3.6 | 0.9 | 3 |
|  | ConA-2.5 µg/mL | 16.2 | 1.9 | 3 |

Abbreviations:
MBP = Myelin Basic Protein (a negative control);
ConA = Concanavalin A (a positive control);
GA = Glatiramer acetate (GMA, Mylan Pharmaceuticals, Inc.);
SD = Standard deviation;
NA = Not applicable (n < 3).

Table 3 shows the murine IL-4 mRNA levels detected in the LN cells at 2, 4, 6, and 24 hours following the indicated stimulation. About a 10-fold to about a 16.5-fold increase in mIL-4 mRNA expression relative to the DCCM1 control was observed at these timepoints, with the greatest increase observed at 6 hours post-stimulation.

TABLE 3

Evaluation of mIL-4 Expression in a Time Course Study

| Hours Post Stimulation | Stimulation | mIL-4 mRNA Level (fold change vs control) | SD | n |
|---|---|---|---|---|
| 2 hour | DCCM1 | 1.0 | 0.2 | 3 |
|  | GA-10 µg/mL | 10.0 | 1.1 | 3 |
|  | ConA-2.5 µg/mL | 35.7 | 0.6 | 3 |
| 4 hour | DCCM1 | 1.0 | 0.1 | 3 |
|  | MBP-10 µg/mL | 0.8 | 0.2 | 3 |
|  | GA-10 µg/mL | 10.0 | 1.0 | 3 |
|  | ConA-2.5 µg/mL | 47.6 | 3.4 | 3 |
| 6 hour | DCCM1 | 1.0 | 0.2 | 3 |
|  | MBP-10 µg/mL | 0.6 | NA | 2 |
|  | GA-10 µg/mL | 16.5 | 1.3 | 3 |
|  | ConA-2.5 µg/mL | 52.2 | 6.2 | 3 |
| 24 hour | DCCM1 | 1.0 | 0.3 | 3 |
|  | MBP-10 µg/mL | 1.1 | NA | 2 |
|  | GA-10 µg/mL | 14.1 | 1.3 | 3 |
|  | ConA-2.5 µg/mL | 6.1 | 1.3 | 3 |

Abbreviations:
MBP = Myelin Basic Protein (a negative control);
ConA = Concanavalin A (a positive control);
GA = Glatiramer acetate (GMA, Mylan Pharmaceuticals, Inc.);
SD = Standard deviation;
NA = Not applicable (n < 3).

Table 4 shows the murine IL-5 mRNA levels detected in the LN cells at 2, 4, 6, and 24 hours following the indicated stimulation. About a 1.6-fold to about a 5.1-fold increase in mIL-5 mRNA expression relative to the DCCM1 control was observed at these timepoints, with the greatest increase observed at 6 hours post-stimulation. By 24 hours the increase had dropped to 1.9, nearly that observed at 2 hours.

TABLE 4

Evaluation of mIL-5 Expression in a Time Course Study

| Hours Post Stimulation | Stimulation | mIL-5 mRNA Level (fold change vs control) | SD | n |
|---|---|---|---|---|
| 2 hour | DCCM1 | 1.0 | 0.0 | 3 |
|  | GA-10 µg/mL | 1.6 | 0.4 | 3 |
|  | ConA-2.5 µg/mL | 3.6 | 0.3 | 3 |
| 4 hour | DCCM1 | 1.0 | 0.4 | 3 |
|  | MBP-10 µg/mL | 0.8 | 0.2 | 3 |
|  | GA-10 µg/mL | 4.8 | 0.7 | 3 |
|  | ConA-2.5 µg/mL | 17.1 | 1.1 | 3 |
| 6 hour | DCCM1 | 1.0 | 0.1 | 3 |
|  | MBP-10 µg/mL | 0.2 | NA | 2 |
|  | GA-10 µg/mL | 5.1 | 0.4 | 3 |
|  | ConA-2.5 µg/mL | 13.1 | 0.6 | 3 |
| 24 hour | DCCM1 | 1.0 | 0.3 | 3 |
|  | MBP-10 µg/mL | 0.8 | 0.1 | 3 |
|  | GA-10 µg/mL | 1.9 | 0.4 | 3 |
|  | ConA-2.5 µg/mL | 0.5 | NA | 2 |

Abbreviations:
MBP = Myelin Basic Protein (a negative control);
ConA = Concanavalin A (a positive control);
GA = Glatiramer acetate (GMA, Mylan Pharmaceuticals, Inc.);
SD = Standard deviation;
NA = Not applicable (n < 3).

Table 5 shows the murine mIFN-γ mRNA levels detected in the LN cells at 2, 4, 6, and 24 hours following the indicated stimulation. A 1.3-fold to about a 4.6-fold increase in mIFN-γ expression relative to the DCCM1 control was observed at these timepoints. After 6 hours the magnitude of increase was observed to level off.

Levels of mRNA expression from mIL-10 and mTNF-α also were measured using total RNA isolated from samples in a time course study. Results showed no significant increase in mRNA levels in LN cells after stimulation with GA (data not shown). The fold-changes of mRNA levels in LN cells treated with GA compared to those in mock-treated control (DCCM1) LN cells at both 6 and 24 hours post-stimulation were about ≤1.

TABLE 5

Evaluation of mIFN-γ Expression in a Time Course Study

| Hours Post Stimulation | Stimulation | mIFN-γ mRNA Level (fold change vs control) | SD | n |
|---|---|---|---|---|
| 2 hour | DCCM1 | 1.0 | 0.1 | 3 |
|  | GA-10 µg/mL | 1.3 | 0.4 | 3 |
|  | ConA-2.5 µg/mL | 40.9 | 10.2 | 3 |
| 4 hour | DCCM1 | 1.0 | 0.2 | 3 |
|  | MBP-10 µg/mL | 0.8 | 0.1 | 3 |
|  | GA-10 µg/mL | 2.1 | 0.3 | 3 |
|  | ConA-2.5 µg/mL | 49.3 | 10.2 | 3 |
| 6 hour | DCCM1 | 1.0 | 0.2 | 3 |
|  | MBP-10 µg/mL | 0.2 | 0.1 | 3 |
|  | GA-10 µg/mL | 4.6 | 1.1 | 3 |
|  | ConA-2.5 µg/mL | 18.2 | 2.6 | 3 |
| 24 hour | DCCM1 | 1.0 | NA | 2 |
|  | MBP-10 µg/mL | 0.6 | 0.2 | 3 |
|  | GA-10 µg/mL | 4.6 | NA | 2 |
|  | ConA-2.5 µg/mL | 0.4 | NA | 2 |

Abbreviations:
MBP = Myelin Basic Protein (a negative control);
ConA = Concanavalin A (a positive control);
GA = Glatiramer acetate (GMA, Mylan Pharmaceuticals, Inc.);
SD = Standard deviation;
NA = Not applicable (n < 3).

In Experiment 2 (using Group 2A mice; see Table 1 for design), carried out under similar conditions as used for Experiment 1, 46-well and 98-well plate formats were compared (data not shown). The levels of mIL-2 and mIL-4 mRNA were measured in the 46-well plate format (RNeasy Mini Kit, Qiagen), and the 98-well plate format (SV 96 Total RNA Isolation System, Promega) at both 4 and 6 hours post-stimulation with GA (10 µg/ml), MBP (10 µg/ml), and ConA (2.5 µg/ml) and compared with a DCCM1 control. IL-2 expression at 4 hours in the GA-treated samples was observed at 16.3 and 29.5-fold that of control in the 48-well and 96-well formats, respectively, and at 6 hours was 21.0 and 41.7 fold that of control in the 48-well and 96-well formats, respectively. IL-4 expression at 4 hours in the GA-treated samples was observed at 8.5 and 8.0-fold that of control in the 48-well and 96-well formats, respectively, and at 6 hours was 14.0 and 16.5-fold that of control in the 48-well and 96-well formats, respectively.

In Experiment 3 (Groups 3A and 4A mice; see Table 1 for design), mIL-2 mRNA was measured in LN cells stimulated with a range of concentrations of GA. Table 6 shows the results of Experiment 3. This study included samples stimulated with a second lot of GA, Cop (Copaxone, Teva Pharmaceuticals USA, Inc., released commercial product). The Cop sample sets allowed comparison of the effect of immunizing and stimulating with different lots of GA on cytokine production.

TABLE 6 mIL-2 mRNA Expression Levels in Primary LN Cells in Response to Stimulation with Different Concentrations of GA or Copaxone (Experiment 3)

| Group | Immunization-Stimulation-Stimulation Conc. (µg/mL) | mIL-2 mRNA Level (fold change vs control) | SD | n |
|---|---|---|---|---|
| Group 3A | GA-GA-1 | 9.7 | 1.5 | 3 |
| (GA + CFA) | GA-GA-2.5 | 20.2 | 3.9 | 3 |
| | GA-GA-5 | 22.6 | 3.4 | 3 |
| | GA-GA-10 | 26.1 | 8.1 | 3 |
| | GA-GA-15 | 27.3 | 6.5 | 3 |
| | GA-GA-25 | 34.7 | 8.3 | 3 |
| | GA-Cop-1 | 10.1 | 2.1 | 3 |
| | GA-Cop-2.5 | 20.0 | 3.7 | 3 |
| | GA-Cop-5 | 22.7 | 1.9 | 3 |
| | GA-Cop-10 | 27.2 | 1.8 | 3 |
| | GA-Cop-15 | 26.0 | 1.9 | 3 |
| | GA-Cop-25 | 30.0 | 4.7 | 3 |
| | DCCM1-0 | 1.0 | 0.3 | 3 |
| | MBP-10 | 0.9 | 0.5 | 3 |
| | ConA-2.5 | 111.0 | 21.4 | 3 |
| Group 4A | Man-GA-5 | 3.0 | 0.5 | 3 |
| (Mannitol + CFA) | Man-GA-10 | 1.6 | 0.3 | 3 |
| | Man-GA-25 | 1.7 | 0.2 | 3 |
| | Man-Cop-5 | 1.0 | 0.4 | 3 |
| | Man-Cop-10 | 1.3 | 0.3 | 3 |
| | Man-GA-25 | 1.5 | 0.3 | 3 |
| | DCCM1-0* | 1.0 | 0.2 | 3 |
| | MBP-10* | 1.5 | 0.7 | 3 |
| | ConA-2.5* | 91.4 | 3.8 | 3 |

Abbreviations: MBP = Myelin Basic Protein (a negative control); ConA = Concanavalin A (a positive control); GA = Glatiramer acetate (GMA, Mylan Pharmaceuticals, Inc.); Cop = Copaxone; SD = Standard deviation.
*Animals not immunized.

Table 6 shows the mIL-2 mRNA levels detected in the LN cells 6 hours following the indicated stimulation. As before, the fold change vs control was calculated by 1) normalizing the level of the mouse cytokine amplicon to an internal probe for GAPDH from the same samples, and 2) dividing mRNA expression level of the cytokine by the level observed in response to GA stimulation of the DCCM1 control. For Experiment 3, a 96-well plate format was used, and RNA isolation was carried out using an SV 96 Total RNA Isolation System (Promega). Immunization of Groups 3A and 4A are described in Table 1. FIGS. 1A and 1B are graphs comparing the expression levels of mIL-2 mRNA detected in Experiment 3 (described in Table 6). mIL-2 mRNA was stimulated comparably by Cop and GA (Mylan GMA). Y-axis: linear mRNA fold-changes of mIL-2. X-axis: log Cop and GA (Mylan GMA) concentration values. The best fit for the data set was performed using the logarithmic model. The slope values were 6.779 and 5.6834 for GA (Mylan GMA) and Cop treated samples, respectively, when the regression was performed using all concentrations. The slope values were 6.214 and 5.962 for GA (Mylan GMA) and Cop treated samples, respectively, when the regression was performed using 5 concentrations (1 to 15 µg/mL). The graphs in FIGS. 1A and 1B show that IL-2 mRNA from treated cells increased in a dose-dependent fashion with stimulation by increasing concentrations of either a first lot or a second lot of GA, when the first lot of GA was used for immunization.

Other experiments demonstrated that secreted IL-2 from treated cells increased in dose-dependent fashion with increasing concentrations of a first lot of GA (GMA, Mylan Pharmaceuticals, Inc.) and a second lot of GA (Copaxone, Teva Pharmaceuticals USA, Inc.) (data not shown). This dose-dependent response was consistent for both test and reference compounds independent of whether Copaxone® or Mylan GMA was used as the immunizing antigen.

In a second series of experiments, expression of mIL-2, mIL-4, mIL-5, mIL-10 and mIFN-γ mRNA was evaluated in LN cells at four and six hours post-stimulation with 10 µg/mL GA. The results indicate that GA-stimulation of LN cells from mice immunized with GA cause a specific increase in cytokine mRNA levels. The experiment design is shown in Table 7.

TABLE 7

Immunizations and Stimulations for Evaluation of Response Biomarker mRNA in (SJL/J × BALB/C)F1 Lymph Node Cells

| Group | Immunization | Stimulation | Concentration of Stimulation Reagent (µg/mL) |
|---|---|---|---|
| Group 1B | GA + CFA | DCCM1 | NA |
| | | GA | 10 |
| | | MBP | 10 |
| | | ConA | 2.5 |
| Group 2B | Mannitol + CFA | DCCM1 | NA |
| | | GA | 10 |
| | | MBP | 10 |
| | | ConA | 2.5 |

NA = Not applicable; GA = Glatiramer acetate; MBP = Myelin Basic Protein (a negative control); ConA = Concanavalin A (a positive control)

Group 1B animals were female (SJL/J×BALB/C) F1 hybrid (Jackson Laboratory) mice immunized by footpad injection with either 250 µg GA and CFA, or Mannitol and CFA (as a negative control). A dose solution was prepared by mixing a diluted GA solution (5 mg/mL) and CFA (1:1). Each mouse received a total injection volume of 1 mL (250 µg GA). Animals were immunized on Day 0. Immunized animals were sacrificed via cervical dislocation on Day 10 following immunization. Lymph nodes from immunized mice were removed and isolated. LN cells ($2.5 \times 10^6$ cells/cm$^2$) were plated in the wells of a 48-well tissue culture plate for stimulation with GA.

Total RNA was isolated from the treated cells using the RNeasy Mini Kit (Qiagen, Cat. #74104). Cells were lysed in RNA lysis buffer, transferred to Qiagen spin columns, washed, and the RNA eluted with DEPC-treated water from the column. cDNA was synthesized from each RNA sample using the High Capacity cDNA Reverse Transcription Kit (Applied Biosystems, Cat. #4368814). The PCR reaction was carried out using TaqMan Universal PCR Master Mix (Applied Biosystems, Cat. #4304437) and specific primers/probe for the target cytokine and reference internal control.

Expression of cytokine mRNA was quantitatively analyzed 4 and 6 hours after using a Real-Time PCR system (7500, Applied Biosystems).

Tables 8-12 show the stimulations used for the Group 1B mice (described in Table 7), and the mRNA expression results obtained. The fold change vs control for each cytokine was calculated by 1) normalizing the level of the mouse cytokine amplicon to an internal probe for 18S RNA or GAPDH mRNA from the same samples, and 2) dividing mRNA expression level of the cytokine by the level observed in response to a DCCM1 (culture medium) control normalized to the same housekeeping gene mRNA.

Table 8 shows the mIL-2 mRNA levels detected in the LN cells at 4 and 6 hours following the indicated stimulation. The mIL-2 mRNA level in GA-stimulated cells from mice immunized with GA (Group 1B) increased at least 10-fold in comparison to the DCCM-1-stimulated control at these timepoints. GA-stimulation did not result in a substantial increase of the mIL-2 mRNA detected in cells from the control mice immunized with mannitol+CFA (Group 2B). Furthermore, expression of mIL-2 mRNA substantially increased in the ConA positive control cells, but did not increase in the MBP negative control cells. A greater increase in mIL-2 mRNA expression was observed in the GA-stimulated cells at 4 hours than at 6 hours. The internal control (reference gene) was 18S rRNA.

TABLE 8 mIL-2 mRNA Expression in Primary LN Cells in Response to GA Stimulation

| Group (Immunization) | Stimulation | mIL-2 mRNA Level (fold change vs control) | SD | n |
|---|---|---|---|---|
| A. 4 hours post-stimulation ||||||
| Group 1B (GA + CFA) | DCCM-1 | 1.2 | 0.6 | 3 |
|  | MBP-10 µg/mL | 0.5 | 0.2 | 3 |
|  | GA-10 µg/mL | 16.7 | 5.5 | 3 |
|  | ConA-2.5 µg/mL | 256.3 | 82.2 | 3 |
| Group 2B (Mannitol + CFA) | DCCM-1 | 1.0 | 0.1 | 3 |
|  | MBP-10 µg/mL | 0.4 | 0.1 | 3 |
|  | GA-10 µg/mL | 1.8 | 0.6 | 3 |
|  | ConA-2.5 µg/mL | 517.9 | 80.4 | 3 |
| B. 6 hours post-stimulation ||||||
| Group 1B (GA + CFA) | DCCM-1 | 1.2 | 0.9 | 3 |
|  | MBP-10 µg/mL | 0.3 | NA | 2 |
|  | GA-10 µg/mL | 10.2 | 0.7 | 3 |
|  | ConA-2.5 µg/mL | 54.3 | NA | 2 |
| Group 2B (Mannitol + CFA) | DCCM-1 | 1.0 | NA | 2 |
|  | MBP-10 µg/mL | 0.5 | NA | 2 |
|  | GA-10 µg/mL | 1.4 | 0.5 | 3 |
|  | ConA-2.5 µg/mL | 277.9 | NA | 2 |

Abbreviations: MBP = Myelin Basic Protein (a negative control); ConA = Concanavalin A (a positive control); GA = Glatiramer acetate; SD = Standard deviation; NA = Not applicable (n < 3).

Table 9 shows the mIL-4 mRNA levels detected in the LN cells at 4 and 6 hours following the indicated stimulation. The mIL-4 mRNA level in GA-stimulated cells from mice immunized with GA (Group 1B) increased at least 8-fold in comparison to the DCCM-1-stimulated control at these timepoints. GA-stimulation did not result in a substantial increase of the mIL-4 mRNA detected in cells from the control mice immunized with mannitol+CFA (Group 2B). Furthermore, expression of mIL-4 mRNA substantially increased in the ConA positive control cells, but did not increase in the MBP negative control cells. The internal control (reference gene) was 18S rRNA.

TABLE 9 mIL-4 mRNA Expression in Primary LN Cells in Response to GA Stimulation

| Group (Immunization) | Stimulation | mIL-4 mRNA (fold change vs control) | SD | n |
|---|---|---|---|---|
| A. 4 hours post-stimulation ||||||
| Group 1B (GA + CFA) | DCCM-1 | 1.0 | 0.3 | 3 |
|  | MBP-10 µg/mL | 0.5 | 0.1 | 3 |
|  | GA-10 µg/mL | 8.2 | 0.7 | 3 |
|  | ConA-2.5 µg/mL | 27.1 | 0.4 | 3 |
| Group 2B (Mannitol + CFA) | DCCM-1 | 1.1 | 0.4 | 3 |
|  | MBP-10 µg/mL | 1.4 | 0.8 | 3 |
|  | GA-10 µg/mL | 2.2 | 1.0 | 3 |
|  | ConA-2.5 µg/mL | 37.3 | 12.3 | 3 |
| B. 6 hours post-stimulation ||||||
| Group 1B (GA + CFA) | DCCM-1 | 1.1 | 0.5 | 3 |
|  | MBP-10 µg/mL | 0.3 | 0.0 | 2 |
|  | GA-10 µg/mL | 9.2 | 1.8 | 3 |
|  | ConA-2.5 µg/mL | 12.8 | 0.6 | 2 |
| Group 2B (Mannitol + CFA) | DCCM-1 | 1.0 | 0.4 | 2 |
|  | MBP-10 µg/mL | 0.8 | 0.0 | 2 |
|  | GA-10 µg/mL | 1.1 | 0.3 | 3 |
|  | ConA-2.5 µg/mL | 56.2 | 36.2 | 2 |

Abbreviations: MBP = Myelin Basic Protein (a negative control); ConA = Concanavalin A (a positive control); GA = Glatiramer acetate; SD = Standard deviation; NA = Not applicable (n < 3).

Table 10 shows the mIL-5 mRNA levels detected in the LN cells at 4 and 6 hours following the indicated stimulation. The mIL-5 mRNA level in GA-stimulated cells from mice immunized with GA (Group 1B) increased at least 4-fold in comparison to the DCCM-1-stimulated control at these timepoints. GA-stimulation did not result in a substantial increase of the mIL-5 mRNA detected in cells from the control mice immunized with mannitol+CFA (Group 2B). Furthermore, expression of mIL-5 mRNA substantially increased in the ConA positive control cells, but did not increase in the MBP negative control cells. Data in this experiment were not normalized to a reference gene.

TABLE 10 mIL-5 mRNA Expression in Primary LN Cells in Response to GA Stimulation

| Group (Immunization) | Stimulation | mIL-5 mRNA (fold change vs control) | SD | n |
|---|---|---|---|---|
| A. 4 hours post-stimulation ||||||
| Group 1B (GA + CFA) | DCCM-1 | 1.0 | 0.1 | 3 |
|  | MBP-10 µg/mL | 1.4 | 0.0 | 3 |
|  | GA-10 µg/mL | 4.0 | 0.9 | 3 |
|  | ConA-2.5 µg/mL | 20.4 | 2.0 | 3 |
| Group 2B (Mannitol + CFA) | DCCM-1 | 1.0 | 0.1 | 3 |
|  | MBP-10 µg/mL | 1.1 | 0.2 | 3 |
|  | GA-10 µg/mL | 1.0 | 0.1 | 3 |
|  | ConA-2.5 µg/mL | 16.6 | 0.7 | 3 |
| B. 6 hours post-stimulation ||||||
| Group 1B (GA + CFA) | DCCM-1 | 1.0 | 0.1 | 3 |
|  | MBP-10 µg/mL | 0.9 | 0.3 | 3 |
|  | GA-10 µg/mL | 4.3 | 0.5 | 3 |
|  | ConA-2.5 µg/mL | 26.7 | 2.9 | 3 |
| Group 2B (Mannitol + CFA) | DCCM-1 | 1.0 | 0.1 | 3 |
|  | MBP-10 µg/mL | 1.1 | 0.3 | 2 |
|  | GA-10 µg/mL | 1.2 | 0.1 | 3 |
|  | ConA-2.5 µg/mL | 36.5 | 3.2 | 3 |

Abbreviations: MBP = Myelin Basic Protein (a negative control); ConA = Concanavalin A (a positive control); GA = Glatiramer acetate; SD = Standard deviation; NA = Not applicable (n < 3).

Table 11 shows the mIL-10 mRNA levels detected in the LN cells at 4 and 6 hours following the indicated stimulation. The mIL-10 mRNA level in GA-stimulated cells from mice immunized with GA (Group 1B) did not increase substantially in comparison to the DCCM-1-stimulated control at these timepoints. The internal control (reference gene) was GAPDH.

TABLE 11 mIL-10 mRNA Expression in Primary LN Cells in Response to GA Stimulation

| Group (Immunization) | Stimulation | mIL-10 mRNA (fold change vs control) | SD | n |
|---|---|---|---|---|
| A. 4 hours post-stimulation | | | | |
| Group 1B (GA + CFA) | DCCM-1 | 1.0 | 0.3 | 3 |
| | MBP-10 µg/mL | 1.0 | 0.2 | 3 |
| | GA-10 µg/mL | 1.7 | 0.1 | 3 |
| | ConA-2.5 µg/mL | 2.3 | 0.5 | 3 |
| Group 2B (Mannitol + CFA) | DCCM-1 | 1.0 | 0.3 | 3 |
| | MBP-10 µg/mL | 1.0 | 0.1 | 3 |
| | GA-10 µg/mL | 1.4 | 0.8 | 3 |
| | ConA-2.5 µg/mL | 1.6 | 0.4 | 3 |
| B. 6 hours post-stimulation | | | | |
| Group 1B (GA + CFA) | DCCM-1 | 1.2 | 0.8 | 3 |
| | MBP-10 µg/mL | 0.6 | 0.4 | 3 |
| | GA-10 µg/mL | 1.2 | 0.6 | 3 |
| | ConA-2.5 µg/mL | 1.2 | 0.8 | 3 |
| Group 2B (Mannitol + CFA) | DCCM-1 | 1.1 | 0.7 | 3 |
| | MBP-10 µg/mL | 0.5 | 0.0 | 2 |
| | GA-10 µg/mL | 0.9 | 0.5 | 3 |
| | ConA-2.5 µg/mL | 3.1 | 2.5 | 2 |

Abbreviations: MBP = Myelin Basic Protein (a negative control); ConA = Concanavalin A (a positive control); GA = Glatiramer acetate; SD = Standard deviation; NA = Not applicable (n < 3).

Table 12 shows the mIFN-γ mRNA levels detected in the LN cells at 4 and 6 hours following the indicated stimulation. The mIFN-γ mRNA level in GA-stimulated cells from mice immunized with GA (Group 1B) increased at least about 2-fold and as much as about 7-fold in comparison to the DCCM-1-stimulated control at these timepoints. GA-stimulation did not result in a substantial increase of the mIFN-γ mRNA detected in cells from the control mice immunized with mannitol+CFA (Group 2B). Furthermore, expression of mIFN-γ mRNA increased in the ConA positive control cells, but did not increase in the MBP negative control cells. The internal control (reference gene) was GAPDH.

TABLE 12 mIFN-γ mRNA Expression in Primary LN Cells 4 and 6 Hours after GA Stimulation

| Group (Immunization) | Stimulation | mIFN-γ mRNA Level (fold change vs control) | SD | n |
|---|---|---|---|---|
| A. 4 hours post-stimulation | | | | |
| Group 1B (GA + CFA) | DCCM1 | 1.4 | 1.3 | 2 |
| | MBP-10 µg/mL | 0.9 | 0.3 | 2 |
| | GA-10 µg/mL | 7.0 | 0.5 | 2 |
| | ConA-2.5 µg/mL | 29.5 | 16.1 | 2 |
| Group 2B (Mannitol + CFA) | DCCM1 | 1.0 | 0.1 | 3 |
| | MBP-10 µg/mL | 1.1 | 0.4 | 3 |
| | GA-10 µg/mL | 1.2 | 0.4 | 3 |
| | ConA-2.5 µg/mL | 15.5 | 15.0 | 3 |
| B. 6 hours post-stimulation | | | | |
| Group 1B (GA + CFA) | DCCM1 | 1.5 | 1.6 | 2 |
| | MBP-10 µg/mL | 0.6 | 0.2 | 2 |
| | GA-10 µg/mL | 2.4 | 0.9 | 2 |
| | ConA-2.5 µg/mL | 3.0 | 2.5 | 2 |
| Group 2B (Mannitol + CFA) | DCCM1 | 1.1 | 0.6 | 3 |
| | MBP-10 µg/mL | 0.9 | 0.4 | 3 |
| | GA-10 µg/mL | 1.8 | 0.8 | 3 |
| | ConA-2.5 µg/mL | 8.9 | 3.8 | 2 |

Abbreviations: MBP = Myelin Basic Protein (a negative control); ConA = Concanavalin A (a positive control); GA = Glatiramer acetate; SD = Standard deviation; NA = Not applicable (n < 3).

Figure 2:
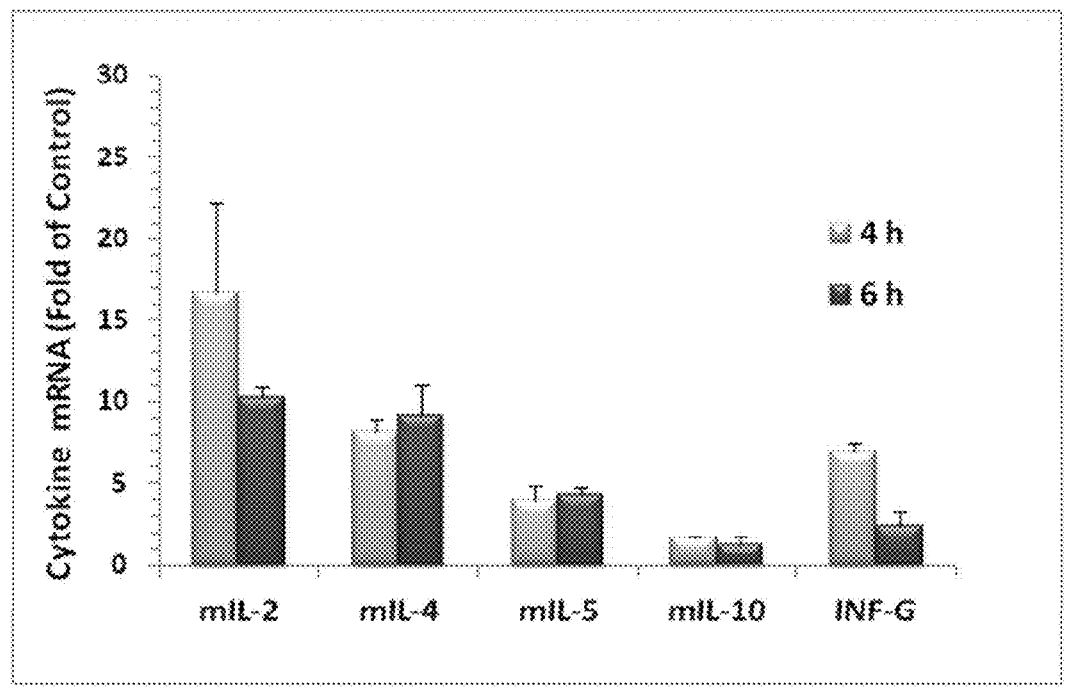
FIG. 2. Cytokine mRNA Expressed in Primary LN Cells in Response to GA Stimulation. This figure shows a summary of the data presented herein in Tables 8-12. LN cells from GA-immunized mice were stimulated ex vivo with GA and cytokine mRNA was measured at 4 hours after stimulation (light bars) and at 6 hours after stimulation (dark bars) as indicated. Cytokine mRNA levels are expressed as fold increase relative to a DCCM1 (culture medium) control.
Figure 3A:
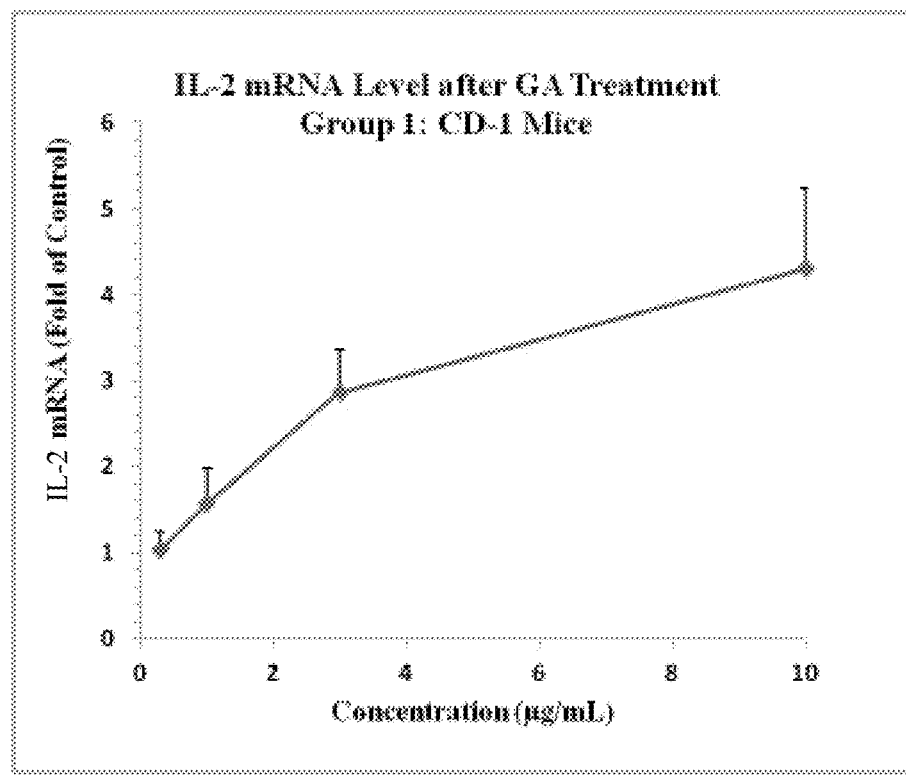
FIG. 3. Response Biomarker mRNA Expression Levels in Primary LN Cells from GA-Immunized CD-1 Mice in Response to Stimulation with GA: IL-2 and IL-4. mRNA levels expressed as fold change vs. control are plotted as a function of GA stimulation concentration. A. IL-2 mRNA expression in LN cells from strain CD-1 mice. B. IL-4 mRNA expression in LN cells from strain CD-1 mice.
Figure 3B:
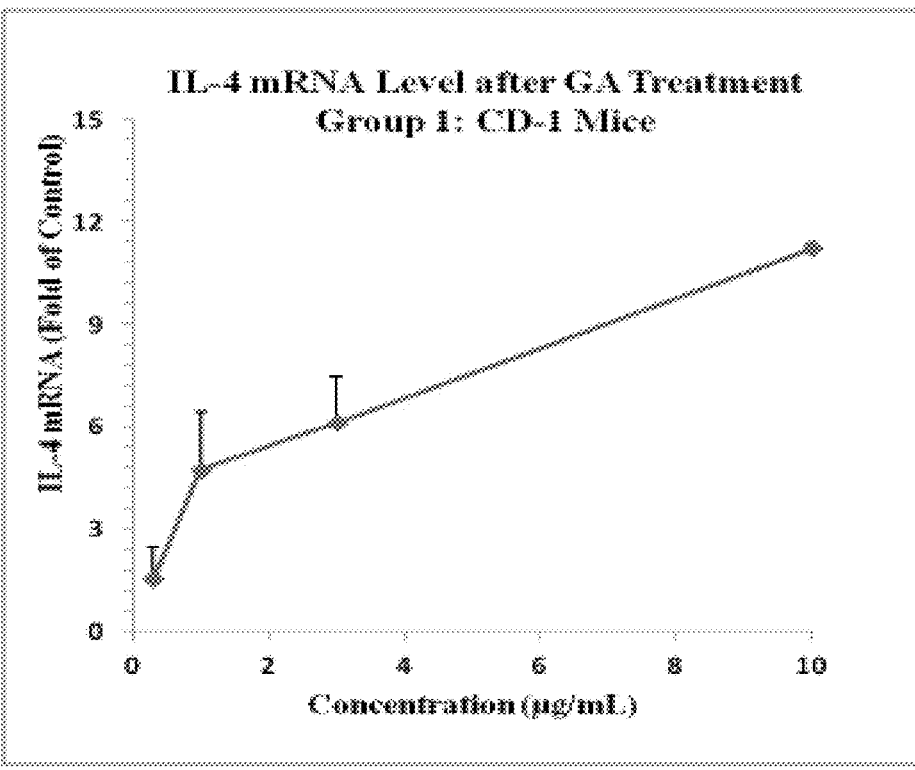
Figure 4:
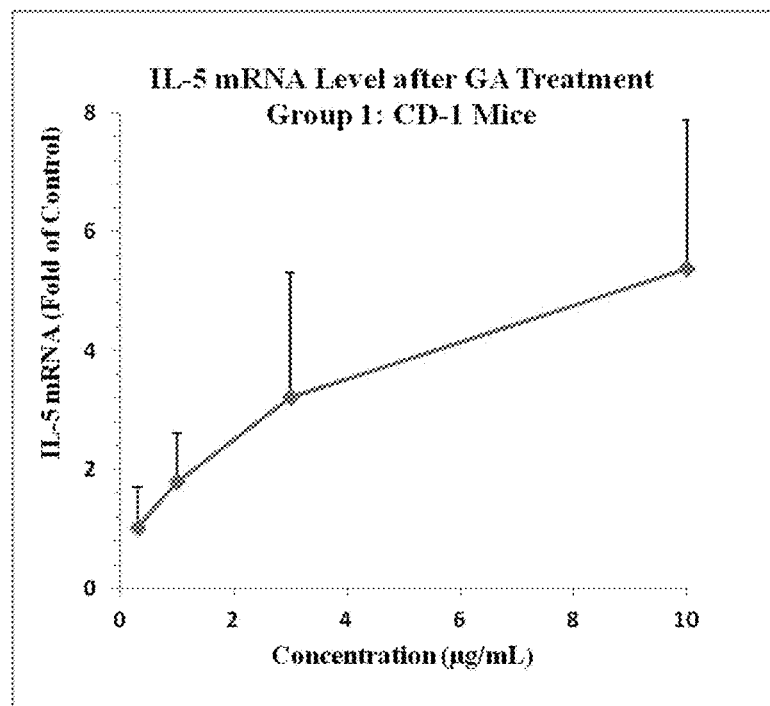
FIG. 4. Response Biomarker mRNA Expression Levels in Primary LN Cells from GA-Immunized CD-1 Mice in Response to Stimulation with GA: IL-5 and IL-10. mRNA levels expressed as fold change vs. control are plotted as a function of GA stimulation concentration. A. IL-5 mRNA expression in LN cells from strain CD-1 mice. B. IL-10 mRNA expression in LN cells from strain CD-1 mice.
Figure 4:
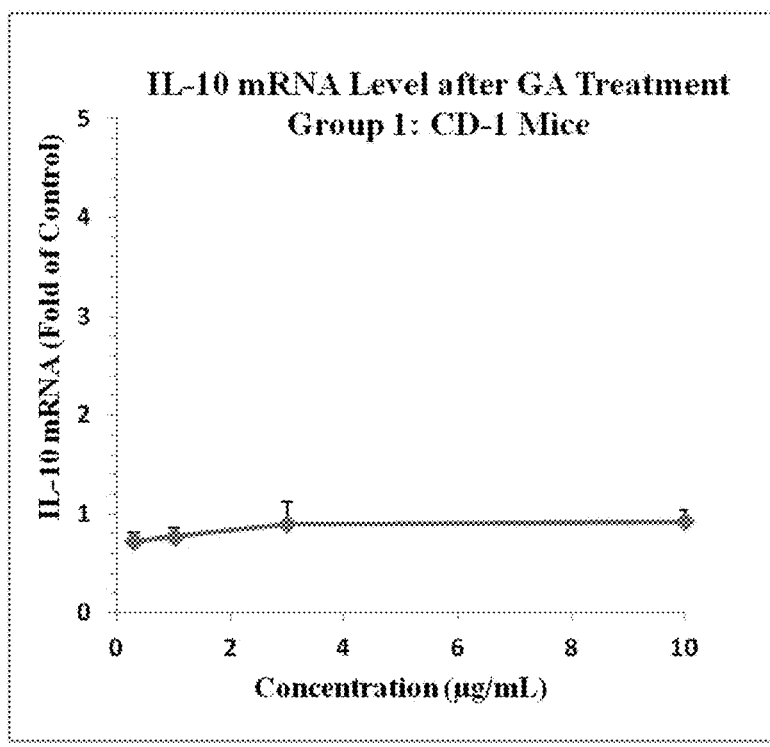
Figure 5:
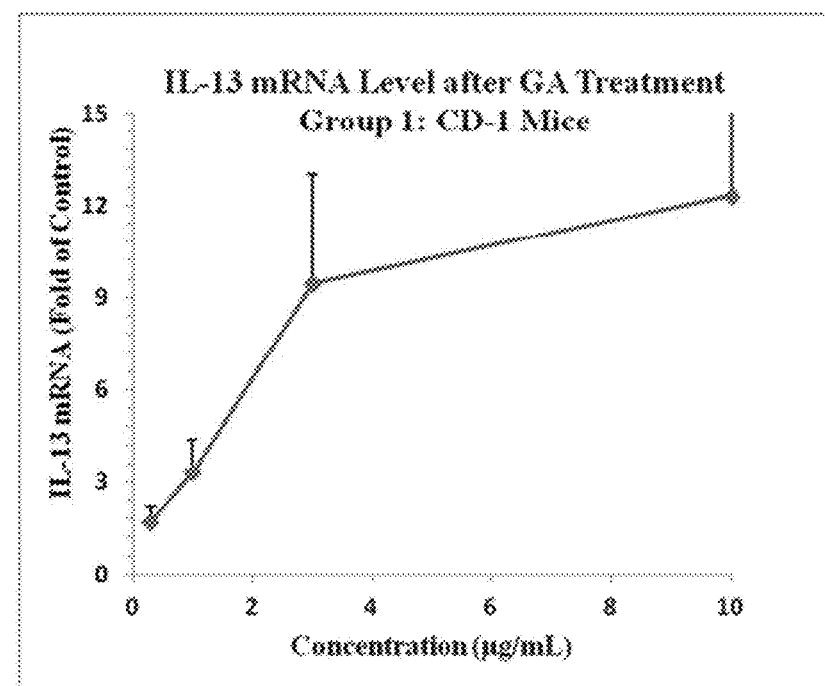
FIG. 5. Response Biomarker mRNA Expression Levels in Primary LN Cells from GA-Immunized CD-1 Mice in Response to Stimulation with GA: IL-13 and IFN-γ. mRNA levels expressed as fold change vs. control are plotted as a function of GA stimulation concentration. A. IL-13 mRNA expression in LN cells from strain CD-1 mice. B. IFN-γ mRNA expression in LN cells from strain CD-1 mice.
Figure 5:
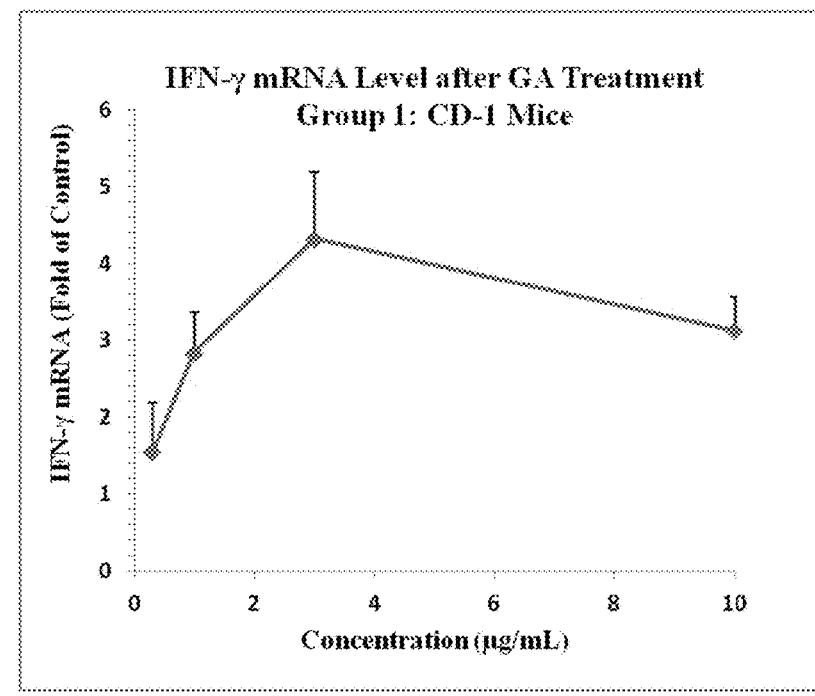
Figure 6:
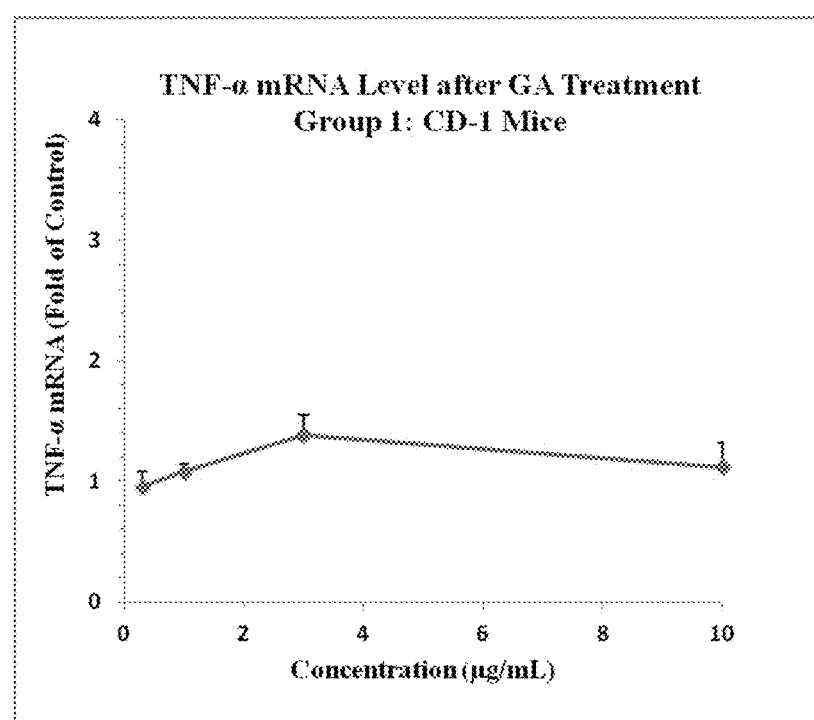
FIG. 6. Response Biomarker mRNA Expression Levels in Primary LN Cells from GA-Immunized Mice in Response to Stimulation with GA: TNF-α and IL-2. mRNA levels expressed as fold change vs. control are plotted as a function of GA stimulation concentration. A. TNF-α mRNA expression in LN cells from strain CD-1 mice. B. IL-2 mRNA expression in LN cells from strain BALB/cByJ mice.
Figure 6:
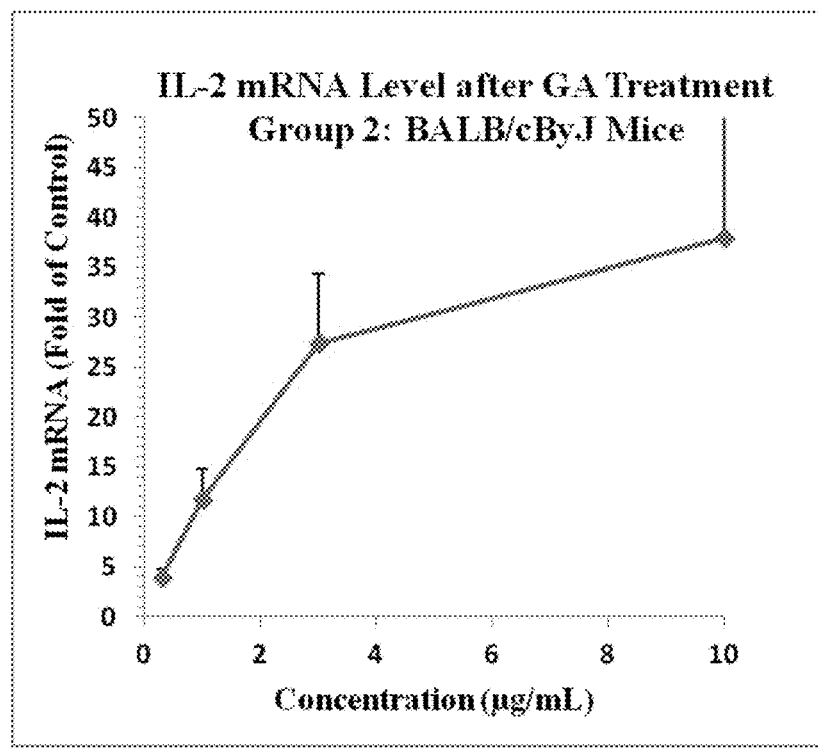
Figure 7:
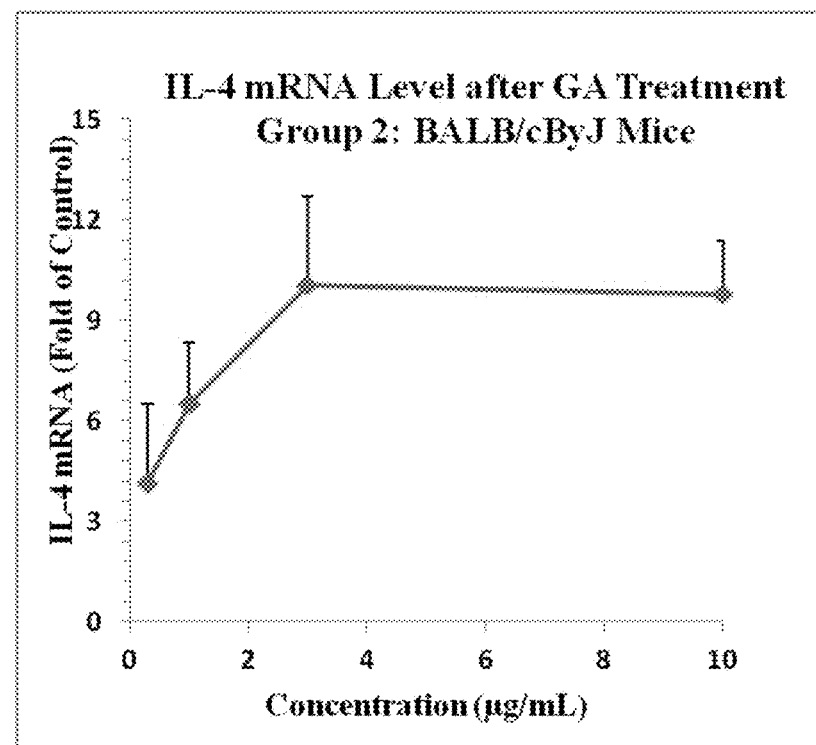
FIG. 7. Response Biomarker mRNA Expression Levels in Primary LN Cells from GA-Immunized BALB/cByJ Mice in Response to Stimulation with GA: IL-4 and IL-5. mRNA levels expressed as fold change vs. control are plotted as a function of GA stimulation concentration. A. IL-4 mRNA expression in LN cells from strain BALB/cByJ mice. B. IL-5 mRNA expression in LN cells from strain BALB/cByJ mice.
Figure 7:
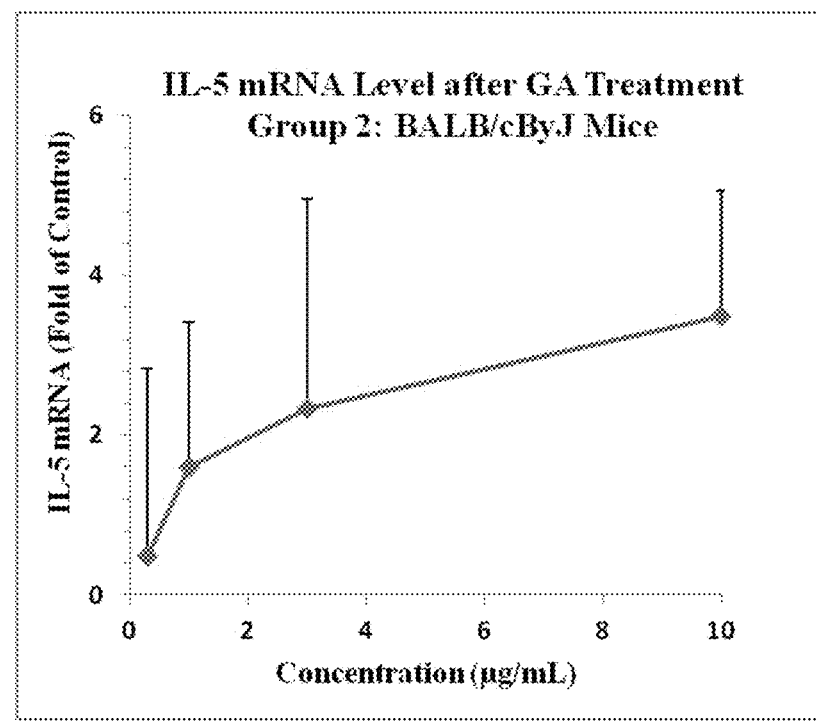
Figure 8:
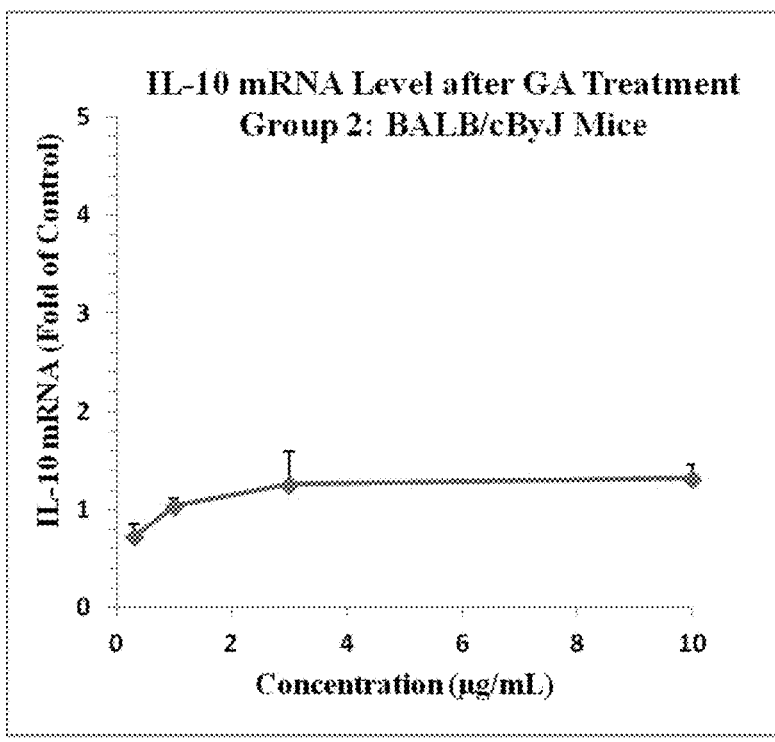
FIG. 8. Response Biomarker mRNA Expression Levels in Primary LN Cells from GA-Immunized BALB/cByJ Mice in Response to Stimulation with GA: IL-10 and IL-13. mRNA levels expressed as fold change vs. control are plotted as a function of GA stimulation concentration. A. IL-10 mRNA expression in LN cells from strain BALB/cByJ mice. B. IL-13 mRNA expression in LN cells from strain BALB/cByJ mice.
Figure 8:
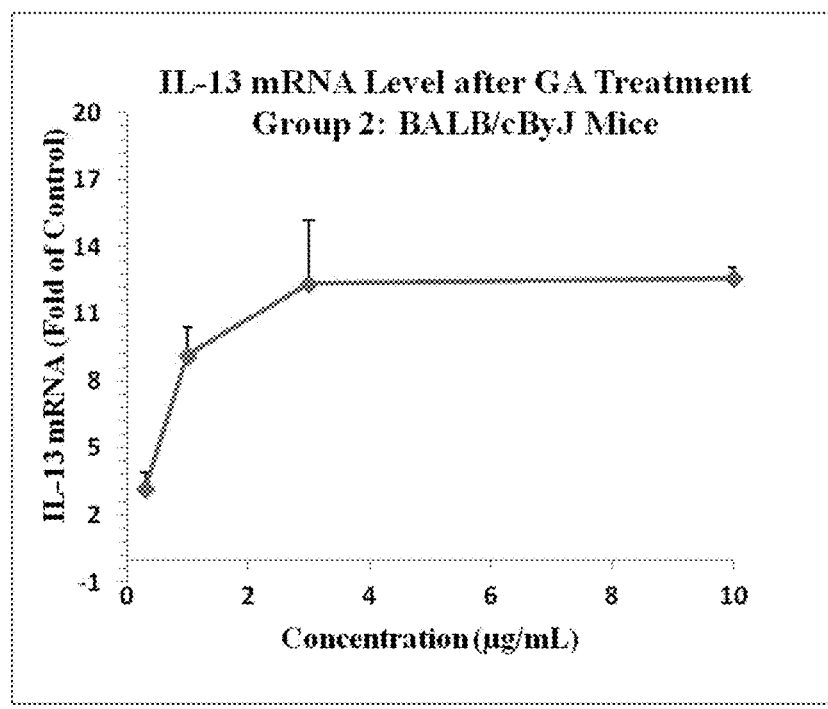
Figure 9:
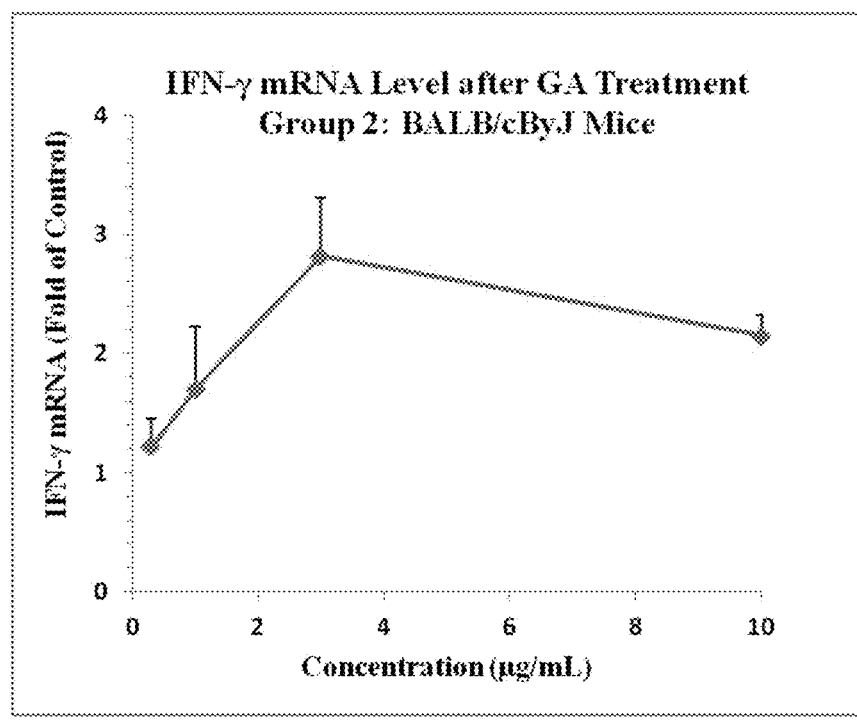
FIG. 9. Response Biomarker mRNA Expression Levels in Primary LN Cells from GA-Immunized BALB/cByJ Mice in Response to Stimulation with GA: IFN-γ and TNF-α. mRNA levels expressed as fold change vs. control are plotted as a function of GA stimulation concentration. A. IFN-γ mRNA expression in LN cells from strain BALB/cByJ mice. B. TNF-α mRNA expression in LN cells from strain BALB/cByJ mice.
Figure 9:
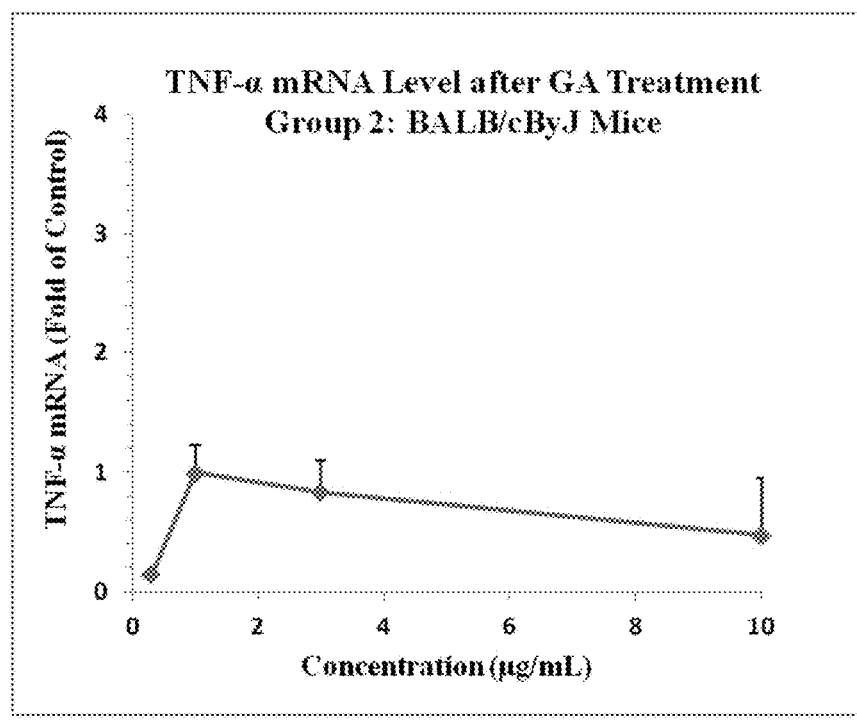
Figure 10:
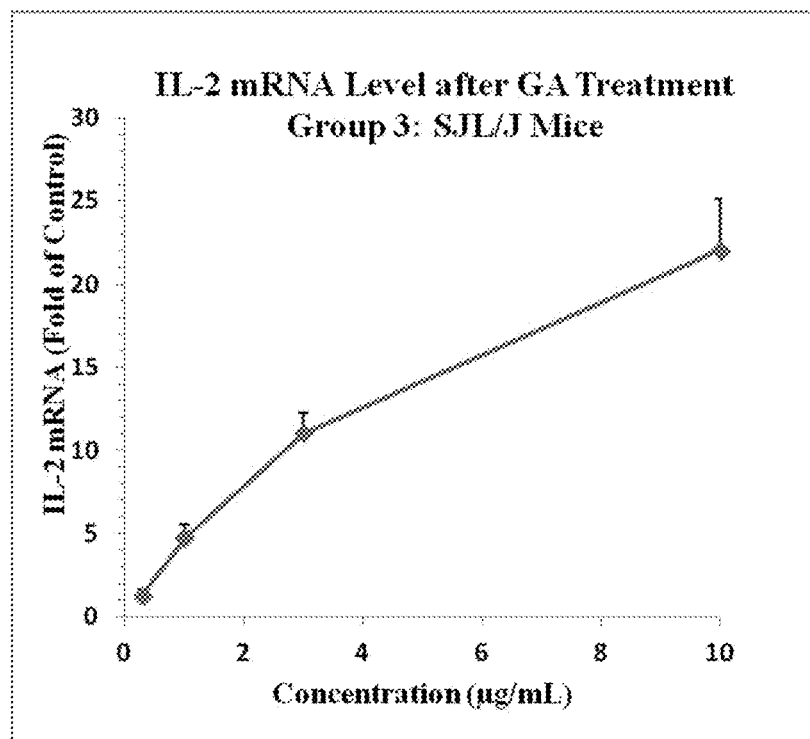
FIG. 10. Response Biomarker mRNA Expression Levels in Primary LN Cells from GA-Immunized SJL/J Mice in Response to Stimulation with GA: IL-2 and IL-4. mRNA levels expressed as fold change vs. control are plotted as a function of GA stimulation concentration. A. IL-2 mRNA expression in LN cells from strain SJL/J mice. B. IL-4 mRNA expression in LN cells from strain SJL/J mice.
Figure 10:
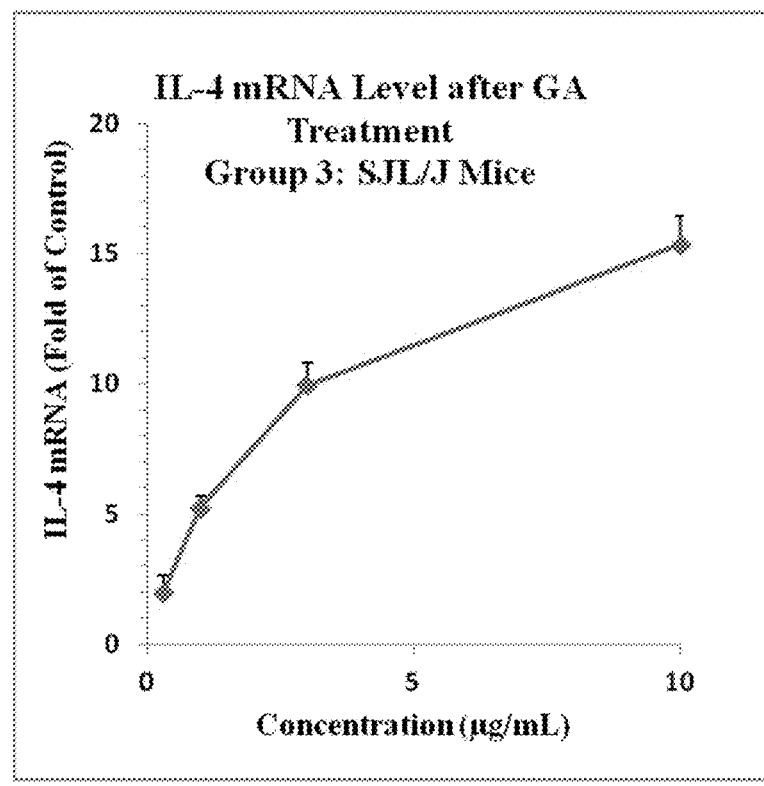
Figure 11:
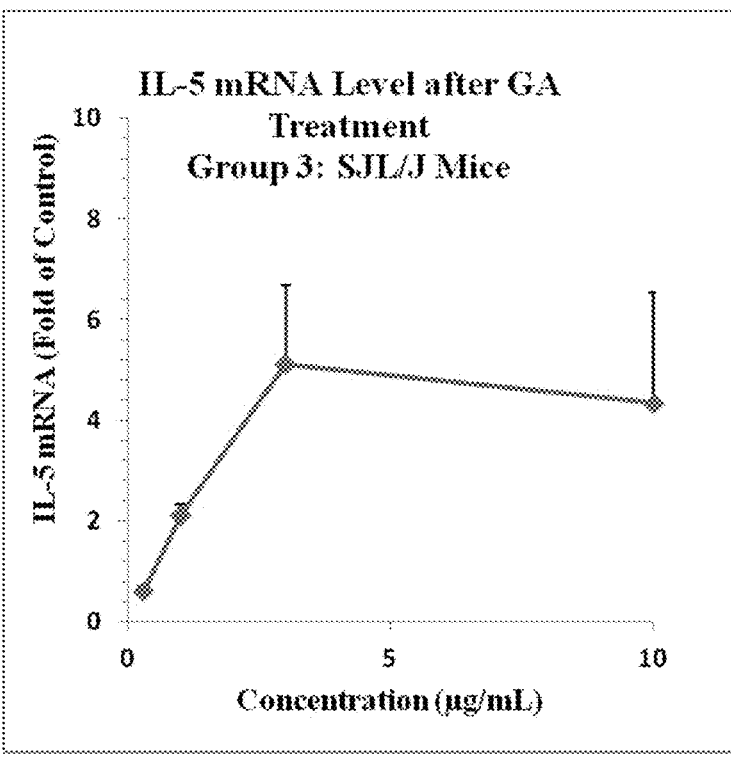
FIG. 11. Response Biomarker mRNA Expression Levels in Primary LN Cells from GA-Immunized SJL/J Mice in Response to Stimulation with GA: IL-5 and IL-10. mRNA levels expressed as fold change vs. control are plotted as a function of GA stimulation concentration. A. IL-5 mRNA expression in LN cells from strain SJL/J mice. B. IL-10 mRNA expression in LN cells from strain SJL/J mice.
Figure 11:
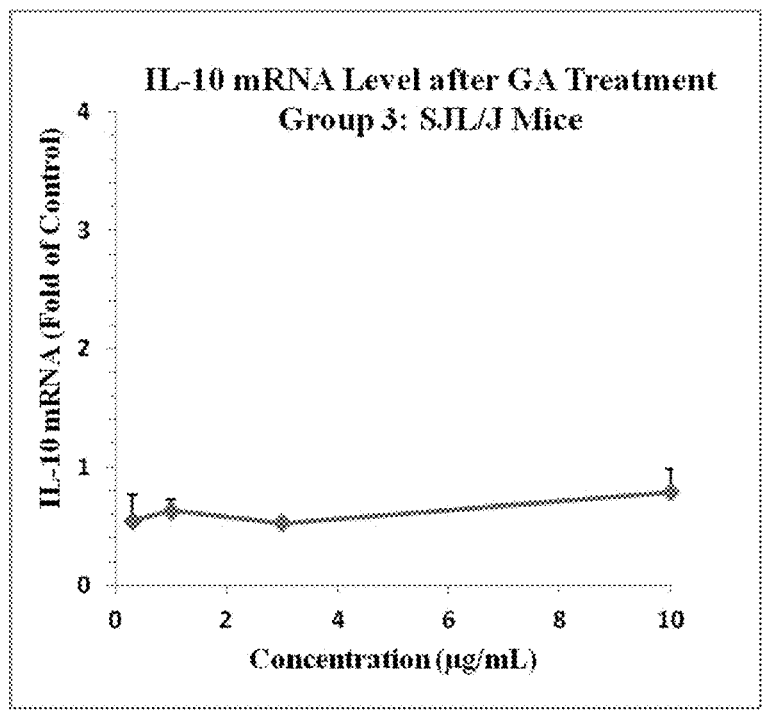
Figure 12:
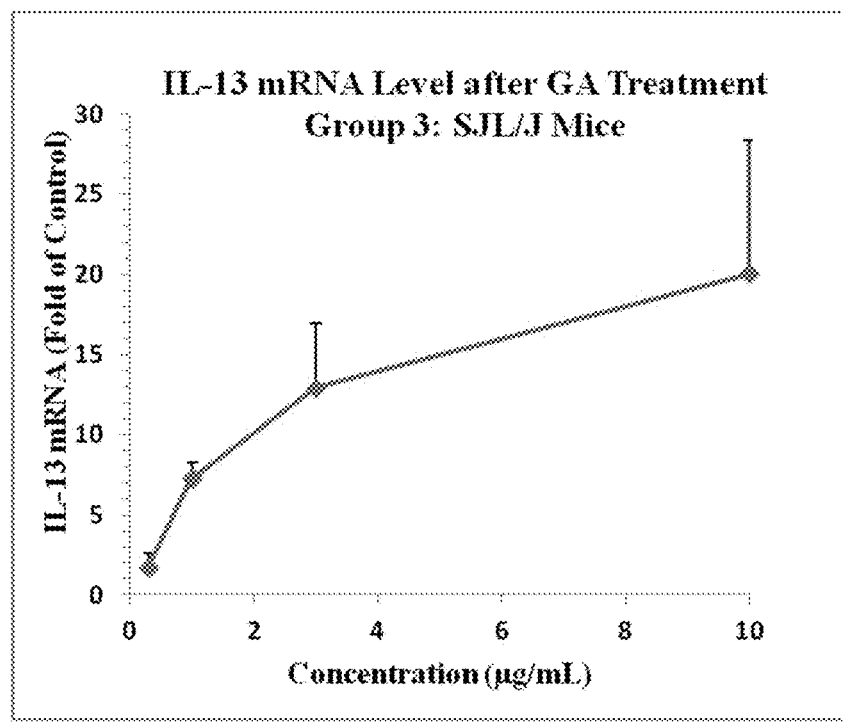
FIG. 12. Response Biomarker mRNA Expression Levels in Primary LN Cells from GA-Immunized SJL/J Mice in Response to Stimulation with GA: IL-13 and IFN-γ. mRNA levels expressed as fold change vs. control are plotted as a function of GA stimulation concentration. A. IL-13 mRNA expression in LN cells from strain SJL/J mice. B. IFN-γ mRNA expression in LN cells from strain SJL/J mice.
Figure 12:
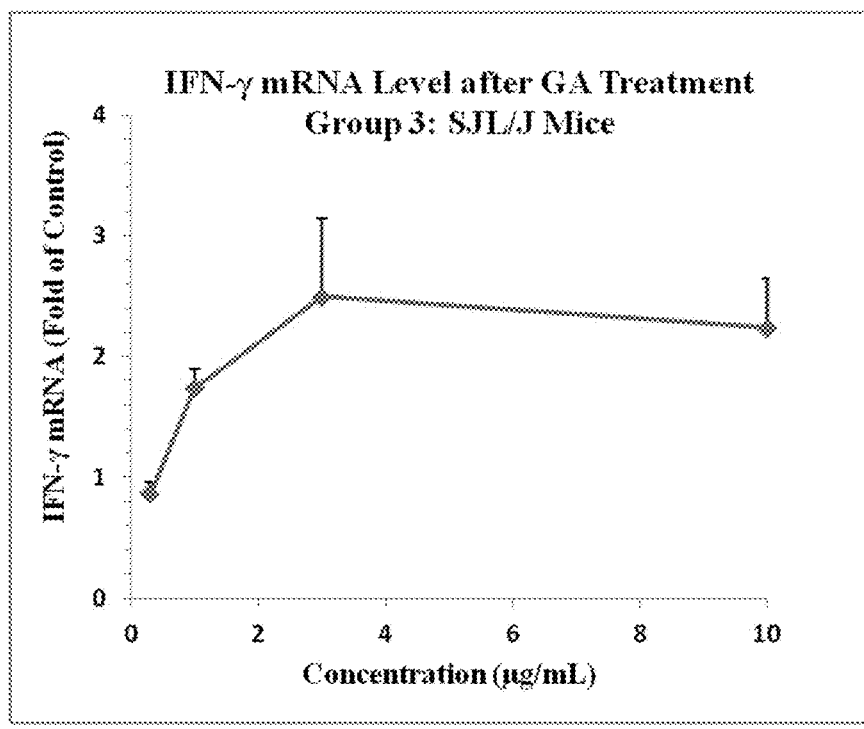
Figure 13:
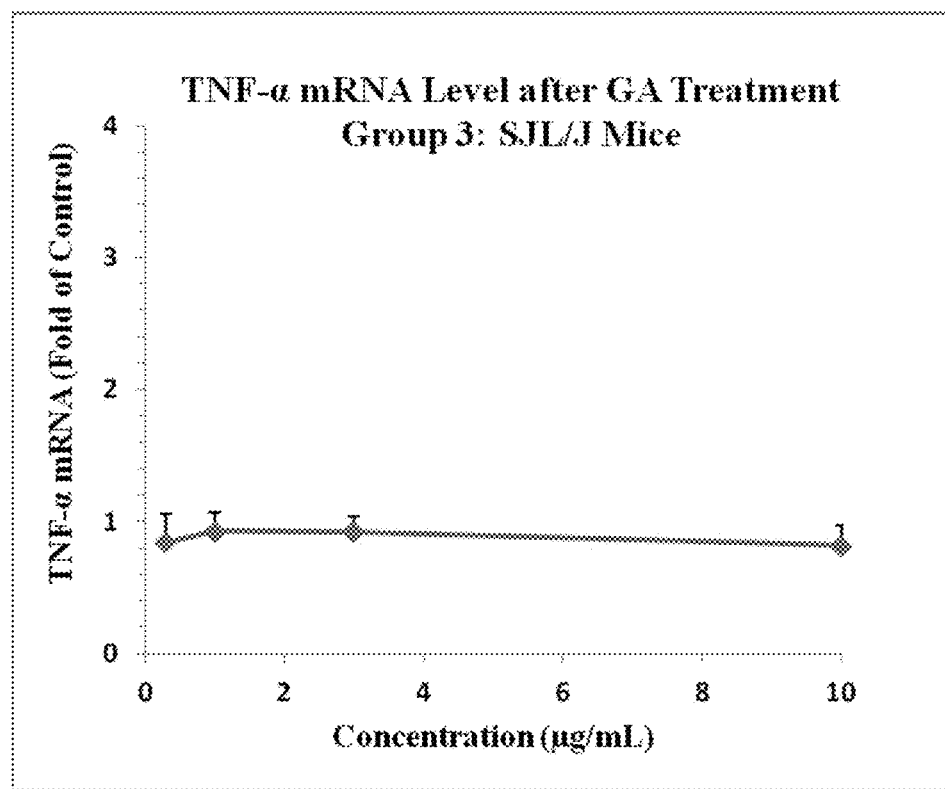
FIG. 13. Response Biomarker mRNA Expression Levels in Primary LN Cells from GA-Immunized SJL/J Mice in Response to Stimulation with GA: TNF-α. mRNA levels expressed as fold change vs. control are plotted as a function of GA stimulation concentration. Graph shows TNF-α mRNA expression in LN cells from strain SJL/J mice.

FIG. 2 provides a summary of the increases in cytokine mRNA expression presented in Tables 8 to 12.

Example II. Secretion of Cytokines by T-Cells from Three Strains of Mice Following Stimulation with Glatiramer Acetate This Example describes experiments that were performed to evaluate three additional mouse strains for use in obtaining GA-specific T-cells for GA potency assays. The kinetics of secretion of nine cytokines (IL-1β, IL-2, IL-4, IL-5, IL-10, IL-12, IFN-γ, TNF-α, and CXCL1, also referred to as KC), by GA-specific T-cells isolated from CD-1, BALB/cByJ, and C57BL/10J mice, in response to ex vivo GA stimulation, were tested in parallel. Cytokine secretion was compared in LN cells immunized by intraplantar injection and cells immunized by lower limb injection.

Table 13 shows the experimental design.

TABLE 13

Experimental Design: Evaluation of Cytokine Secretion in Three Mouse Strains

| Mouse Strain | Group | Dose Route | # Animals/Gender | Stimulation | Dose of GA/mouse (Day 0) |
|---|---|---|---|---|---|
| CD-1 | 1 | Intraplantar (4 foot pad) | 5/F | GA + CFA | 250 µg |
| | 2 | Lower limb or hock | 5/F | GA + CFA | 250 µg |
| | 3 | Intraplantar (4 foot pad) | 4/F | Mannitol + CFA | 0 µg |
| BALB/cByJ | 4 | Intraplantar (4 foot pad) | 5/F | GA + CFA | 250 µg |
| | 5 | Lower limb or hock | 5/F | GA + CFA | 250 µg |
| | 6 | Intraplantar (4 foot pad) | 4/F | Mannitol + CFA | 0 µg |
| C57BL/10J | 7 | Intraplantar (4 foot pad) | 5/F | GA + CFA | 250 µg |
| | 8 | Lower limb or hock | 5/F | GA + CFA | 250 µg |
| | 9 | Intraplantar (4 foot pad) | 4/F | Mannitol + CFA | 0 µg |

Abbreviations: GA = Glatiramer acetate; CFA = Complete Freunds' Adjuvant (1 mg/ml)

Female CD-1, BALB/cByJ and C57BL/10J mice (14 of each, from Hilltop Laboratories, Jackson Laboratory, and Jackson Laboratory, respectively) were immunized as indicated in Table 13 with GA (GMA, Mylan Pharmaceuticals, Inc., prepared in DPBS) or a mannitol control via intraplantar or lower limb injection. Animals at 8 weeks of age were immunized by injection into four footpads using a 1 mL syringe with a 27-G, ½-inch needle. For intraplantar injection, each mouse received a total injection volume of 0.1 mL (about 10 μL into each of the front footpads and 40 μL into each of the hind footpads). For subcutaneous injection in the lower limbs, each mouse received a total injection volume of 0.1 mL (about 25 μL into each of the front lower limbs and 25 μL into each hock of the hind limbs).

Ten days post-immunization, immunized animals were sacrificed via cervical dislocation. Lymph nodes in the axillary and popliteal regions from immunized mice were removed and pooled by group into petri dishes containing 5 mL of ice cold, sterile RPMI-1640 medium. The intact lymph nodes were washed three times in 5.0 mL ice cold, sterile RPMI 1640 medium. The LN cells were isolated by pressing the LN with the plunger end of a sterile syringe. The cell suspension was first passed through a 100 μm nylon cell strainer and then washed once with 40 mL of ice cold RPMI-1640 medium. After centrifugation at ca. 200×g for 10 minutes at 4° C., the cell pellet was re-suspended in 40 mL of RPMI-1640 medium for cell counting. Trypan blue exclusion method was used to determine the cell density of viable cells in the suspension. After cell counting, the LN cells were centrifuged at ca. 200×g for 10 minutes at 4° C. and re-suspended in enriched DCCM-1 medium (2 mM GlutaMax, 1× antibiotic-antimycotic, 55 μM 2-mercaptoethanol, 1 mM MEM sodium pyruvate solution, and 100 μM MEM non-essential amino acid solution in DCCM-1 medium, Beit Haemek Ltd.; Cat. No. 05 010 1A) at a cell density of $1.0 \times 10^7$ cell/mL. LN cells were plated into a 24-well tissue culture plate for drug stimulation.

Each group of primary LN cells (0.5 mL, $5 \times 10^6$ cells/well) immunized with GA (Groups 1, 2, 3, 5, 7 and 8) was stimulated with four concentrations of GA solution (the same batch of Mylan GMA used for immunization, 0.5 mL, final concentration 0.5, 1.0, 2.5 and 10 μg/mL). Each group of LN cells from animals immunized with mannitol (Groups 3, 6 and 9) was treated with two GA dilution samples (0.5 and 1.0 μg/mL, or 2.5 and 10 μg/mL GA) using the same procedure.

After incubation at 37° C. in a humidified 5% $CO_2$ incubator for 21 hours, the culture media were harvested at designated timepoints. Cell debris was removed by centrifugation at ca. 200×g for 10 minutes at 4° C. Cytokines secreted by treated cells were determined on the day of collection by ELISA using mouse TH 1/TH 2 9-Plex Tissue Culture Kit (Meso Scale Discovery; Cat No. K15013B-2, Lot #: K0032839) which detects Th1 cytokines (IFN-γ, IL-2, IL-12, IL-1β, TNF-α, CXCL1) and Th2 cytokines (IL-4, IL-5 and IL-10). For IFN-γ, culture media also were assayed at 45 hours using mouse IFN-γ Tissue Culture Kit (Meso Scale Discovery; Cat No. K152AEB-2, Lot# K0033074).

Control samples were prepared to monitor the assay performance, including the stimulation of LN cells with Concanavalin A (ConA), a non-specific T-cell stimulator, as a positive control and myelin basic protein (MBP), as a negative control. For the positive control, 0.5 mL of LN cells ($5 \times 10^6$ cells/well) were treated with 0.5 mL of ConA (5 μg/mL). For the negative control, 0.5 mL of LN cells ($5 \times 10^6$ cells/well) were treated with 0.5 mL of MBP (20 μg/mL). The LN cells with mock stimulation (enriched DCCM1 medium) were used to monitor the background level of a cytokine.

For the cytokine assays, calibration standards or samples were incubated in the MULTI-SPOT or the SINGLE-SPOT plate and each cytokine bound to its corresponding capture antibody. All test samples were run in duplicate. The amount of each cytokine on its distinct spot was quantified using a cytokine-specific detection antibody labeled with MSD SULFO-TAG™ reagent. Electrochemiluminescent signals from immobilized SULFO-TAG™-labeled complexes on each spot from each well were captured by the MSD SECTOR Imager 6000, which produces a signal directly proportional to the amount of captured cytokine in a test sample. The levels of cytokines in test samples were derived by interpolation from calibration curves with calibration standards of known concentrations using reagents provided with the MSD kits. Kits were used according to the manufacturer's protocols.

Table 14 shows the cytokines secreted by GA-stimulated LN cells from each of the three mouse strains tested. Data are expressed as a response ratio of cytokine concentration in treated cell medium to control DCCM1 medium.

TABLE 14

Cytokine Secretion in Response to GA Stimulation of LN Cells from Three Mouse Strains

| Assay (21 hr) | Treatment | Group 1 CD-1 | | | Group 2 BALB/cByJ | | | C57BL10J | | |
|---|---|---|---|---|---|---|---|---|---|---|
| | | GA Intraplantar | GA Lower Limb | Mannitol Intraplantar | GA Intraplantar | GA Lower Limb | Mannitol Intraplantar | GA Intraplantar | GA Lower Limb | Mannitol Intraplantar |
| IL-2 | ConA | 85.01 | 19.64 | 68.22 | 229.32 | 283.65 | 281.66 | 40.09 | 31.11 | 28.71 |
| | MBP | 0.98 | 1.29 | 1.28 | 0.97 | 1.13 | 0.97 | 1.18 | 1.30 | 0.98 |
| | GA | 7.69 | 2.77 | 1.35 | 14.53 | 38.96 | 1.44 | 4.94 | 6.45 | 0.94 |
| IL-12 (total) | ConA | 1.09 | 1.91 | 1.80 | 1.66 | 1.10 | 1.44 | 1.88 | 1.01 | 0.92 |
| | MBP | 1.22 | 1.18 | 0.99 | 1.09 | 1.04 | 1.05 | 1.18 | 1.19 | 1.13 |
| | GA | 1.06 | 1.08 | 0.98 | 0.98 | 1.23 | 1.22 | 1.09 | 1.18 | 1.20 |
| IL-1b | ConA | 8.50 | 2.86 | 3.37 | 11.73 | 8.70 | 7.83 | 2.21 | 1.42 | 1.40 |
| | MBP | 1.37 | 1.00 | 1.20 | 1.15 | 0.96 | 0.87 | 0.99 | 1.17 | 0.92 |
| | GA | 5.07 | 1.59 | 1.09 | 3.88 | 2.72 | 1.10 | 1.03 | 1.15 | 0.74 |
| TNF-α | ConA | 17.59 | 9.79 | 23.88 | 27.69 | 10.87 | 11.61 | 2.53 | 2.02 | 2.10 |
| | MBP | 1.34 | 1.54 | 1.51 | 0.98 | 1.07 | 1.10 | 1.03 | 1.04 | 1.01 |
| | GA | 1.68 | 1.21 | 1.24 | 1.63 | 1.59 | 1.66 | 1.22 | 0.93 | 1.26 |
| KC | ConA | 1.56 | 1.65 | 2.55 | 1.52 | 0.90 | 1.00 | 1.55 | 1.28 | 1.34 |
| | MBP | 1.05 | 1.08 | 1.09 | 1.04 | 1.02 | 0.96 | 1.00 | 1.04 | 1.12 |
| | GA | 1.02 | 1.18 | 1.14 | 1.15 | 0.94 | 1.15 | 1.16 | 1.16 | 1.06 |
| IFN-γ | ConA | 10.14 | 1.90 | 9.35 | 9.70 | 6.24 | 4.40 | 11.55 | 5.07 | 4.05 |
| | MBP | 1.06 | 0.90 | 1.57 | 0.87 | 0.80 | 1.17 | 1.03 | 1.60 | 2.02 |
| | GA | 18.99 | 2.69 | 2.75 | 9.33 | 6.08 | 2.58 | 7.50 | 7.64 | 2.30 |

TABLE 14-continued

Cytokine Secretion in Response to GA Stimulation of LN Cells from Three Mouse Strains

| Assay (21 hr) | Treatment | Group 1 CD-1 | | | Group 2 BALB/cByJ | | | C57BL10J | | |
|---|---|---|---|---|---|---|---|---|---|---|
| | | GA Intraplantar | GA Lower Limb | Mannitol Intraplantar | GA Intraplantar | GA Lower Limb | Mannitol Intraplantar | GA Intraplantar | GA Lower Limb | Mannitol Intraplantar |
| IFN-γ | ConA | 5.47 | 1.89 | 9.68 | 11.40 | 7.33 | 3.48 | 53.10 | 5.15 | 5.90 |
| (45 hr) | MBP | 0.89 | 2.11 | 7.22 | 0.83 | 0.92 | 0.92 | 1.07 | 1.80 | 1.41 |
| | GA | 10.17 | 2.57 | 7.95 | 9.59 | 7.89 | 2.20 | 8.28 | 11.01 | 2.25 |
| IL-4 | ConA | 9.86 | 4.91 | 3.36 | 46.47 | 75.33 | 24.71 | 3.26 | 4.85 | 3.14 |
| | MBP | 0.99 | 0.94 | 1.21 | 0.99 | 1.05 | 1.50 | 1.09 | 1.14 | 1.03 |
| | GA | 4.81 | 1.97 | 1.18 | 10.06 | 10.54 | 1.74 | 1.38 | 1.87 | 0.88 |
| IL-5 | ConA | 13.49 | 6.35 | 7.11 | 22.09 | 14.24 | 13.33 | 8.16 | 5.24 | 3.93 |
| | MBP | 1.33 | 1.00 | 1.16 | 1.22 | 0.99 | 1.07 | 1.31 | 0.85 | 0.99 |
| | GA | 6.10 | 2.32 | 1.05 | 6.02 | 4.41 | 1.40 | 1.69 | 1.41 | 0.92 |
| IL-10 | ConA | 13.70 | 8.64 | 10.96 | 23.65 | 18.32 | 21.86 | 1.62 | 1.50 | 1.04 |
| | MBP | 1.39 | 1.41 | 1.38 | 1.10 | 1.12 | 1.07 | 1.04 | 1.00 | 1.08 |
| | GA | 3.25 | 2.13 | 1.50 | 4.01 | 3.35 | 1.36 | 1.63 | 1.50 | 1.66 |

Abbreviations: GA = Glatiramer acetate; CFA = Complete Freunds' Adjuvant (1 mg/ml); KC = (CXCL1)

$$\text{Response Ratio} = \frac{\text{Analyte Concentration Treated with ConA, MBP or GA}}{\text{Analyte Concentration in DCCM1 Medium}}$$

As shown in Table 14, secretion of IL-2, IL-4, IL-5, IL-10 and IFN-γ appeared specific for GA stimulation and showed a dose-dependent increase with GA concentration. The levels of these cytokines were higher in GA-stimulated LN cells from animals immunized with GA than in the same cells when not stimulated. Furthermore, secretion of cytokines in GA-treated cells was not observed in cells isolated from mannitol-immunized control animals.

LN cells from BALB/cByJ mice secreted IL-2, IL-4, IL-5 and IL-10 (Groups 4-6) in response to GA stimulation was either similar to or higher than secretion in LN cells from CD-1 mice (Groups 1-3). While IFN-γ secretion was higher in CD-1 LN cells than in BALB/cByJ cells following ~21 hour GA stimulation, it was similar between LN cells from the two strains after 45 hr GA incubation. No dose response of IL-12, TNF-α and KC secretion after GA stimulation was detected for cells from any of the three mouse strains. Dose response of IL-1β was detected in LN cells from BALB/cByJ and CD-1 mouse strains when cells were primed by intraplantar injection.

IL-4 was secreted in response to GA in a dose-dependent manner in BALB/cByJ cells. The response to GA was similar in cells primed by intraplantar injection and cells primed by lower limb injection.

IL-2 was secreted in response to GA in a dose-dependent manner in LN cells from each of the three mouse strains. The highest IL-2 response was detected in BALB/cByJ cells. BALB/cByJ cells from animals primed by lower limb GA injection appeared to have a higher response than cells primed by intraplantar injection. In C57BL/10J mice, the IL-2 response to GA stimulation was similar in LN cells primed via intraplantar injection and cells primed by lower limb injection.

IFN-γ was secreted in response to GA in a dose-dependent manner in LN cells from each of the three mouse strains. In general, cells primed by intraplantar GA injection appeared to have similar or higher response than cells primed by lower limb injection in all three strains.

IL-5 was secreted in response to GA in a dose-dependent manner in BALB/cByJ cells and CD1 cells. The IL-5 response to GA was dose dependent and higher in cells primed by intraplantar injection than by lower limb injection.

IL-10 was secreted in response to GA in a dose-dependent manner in BALB/cByJ cells and CD1 cells. The IL-10 response to GA was dose dependent and higher in cells primed by intraplantar injection than by lower limb injection.

Example III. A Glatiramer Acetate Potency Assay that Measures Response Biomarker mRNA in Lymph Node Cells from Glatiramer Acetate-Immunized CD-1, BALB/cByJ, and SJL/J Mouse Strains Following Challenge with Glatiramer Acetate T-cells from CD-1, BALB/cByJ, and SJL/J mouse strains (from Hilltop Laboratory, Jackson Laboratory, and Jackson Laboratory, respectively) immunized with GA were used in a GA potency assay of the present invention. LN cells obtained from GA-immunized mice demonstrated substantial increases in cytokine mRNA levels in response to GA stimulation at 6 hours after the stimulation.

Table 15 shows the experiment design for immunization of each of the three strains. On Day 0, mice were immunized with 250 μg GA (GMA, Mylan Pharmaceuticals, Inc.) and CFA. The GA solution (20 mg/mL) was diluted with Dulbecco's Phosphate-Buffered Saline to 5 mg/mL. The dosing formulation consisted of equal volumes of the diluted GA solution (5 mg/mL) and CFA solution, mixed until well-emulsified. Animals were weighed and allocated to groups. Animals were dosed by injection into four footpads. The injection volume per animal was 0.1 mL (about 10 μL into each front footpad, and 40 μL into each hind footpad).

TABLE 15

Experiment Design: Evaluation of Response Biomarker mRNA in Three Mouse Strains

| Mouse Strain | Group | Dose Route | # Animals/ Gender | Immunization Stimulation | Dose of GA/mouse (Day 0) |
|---|---|---|---|---|---|
| CD-1 | 1C | Inject into four footpads | 6/F | Mylan GA + CFA | 250 μg |

TABLE 15-continued

Experiment Design: Evaluation of Response
Biomarker mRNA in Three Mouse Strains

| Mouse Strain | Group | Dose Route | # Animals/ Gender | Immunization Stimulation | Dose of GA/mouse (Day 0) |
|---|---|---|---|---|---|
| BALB/cByJ | 2C | Inject into four footpads | 6/F | Mylan GA + CFA | 250 µg |
| SJL/J | 3C | Inject into four footpads | 6/F | Mylan GA + CFA | 250 µg |

Abbreviations: F = female; GA = glatiramer acetate; CFA = Complete Freund's Adjuvant.

Table 16 shows the experiment design for stimulation of LN cells from the immunized mice. Immunized animals were euthanized by cervical dislocation on Day 10 post-immunization. Lymph node cells were isolated from animals and treated with Myelin Basic Protein (MBP, a negative control), Concanavalin A (ConA, a positive control) or GA as shown in Table 16. Lymph nodes in the axillary and popliteal regions were removed aseptically in a purifier clean bench. Lymph nodes were transferred into a sterile petri dish containing about 5 mL of sterile RPMI 1640 medium. The LN were then washed 3 times with −5 mL of RPMI medium, and isolated by pressing the LN with a syringe plunger. The cell suspension was transferred to a sterile 50 mL conical tube and washed in about 40 mL of RPMI medium by centrifugation at about 200×g for 10 minutes at about 4° C., and re-suspended in RPMI 1640 medium for cell counting. The cell suspension was centrifuged at about 200×g for 10 minutes at about 4° C. and re-suspended in ice cold enriched DCCM-1 medium. Cells were seeded in 96-well tissue culture plates.

TABLE 16

Stimulations: Evaluation of Response Biomarker
mRNA in LN Cells from Three Mouse Strains

| # of mice | LN Cells (Animal Immunized with) | Stimulation | Stimulation Concentration (µg/mL) |
|---|---|---|---|
| 6 | GA + CFA | GA | 0.3, 1, 3, 10 |
| | | ConA | 2.5 |
| | | MBP | 10 |
| | | Enriched DCCM-1 | 0 |

LN cells isolated from GA-immunized animals were stimulated with GA (GMA, Mylan Pharmaceuticals, Inc.) at concentrations as indicated in Tables 16 and 17. A positive control was prepared by treating LN cells with 2.5 µg/mL concavalin A (ConA, a non-specific T cell stimulant). Myelin basic protein (MBP, 10 µg/mL) and enriched DCCM-1 medium served as negative controls. The cells from all groups each were stimulated with the same GA lot. Each reaction was set up in triplicate.

After incubation at about 37° C. in a humidified $CO_2$ incubator for 6 hours, the cells were lysed for total RNA isolation. Total RNA was isolated from treated LN cells using SV 96 Total RNA Isolation System according to the manufacturer's protocol (Promega, Cat. #Z3500). Cells were washed once with Phosphate Buffered Saline (PBS) and lysed in RNA lysis buffer. The lysate was transferred to wells of the SV 96 binding plate. Samples were washed with RNA wash solution and treated with DNase. Total RNA was eluted with nuclease-free water from the binding plate.

cDNA was synthesized from each RNA sample in triplicate using High Capacity cDNA Reverse Transcription Kit (Life Technologies, formerly Applied Biosystems, Cat. #4368814) according to the manufacturer's protocol (Life Technologies). Reverse Transcription (RT) was performed by a Thermal Cycler (2720, Life Technologies) as follows:

| | Step 1 | Step 2 | Step 3 | Step 4 |
|---|---|---|---|---|
| Temperature (° C.) | 25 | 37 | 85 | 4 |
| Time (min) | 10 | 120 | 5 | ∞ |

After the reverse transcriptase reaction was completed, cDNA samples were used directly for real-time PCR to measure the response biomarker mRNA levels produced by the stimulated cells. To measure the response biomarker mRNA levels, TaqMan Universal PCR Master Mix (Cat. #4304437) and primers/probes for mouse cytokines IL-2 (Cat. #4331182; ID Mm00434256_m1), IL-4 (Cat. #4331182; ID Mm00445259_m1), IL-5 (Cat. #4331182; ID Mm00439646_m1), IL-10 (Cat. #4331182; ID Mm00439614_m1), IL-13 (Cat. #4331182; ID Mm00434204_m1), IFN-γ (Cat. #4331182; ID Mm01168134_m1) and TNF-α (Cat. #4331182; ID Mm00443260_g1) obtained from Life Technologies were used. The reference gene (internal control) mouse glyceraldehyde 3-phosphate dehydrogenase (GAPDH, Cat. #4352339E) also was obtained from Life Technologies. All probes for target genes contained FAM dye, and probes for the internal control contained VIC®/MGB dye. Samples will be prepared and run in 96-well plates using a Real-Time PCR system (7500, Life Technologies). This system allows direct detection of PCR-product formation by measuring the increase in fluorescent emission continuously during the PCR reaction. A relative quantitation method was used to analyze changes in mouse IL-2, IL-4, IL-5, IL-10, IL-13, IFN-γ and TNF-α expression in GA-treated samples relative to the untreated control (enriched DCCM-1 treated) samples. The Real-Time PCR program was:

| | UNG Incubation | AmpliTaq Gold Activation | 40 Cycles | |
|---|---|---|---|---|
| Temperature (° C.) | 50 | 95 | 95 | 60 |
| Time | 2 min | 10 min | 15 sec | 1 min |

The levels of mouse cytokine amplicons (IL-2, IL-4, IL-5, IL-10, IL-13, mIFN-γ and TNF-α) were normalized to internal probe levels (GAPDH) from the same samples. The following equations were used to calculate the relative increase in response to GA stimulation compared to the control sample:

$$\Delta C_T = C_{T\_target} - C_{T\_reference}$$

$$\Delta\Delta C_T = -\Delta C_{T\_Treated} - C_{T\_VC}$$

Increased response = $2^{-\Delta\Delta vc}$.
where
Targets = mouse IL-2, IL-4, IL-5, IL-10, IL-13, IFN-γ and TNF-α
Reference = GAPDH
Treatment = stimulation with GA, ConA or MBP
VC (Vehicle Control) = Incubation with enriched DCCM-1

Calculation of Mean Value:

$$\text{Mean Value } (\overline{X}) = \frac{\sum_{i=1}^{n} \text{individual data } (X)}{\text{number of data points } (n)}$$

Standard Deviation:

$$\text{Standard Deviation } (SD) = \sqrt{\frac{n \sum_{i=1}^{n} X_i^2 - \left(\sum_{i=1}^{n} X_i\right)^2}{n(n-1)}}$$

where X=individual data and n=number of data points.
Coefficient of Variation (CV, Precision):

$$\% \ CV = \left[\frac{\text{Standard Deviation } (SD)}{\text{Mean Value } (\overline{X})}\right] \times 100$$

The results are summarized in Table 17.

TABLE 17

Response Biomarker mRNA Produced in Response to GA Stimulation of LN Cells from Three Mouse Strains

| Response Biomarker mRNA Assayed | Immunization-Stimulation-Stimulation Conc. (μg/mL) | Group 1C: CD-1 mRNA Expression (fold change vs control) | Group 2C: BALB/cByJ mRNA Expression (fold change vs control) | Group 3C: SJL/J mRNA Expression (fold change vs control) |
|---|---|---|---|---|
| IL-2 | GA-GA-0.3 | 1.0 | 4.0 | 1.3 |
| | GA-GA-1 | 1.6 | 11.7 | 4.7 |
| | GA-GA-3 | 2.9 | 27.4 | 11.0 |
| | GA-GA-10 | 4.3 | 38.0 | 22.0 |
| | MBP-10 | 0.9 | 2.7 | 0.5 |
| | ConA-2.5 | 17.1 | 231.7 | 61.9 |
| IL-4 | GA-GA-0.3 | 1.6 | 4.2 | 2.0 |
| | GA-GA-1 | 4.7 | 6.5 | 5.2 |
| | GA-GA-3 | 6.1 | 10.1 | 10.0 |
| | GA-GA-10 | 11.2 | 9.8 | 15.3 |
| | MBP-10 | 0.6 | 1.1 | 0.5 |
| | ConA-2.5 | 23.8 | 27.2 | 29.2 |
| IL-5 | GA-GA-0.3 | 1.0 | 0.5 | 0.6 |
| | GA-GA-1 | 1.8 | 1.6 | 2.1 |
| | GA-GA-3 | 3.2 | 2.3 | 5.1 |
| | GA-GA-10 | 5.4 | 3.5 | 4.3 |
| | MBP-10 | 0.8 | 0.2 | 0.8 |
| | ConA-2.5 | 19.1 | 9.1 | 9.7 |
| IL-10 | GA-GA-0.3 | 0.7 | 0.7 | 0.5 |
| | GA-GA-1 | 0.8 | 1.0 | 0.6 |
| | GA-GA-3 | 0.9 | 1.3 | 0.5 |
| | GA-GA-10 | 0.9 | 1.3 | 0.8 |
| | MBP-10 | 0.7 | 1.0 | 0.3 |
| | ConA-2.5 | 0.4 | 0.9 | 0.4 |
| IL-13 | GA-GA-0.3 | 1.7 | 3.2 | 1.7 |
| | GA-GA-1 | 3.3 | 9.1 | 7.3 |
| | GA-GA-3 | 9.4 | 12.4 | 12.9 |
| | GA-GA-10 | 12.3 | 12.6 | 20.0 |
| | MBP-10 | 1.5 | 0.8 | 0.6 |
| | ConA-2.5 | 31.3 | 32.0 | 24.4 |
| IFN-γ | GA-GA-0.3 | 1.6 | 1.2 | 0.9 |
| | GA-GA-1 | 2.8 | 1.7 | 1.7 |
| | GA-GA-3 | 4.3 | 2.8 | 2.5 |
| | GA-GA-10 | 3.1 | 2.2 | 2.2 |
| | MBP-10 | 0.8 | 0.2 | 0.2 |
| | ConA-2.5 | 4.0 | 1.4 | 1.4 |
| TNF-α | GA-GA-0.3 | 1.0 | 0.1 | 0.8 |
| | GA-GA-1 | 1.1 | 1.0 | 0.9 |
| | GA-GA-3 | 1.4 | 0.8 | 0.9 |
| | GA-GA-10 | 1.1 | 0.5 | 0.8 |
| | MBP-10 | 0.8 | 0.8 | 0.3 |
| | ConA-2.5 | 0.6 | 0.8 | 0.7 |

$$\text{Response Ratio} = \frac{\text{Analyte Concentration Treated with } ConA, MBP \text{ or } GA}{\text{Analyte Concentration in } DCCM1 \text{ Medium}}$$

The data in Table 17 are graphed in FIGS. 3 to 13. A dose-dependent effect of GA stimulation concentration on mRNA levels was observed for many of the response biomarker mRNAs in LN cells from all three mouse strains.

Example IV. Validation of a Real-Time Polymerase Chain Reaction (PCR) Method for the Quantitative Measurement of Cytokine mRNA Levels Following Stimulation with GA in Lymph Node Cells from Mice Immunized with GA A real-time polymerase chain reaction (PCR) method was validated for the quantitative measurement of mRNA levels of cytokines in SJL/J mouse lymph node cells after GA stimulation.

Three experiments were conducted using one batch of GA (Mylan GMA). The primary LN cells were stimulated by incubation with 6 concentrations (0.3 to 20 μg/mL) of the GA for 6 hours at 37° C. Total RNA was isolated from LN cells stimulated with GA or controls. cDNA was synthesized from the RNA and the mRNA levels of seven mouse cytokines, IL-2, IL-4, IL-5, IL-10, IL-13, interferon (IFN)-γ and tumor necrosis factor (TNF)-α, were quantitatively measured by a real-time PCR method.

Five cytokines, IL-2, IL-4, IL-5, IL-13 and IFN-γ, were induced at the mRNA level in LN cells from GA immunized mice in response to GA stimulation. The levels of mRNA increased in a dose-dependent manner. The increase in the mRNA level of IL-2 following ConA stimulation (positive control) was greater than the increase induced by the highest concentration of GA (20 μg/mL) stimulation. There was no significant induction of mRNA levels of cytokines by the negative control MBP. The amplification of NTC (no template control) samples was below the detectable level. Table 18 shows the experimental design.

TABLE 18

Experiment Design Summary

| Group | Dose Route | # Animals/Gender | Stimulation | Dose of TA/mouse (Day 0) |
|---|---|---|---|---|
| 1 | Inject into four footpads | 6/F | Mylan GA + CFA | 250 μg |

TABLE 18-continued

Experiment Design Summary

| Group | Dose Route | # Animals/ Gender | Stimulation | Dose of TA/mouse (Day 0) |
|---|---|---|---|---|
| 2 | Inject into four footpads | 6/F | Mylan GA + CFA | 250 μg |
| 3 | Inject into four footpads | 6/F | Mylan GA + CFA | 250 μg |

Female SJL/J mice at 8-9 weeks of age were immunized by injection into four footpads using a 1 mL syringe with a 27-G, ½-inch needle. Each mouse received a total injection volume of 0.1 mL of GMA emulsified in CFA (about 10 μL into each of the front footpads and 40 μL into each of the hind footpads). Animals were immunized on Day 0. After injection, animals were placed back in their cages and housed ≤6 animals per cage.

Immunized animals were sacrificed by cervical dislocation on Day 10 following immunization. Lymph nodes in the axillary and popliteal regions from immunized mice were removed, pooled, and placed into sterile Petri dishes containing 5 mL of ice cold, sterile RPMI-1640 medium. The intact lymph nodes were washed three times in 5.0 mL of sterile RPMI 1640 medium and the LN cells isolated by pressing the LN with a sterile syringe plunger. The cell suspension was first passed through a 100 μm nylon cell strainer and then washed once with 40 mL of cold RPMI-1640 medium. After centrifugation at about 200×g for 10 minutes at 4° C., the cell pellet was re-suspended in 40 mL of RPMI-1640 medium for the second washing. After centrifugation at about 200×g for 10 minutes at 4° C., the cell pellet was re-suspended in 40 mL of DCCM-1 medium for cell counting. A Trypan blue exclusion method was used to determine the cell density of viable cells in the suspension. After cell counting, the LN cells were suspended in enriched DCCM-1 medium at density of $7.5 \times 10^6$ cells/mL. LN cells (0.12 mL) were plated into each well of 96-well tissue culture plates.

Dilutions of GA (Mylan GMA) were prepared using enriched DCCM-1 medium as the diluent. GA dilutions (0.12 mL) were added in the assigned wells of 96-well tissue culture plates. The same volume of LN cells (0.12 mL) isolated from immunized animals was added to the assigned wells. A positive control and a negative control were always performed in the same assay by treating LN cells with 2.5 μg/mL ConA and 10 μg/mL MBP, respectively. The LN cells with mock stimulation protocols (enriched DCCM-1 medium) were used to monitor the background mRNA level of a cytokine. Stimulations with Mylan GA are summarized in Table 19. The plates were incubated at 37° C. in a humidified 5% $CO_2$ incubator for 6 hr.

TABLE 19

GA Stimulation of LN Cells Isolated from Immunized Animals

| # of mice | LN Cells (Animal Stimulated with) | Stimulation | Concentration (μg/mL) |
|---|---|---|---|
| 6 | Mylan GA + CFA | GA Solution | 0.3, 1, 2.5, 5, 10 |
| | | ConA | 2.5 |
| | | MBP | 10 |
| | | Enriched DCCM-1 | 0 |

At the end of incubation time, culture medium from stimulated cells was removed by aspiration and the cells were lysed using Qiagen or Promega lysis buffer. The lysate was transferred to an RNeasy Mini column (Qiagen) or wells of the SV 96 Binding Plate (Promega) for RNA isolation and cDNA synthesis. All tested samples were run in triplicate.

The SV 96 Total RNA Isolation System (Promega; Cat. No. Z3505) was used for total RNA isolation. Assay procedures were carried out according to each manufacturer's protocol. RNA samples were stored at −70° C. until use. The High Capacity cDNA Reverse Transcription Kit (Qiagen; Cat. No. 4368814) was used for synthesis of cDNA. The assay procedure was carried out according to the manufacturer's protocol.

The mouse cytokine primers/probes used were IL-2 (Cat. #4331182; ID Mm00434256_m1), IL-4 (Cat. #4331182; ID Mm00445259_m1), IL-5 (Cat. #4331182; ID Mm00439646_m1), IL-10 (Cat. #4331182; ID Mm00439614_m1), IL-13 (Cat. #4331182; ID Mm00434204_m1), IFN-γ (Cat. #4331182; ID Mm01168134_m1) and TNF-α (Cat. #4331182; ID Mm00443260_g1). The reference gene primers/probe were for mouse GAPDH (LifeTechnologies Cat. No. 4352339E).

The cDNA samples were pipetted into assigned wells containing TaqMan Universal PCR Master Mix (LifeTechnologies Cat. #4304437) and target gene primers and probe with a multiple channel pipette. The plate was centrifuged at 2000 rpm for 2 minutes at 4° C. to spin down the contents and eliminate air bubbles. Samples were prepared and run in a 96-well plate using a Life Technologies Real-Time PCR system (previously Applied Biosystems; Model No. 7500) according to the manufacturer's recommendation. The mix for the reference gene was prepared in the same way using the reference gene primer.

A relative quantitation method was used to analyze changes in mIL-2, mIL-4, mIL-5, mIL-10, mIL-13, mIFN-γ and TNF-α expression in GA treated samples relative to the untreated control (Enriched DCCM-1 treated) samples using the following program:

| | UNG Incubation | AmpliTaq Gold Activation | 43 Cycles | |
|---|---|---|---|---|
| Temperature (° C.) | 50 | 95 | 95 | 60 |
| Time | 2 min | 10 min | 15 sec | 1 min |

Levels of mouse cytokine amplicons were normalized to an internal probe level (GAPDH) from the same samples. The following equations were used to calculate the relative increase in response to GA stimulation compared to the control sample (Enriched DCCM1 sample):

Calculation of Mean Value for $C_{T\_target}$ and $C_{T\_reference}$:

Where, Target: Il-2, IL-4, IL-5, IL-10, IL-13, IFN-γ and TNF-α

Reference: GAPDH $$\text{Mean Value } (\overline{X}) = \frac{\sum_{i=1}^{n} \text{individual data } (X)}{\text{number of data points } (n)}$$

Calculation of Standard Deviation for each mean $C_T$ value:

$$\text{Standard Deviation } (SD_\#) = \sqrt{\frac{n\sum_{i=1}^{n} X_i^2 - \left(\sum_{i=1}^{n} X_i\right)^2}{n(n-1)}}$$

where $SD_\#$=SD for $C_{T\_target}$ or $C_{T\_reference}$, X=individual data and n=number of data points.

Calculation of the $\Delta C_T$ value from the mean $C_T$ value:

$$\Delta C_T = C_{T\_target} - C_{T\_reference}$$

Calculation of the standard deviation of the $\Delta C_T$ value:

$$SD_{\Delta CT} = (SD^2_{target} + SD^2_{reference})$$

Where $Y^{1/2}$ is the square root of Y and $Y=SD^2_{target}+SD^2_{reference}$

Calculation of the $\Delta\Delta C_T$ value:

$$\Delta\Delta C_T = \Delta C_{T\_Treated} - C_{T\_VC}$$

Where, Treated: Incubated with GA, ConA or MBP
VC (Vehicle Control): Incubated with DCCM-1
Calculation of the standard deviation of the $\Delta\Delta C_T$ value:
Standard deviation of the $\Delta\Delta C_T$ value is the same as the standard deviation of the $\Delta C_T$ value.
Calculation of the induction fold and the induction range:
Induction fold=$2^{-\Delta\Delta C_T}$
Induction range=$2^{-A}$ to $2^{-B}$
Where $A=\Delta\Delta C_T+SD_{\Delta\Delta CT}$ and $B=\Delta\Delta C_T-SD_{\Delta\Delta CT}$ The calculations (mean, SD and associated calculations) were performed within Microsoft Excel® Version 2007 spreadsheets using full floating decimal point calculations unless specified. Some numbers in the tables were rounded for display. Based on these calculations, outliers were determined using the Percent Difference from the Mean Method. Percent difference from the mean was calculated by subtracting the mean $C_T$ value from each replicate $C_T$ value and then dividing by the mean $C_T$ value and multiplied by 100. When the percentage was ≥4.0% (absolute value), the replicate was an outlier. When the percentages of two replicates were ≥4.0% and the percent difference of the third replicate was ≥0.5%, the largest absolute value was designated as an outlier. When the percentages of two replicates were ≥4.0% and the third replicate was <0.5%, all values were used for calculation.

Sample analysis was completed in the analytical runs shown in Table 20.

TABLE 20

PCR Runs

| Experiment ID | Run Date | PCR Run Name | Description | Cytokine | Note |
|---|---|---|---|---|---|
| 1 | Jan. 16, 2013 | 12094_G1R1_011613_P2 | Sample Analysis | IL-2, IL-4 | P, F[a] |
|   | Jan. 17, 2013 | 12094_G1R2_011713_P2 | Sample Analysis | IL-5, IL-10 | P, P |
|   | Jan. 17, 2013 | 12094_G1R3_011713_P1 | Sample Analysis | IL-13, IFN-γ | P, F |
|   | Jan. 18, 2013 | 12094_G1R4_011813_P1 | Sample Analysis | TNF-α | P |
| 2 | Jan. 21, 2013 | 12094_G2R1_012113_P2 | Sample Analysis | IL-2, IL-4 | P, P |
|   | Jan. 21, 2013 | 12094_G2R2_012113_P1 | Sample Analysis | IL-13, IFN-γ | P, F |
|   | Jan. 22, 2013 | 12094_G2R3_012213_P2 | Sample Analysis | IL-5, IL-10 | P, F[b] |
|   | Jan. 22, 2013 | 12094_G2R4_012213_P1 | Sample Analysis | TNF-α | F[b] |
| 3 | Jan. 23, 2013 | 12094_G3R1_012313_P2 | Sample Analysis | IL-2, IL-4 | P, P |
|   | Jan. 23, 2013 | 12094_G3R2_012313_P1 | Sample Analysis | IL-13, IFN-γ | P, P |
|   | Jan. 23, 2013 | 12094_G3R3_012313_P2 | Sample Analysis | IL-5, IL-10 | F[a], P |
|   | Jan. 23, 2013 | 12094_G3R4_012313_P1 | Sample Analysis | TNF-α | P |
| 1 | Feb. 11, 2013 | 12094_G1Repeat_IL-4_021113 | Sample Analysis | IL-4 | F[a,c] |
| 2 | Feb. 12, 2013 | 12094_G2repeat_IL10_021213 | Sample Analysis | IL-10 | F[b,c] |
| 3 | Feb. 25, 2013 | 12094_G3_IL-5repeat_022513 | Sample Analysis | IL-5 | F[a,c] |

P: Pass,
F: Fail
[a]Fail: due to the negative control MBP failed acceptance criteria.
[b]Fail: due to the positive control ConA failed acceptance criteria.
[c]Repeated PCR runs for previously failed PCR runs.

Representative amplification plots for mouse IL-2, IL-4 and the reference gene GAPDH were generated. Each threshold was automatically set by the 7500 software v2.0.6 in the exponential phase of the amplification curve.

Low levels of mRNA expression for all tested cytokines were detected in mock-stimulated LN cells (incubated with DCCM-1). The mRNA levels of IL-2, IL-4, IL-5, IL-13 and IFN-γ, increased in LN cells treated with GA compared to the DCCM-1 control, and increases were dose-dependent and saturable. The mRNA levels of IL-10 and TNF-α were weakly or not induced in response to in vitro GA stimulation in SJL/J mice.

Mouse IL-2 mRNA Expression

Mouse IL-2 mRNA was induced in LN cells stimulated with GA in all three experiments. The induction of IL-2 mRNA after stimulation with 20 μg/mL GA was 31.7, 27.8 and 42.0-fold in Exp 1, 2 and 3, respectively (Table 21).

TABLE 21

Expression of Mouse IL-2 by Primary LN Cells in Response to GA Stimulation

| Group | Stimulation | Conc. (μg/mL) | IL-2 mRNA Fold Change | Induction Range |
|---|---|---|---|---|
| Experiment 1 | GA-0.3 | 0.3 | 2.1 | 1.5-2.8 |
|   | GA-1 | 1.0 | 7.4 | 5.8-9.5 |
|   | GA-2.5 | 2.5 | 16.1 | 13.8-18.8 |
|   | GA-5 | 5.0 | 17.1 | 13.8-21.3 |
|   | GA-10 | 10 | 27.2 | 22.4-33.0 |
|   | GA-20 | 20 | 31.7 | 25.2-39.9 |
|   | DCCM1 | NA | 1.0 | 0.7-1.5 |

TABLE 21-continued

Expression of Mouse IL-2 by Primary LN Cells in Response to GA Stimulation

| Group | Stimulation | Conc. (µg/mL) | IL-2 mRNA Fold Change | Induction Range |
|---|---|---|---|---|
| | MBP | 10 | 1.0 | 0.6-1.5 |
| | ConA | 2.5 | 147.1 | 130-166.5 |
| Experiment 2 | GA-0.3 | 0.3 | 2.9 | 2.2-3.7 |
| | GA-1 | 1.0 | 7.4 | 5.6-9.6 |
| | GA-2.5 | 2.5 | 19.6 | 17.5-22.0 |
| | GA-5 | 5.0 | 26.7 | 22.8-31.3 |
| | GA-10 | 10 | 36.8 | 31.1-43.5 |
| | GA-20 | 20 | 27.8 | 18.1-42.7 |
| | DCCM1 | NA | 1.0 | 0.7-1.4 |
| | MBP | 10 | 0.9 | 0.8-1.1 |
| | ConA | 2.5 | 72.0 | 56.6-91.6 |
| Experiment 3 | GA-0.3 | 0.3 | 2.2 | 1.8-2.6 |
| | GA-1 | 1.0 | 9.0 | 8.2-9.9 |
| | GA-2.5 | 2.5 | 18.0 | 14.7-22.0 |
| | GA-5 | 5.0 | 25.1 | 23-27.5 |
| | GA-10 | 10 | 32.9 | 26.7-40.7 |
| | GA-20 | 20 | 42.0 | 35.4-49.9 |
| | DCCM1 | NA | 1.0 | 0.8-1.3 |
| | MBP | 10 | 0.8 | 0.6-1.1 |
| | ConA | 2.5 | 188.6 | 148.6-239.4 |

(Real-time PCR runs G1R1_011613_P2, G2R1_012113_P2, G3R1_012313_P2)

Mouse IL-4 mRNA Expression

Mouse IL-4 mRNA was induced in LN cells stimulated with GA in all three experiments. The induction of IL-4 mRNA after stimulation with 20 µg/mL GA was 41.3, 11.8 and 27.6-fold in Exp 1, 2 and 3, respectively (Table 22).

TABLE 22

Expression of Mouse IL-4 by Primary LN Cells in Response to GA Stimulation

| Group | Stimulation | Conc. (µg/mL) | IL-4 mRNA Fold Change | SD |
|---|---|---|---|---|
| Experiment 1 | GA-0.3 | 0.3 | 4.5 | 3.5-6.0 |
| | GA-1 | 1.0 | 17.5 | 12.5-24.5 |
| | GA-2.5 | 2.5 | 25.5 | 18.3-35.6 |
| | GA-5 | 5.0 | 34.1 | 28-41.5 |
| | GA-10 | 10 | 41.1 | 35-48.3 |
| | GA-20 | 20 | 41.3 | 28.7-59.6 |
| | DCCM1 | NA | 1.0 | 0.7-1.4 |
| | MBP | 10 | 2.7 | 1.8-4.2 |
| | ConA | 2.5 | 148.6 | 135.4-163.1 |
| Experiment 2 | GA-0.3 | 0.3 | 3.6 | 2.8-4.8 |
| | GA-1 | 1.0 | 5.8 | 4.8-7.0 |
| | GA-2.5 | 2.5 | 14.6 | 13.3-15.9 |
| | GA-5 | 5.0 | 17.5 | 13-23.6 |
| | GA-10 | 10 | 20.5 | 17.5-24.0 |
| | GA-20 | 20 | 11.8 | 7.3-19.0 |
| | DCCM1 | NA | 1.0 | 0.5-1.9 |
| | MBP | 10 | 0.8 | 0.5-1.4 |
| | ConA | 2.5 | 21.0 | 16.4-26.8 |
| Experiment 3 | GA-0.3 | 0.3 | 5.4 | 4.2-6.8 |
| | GA-1 | 1.0 | 10.5 | 8.8-12.5 |
| | GA-2.5 | 2.5 | 18.4 | 14.9-22.6 |
| | GA-5 | 5.0 | 26.0 | 24.3-27.7 |
| | GA-10 | 10 | 28.0 | 20.9-37.4 |
| | GA-20 | 20 | 27.6 | 25.6-29.9 |
| | DCCM1 | NA | 1.0 | 0.7-1.5 |
| | MBP | 10 | 1.1 | 0.8-1.4 |
| | ConA | 2.5 | 53.8 | 43.6-66.3 |

(Real-time PCR runs G1R1_011613_P2, G2R1_012113_P2, G3R1_012313_P2)

Mouse IL-5 mRNA Expression

Mouse IL-5 mRNA was induced in LN cells stimulated with GA in all three experiments. After stimulation with 20 µg/mL GA, 5.2, 5.3 and 15.2-fold induction of IL-5 mRNA was observed in Exp 1, 2 and 3, respectively (Table 23).

TABLE 23

Expression of Mouse IL-5 by Primary LN Cells in Response to GA Stimulation

| Group | Stimulation | Conc. (µg/mL) | IL-5 mRNA Fold Change | SD |
|---|---|---|---|---|
| Experiment 1 | GA-0.3 | 0.3 | 1.7 | 1.1-2.6 |
| | GA-1 | 1.0 | 1.6 | 0.8-3 |
| | GA-2.5 | 2.5 | 3.7 | 2.1-6.3 |
| | GA-5 | 5.0 | 2.8 | 1.2-6.1 |
| | GA-10 | 10 | 2.6 | 1.1-6 |
| | GA-20 | 20 | 5.2 | 3.3-8.2 |
| | DCCM1 | NA | 1.0 | 0.7-1.4 |
| | MBP | 10 | 0.8 | 0.5-1.4 |
| | ConA | 2.5 | 22.4 | 17-29.4 |
| Experiment 2 | GA-0.3 | 0.3 | 0.8 | 0.5-1.3 |
| | GA-1 | 1.0 | 1.7 | 0.9-3.1 |
| | GA-2.5 | 2.5 | 3.7 | 2.4-5.8 |
| | GA-5 | 5.0 | 4.4 | 3.6-5.4 |
| | GA-10 | 10 | 5.4 | 3.9-7.4 |
| | GA-20 | 20 | 5.3 | 3-9.5 |
| | DCCM1 | NA | 1.0 | 0.5-1.9 |
| | MBP | 10 | 0.8 | 0.5-1.1 |
| | ConA | 2.5 | 11.3 | 8-16 |
| Experiment 3 | GA-0.3 | 0.3 | 1.1 | 1.1-1.2 |
| | GA-1 | 1.0 | 4.0 | 2.8-5.8 |
| | GA-2.5 | 2.5 | 7.6 | 6.1-9.4 |
| | GA-5 | 5.0 | 11.2 | 9.4-13.3 |
| | GA-10 | 10 | 10.0 | 7-14.5 |
| | GA-20 | 20 | 15.2 | 12.3-18.8 |
| | DCCM1 | NA | 1.0 | 0.7-1.5 |
| | MBP | 10 | 2.6 | 2.1-3.1 |
| | ConA | 2.5 | 31.0 | 25.9-37.1 |

(Real-time PCR runs G1R2_011713_P2, G2R3_012213_P2, G3R3_012313_P2)

Mouse IL-10 mRNA Expression

No induction of mouse IL-10 mRNA was observed in LN cells in response to stimulation with GA compared to the mock-stimulated control in any experiment (Table 24).

TABLE 24

Expression of Mouse IL-10 from Primary LN Cells in Response to GA Stimulation

| Group | Stimulation | Conc. (µg/mL) | IL-10 mRNA Fold Change | SD |
|---|---|---|---|---|
| Experiment 1 | GA-0.3 | 0.3 | 0.9 | 0.7-1.3 |
| | GA-1 | 1.0 | 1.0 | 0.6-1.5 |
| | GA-2.5 | 2.5 | 0.8 | 0.6-1 |
| | GA-5 | 5.0 | 0.8 | 0.6-0.9 |
| | GA-10 | 10 | 0.9 | 0.6-1.4 |
| | GA-20 | 20 | 1.0 | 0.7-1.6 |
| | DCCM1 | NA | 1.0 | 0.7-1.5 |
| | MBP | 10 | 1.1 | 0.9-1.3 |
| | ConA | 2.5 | 1.2 | 1-1.5 |
| Experiment 2 | GA-0.3 | 0.3 | 0.9 | 0.7-1.1 |
| | GA-1 | 1.0 | 0.7 | 0.5-0.9 |
| | GA-2.5 | 2.5 | 0.8 | 0.6-1.1 |
| | GA-5 | 5.0 | 0.8 | 0.7-1 |
| | GA-10 | 10 | 1.2 | 1-1.4 |
| | GA-20 | 20 | 0.8 | 0.5-1.3 |
| | DCCM1 | NA | 1.0 | 0.6-1.7 |
| | MBP | 10 | 0.7 | 0.6-1 |
| | ConA | 2.5 | 0.5 | 0.4-0.7 |
| Experiment 3 | GA-0.3 | 0.3 | 1.2 | 1.1-1.2 |
| | GA-1 | 1.0 | 1.1 | 0.9-1.3 |
| | GA-2.5 | 2.5 | 0.9 | 0.9-0.9 |
| | GA-5 | 5.0 | 1.0 | 0.9-1.1 |
| | GA-10 | 10 | 1.2 | 1-1.4 |
| | GA-20 | 20 | 1.3 | 1.1-1.5 |
| | DCCM1 | NA | 1.0 | 0.8-1.3 |

TABLE 24-continued

Expression of Mouse IL-10 from Primary LN Cells in Response to GA Stimulation

| Group | Stimulation | Conc. (μg/mL) | IL-10 mRNA Fold Change | SD |
|---|---|---|---|---|
| | MBP | 10 | 1.0 | 0.8-1.3 |
| | ConA | 2.5 | 1.6 | 1.4-1.9 |

(Real-time PCR runs G1R2_011713_P2, G2R3_012213_P2, G3R3_012313_P2)

Mouse IL-13 mRNA Expression

Mouse IL-13 mRNA was induced in LN cells stimulated with GA in all three experiments. The induction of IL-13 mRNA after stimulation with 20 μg/mL was 17.6, 21.3 and 33.9-fold for Exp 1, 2 and 3, respectively (Table 25).

TABLE 25

Expression of Mouse IL-13 from Primary LN Cells in Response to GA Stimulation

| Group | Stimulation | Conc. (μg/mL) | IL-13 mRNA Fold Change | SD |
|---|---|---|---|---|
| Experiment 1 | GA-0.3 | 0.3 | 3.6 | 2.3-5.6 |
| | GA-1 | 1.0 | 8.7 | 5.3-14.4 |
| | GA-2.5 | 2.5 | 13.1 | 8.7-19.8 |
| | GA-5 | 5.0 | 12.2 | 7.8-19.1 |
| | GA-10 | 10 | 16.6 | 13.5-20.4 |
| | GA-20 | 20 | 17.6 | 12.5-24.8 |
| | DCCM1 | NA | 1.0 | 0.5-2.1 |
| | MBP | 10 | 0.9 | 0.6-1.5 |
| | ConA | 2.5 | 40.9 | 30.6-54.8 |
| Experiment 2 | GA-0.3 | 0.3 | 4.6 | 3.4-6.3 |
| | GA-1 | 1.0 | 8.6 | 6.8-10.9 |
| | GA-2.5 | 2.5 | 21.5 | 16.7-27.7 |
| | GA-5 | 5.0 | 28.8 | 22.5-36.7 |
| | GA-10 | 10 | 30.4 | 23.6-39.2 |
| | GA-20 | 20 | 21.3 | 9.4-47.9 |
| | DCCM1 | NA | 1.0 | 0.6-1.7 |
| | MBP | 10 | 1.4 | 0.9-2 |
| | ConA | 2.5 | 32.4 | 24.5-42.9 |
| Experiment 3 | GA-0.3 | 0.3 | 2.5 | 1.2-5.3 |
| | GA-1 | 1.0 | 6.5 | 5.2-8.3 |
| | GA-2.5 | 2.5 | 14.7 | 12.8-16.9 |
| | GA-5 | 5.0 | 23.8 | 20.3-27.8 |
| | GA-10 | 10 | 18.9 | 14.6-24.6 |
| | GA-20 | 20 | 33.9 | 25.7-44.8 |
| | DCCM1 | NA | 1.0 | 0.5-2 |
| | MBP | 10 | 1.2 | 0.8-1.7 |
| | ConA | 2.5 | 50.9 | 41.2-62.9 |

(Real-time PCR runs G1R3_011713_P1, G2R2_012113_P1, G3R2_012313_P1)

Mouse IFN-γ mRNA Expression

Weak induction of IFN-γ mRNA was observed in LN cells in response to in vitro GA stimulation. LN cells from the three experiments displayed a similar pattern in response to GA stimulation. The induction of IFN-γ mRNA reached ≥2 fold following stimulation with 2.5 to 10 μg/mL GA. However, after stimulation with 20 μg/mL GA, the levels of IFN-γ mRNA expression dropped to a level similar to that observed after stimulation with 0.3 μg/mL GA stimulation in all three experiments (Table 26).

TABLE 26

Expression of Mouse IFN-γ from Primary LN Cells in Response to GA Stimulation

| Group | Stimulation | Conc. (μg/mL) | IFN-γ mRNA Fold Change | SD |
|---|---|---|---|---|
| Experiment 1 | GA-0.3 | 0.3 | 1.1 | 0.6-1.8 |
| | GA-1 | 1.0 | 1.8 | 1.2-2.8 |
| | GA-2.5 | 2.5 | 2.5 | 2-3.1 |
| | GA-5 | 5.0 | 2.0 | 1.6-2.5 |
| | GA-10 | 10 | 2.4 | 1.9-3.1 |
| | GA-20 | 20 | 1.1 | 0.8-1.7 |
| | DCCM1 | NA | 1.0 | 0.8-1.3 |
| | MBP | 10 | 0.8 | 0.5-1 |
| | ConA | 2.5 | 1.9 | 1.4-2.5 |
| Experiment 2 | GA-0.3 | 0.3 | 1.6 | 1.2-2.1 |
| | GA-1 | 1.0 | 2.0 | 1.6-2.5 |
| | GA-2.5 | 2.5 | 3.2 | 2.9-3.5 |
| | GA-5 | 5.0 | 3.3 | 2.9-3.8 |
| | GA-10 | 10 | 3.2 | 2.6-3.9 |
| | GA-20 | 20 | 1.2 | 0.4-3.5 |
| | DCCM1 | NA | 1.0 | 0.7-1.5 |
| | MBP | 10 | 1.3 | 1.1-1.4 |
| | ConA | 2.5 | 1.6 | 1-2.7 |
| Experiment 3 | GA-0.3 | 0.3 | 1.5 | 1.2-1.9 |
| | GA-1 | 1.0 | 2.3 | 2.1-2.5 |
| | GA-2.5 | 2.5 | 2.4 | 1.9-2.9 |
| | GA-5 | 5.0 | 2.5 | 2.1-2.9 |
| | GA-10 | 10 | 2.4 | 1.9-3 |
| | GA-20 | 20 | 1.7 | 1.3-2.3 |
| | DCCM1 | NA | 1.0 | 0.8-1.2 |
| | MBP | 10 | 1.1 | 0.9-1.3 |
| | ConA | 2.5 | 2.6 | 1.6-4.3 |

(Real-time PCR runs G1R3_011713_P1, G2R2_012113_P1, G3R2_012313_P1)

Mouse TNF-α mRNA Expression

No induction of TNF-α mRNA was observed in LN cells after stimulation with GA compared to the mock-stimulated control (all <2 fold) (Table 27).

TABLE 27

Expression of Mouse TNF-α from Primary LN Cells in Response to GA Stimulation

| Group | Stimulation | Conc. (μg/mL) | TNF-α mRNA Fold Change | SD |
|---|---|---|---|---|
| Experiment 1 | GA-0.3 | 0.3 | 0.8 | 0.7-0.9 |
| | GA-1 | 1.0 | 1.0 | 0.7-1.5 |
| | GA-2.5 | 2.5 | 1.3 | 1-1.8 |
| | GA-5 | 5.0 | 1.1 | 0.8-1.6 |
| | GA-10 | 10 | 0.9 | 0.7-1.2 |
| | GA-20 | 20 | 1.5 | 0.8-2.9 |
| | DCCM1 | NA | 1.0 | 0.5-1.8 |
| | MBP | 10 | 1.0 | 0.8-1.4 |
| | ConA | 2.5 | 1.9 | 1.3-2.7 |
| Experiment 2 | GA-0.3 | 0.3 | 1.2 | 1.1-1.4 |
| | GA-1 | 1.0 | 1.1 | 0.9-1.3 |
| | GA-2.5 | 2.5 | 1.8 | 1.6-2.1 |
| | GA-5 | 5.0 | 1.6 | 1.5-1.7 |
| | GA-10 | 10 | 1.7 | 1.5-1.9 |
| | GA-20 | 20 | 1.1 | 0.6-2.1 |
| | DCCM1 | NA | 1.0 | 0.7-1.4 |
| | MBP | 10 | 1.1 | 0.9-1.4 |
| | ConA | 2.5 | 0.8 | 0.6-1 |
| Experiment 3 | GA-0.3 | 0.3 | 1.2 | 1.1-1.3 |
| | GA-1 | 1.0 | 1.3 | 1.1-1.6 |
| | GA-2.5 | 2.5 | 1.2 | 1.1-1.2 |
| | GA-5 | 5.0 | 1.1 | 1-1.3 |
| | GA-10 | 10 | 1.2 | 1.1-1.4 |
| | GA-20 | 20 | 1.3 | 0.8-2 |
| | DCCM1 | NA | 1.0 | 0.8-1.3 |
| | MBP | 10 | 1.1 | 1-1.2 |
| | ConA | 2.5 | 1.6 | 1.3-1.8 |

(Real-time PCR runs G1R4_011813_P1, G2R4_012213_P1, G3R4_012313_P1)

Thus, mRNA levels of five of the seven cytokines, IL-2, IL-4, IL-5, IL-13 and IFN-γ, were induced in LN cells in response to GA stimulation. Expression of IL-10 and TNF-α mRNA did not change significantly. The amplification of NTC (no template control) samples was below the detectable level for all PCR runs. LN cells from all groups were tested for their responses to ConA and MBP. Expression levels of all cytokine mRNAs from ConA-treated LN cells (2.5 μg/mL) were greater than the expression levels after stimulation with the highest concentration (20 μg/mL) of GA, except for IL-10 mRNA (Exp 1, Table 24) and TNF-α (Exp 3, Table 27). Expression levels of cytokine mRNAs in response to MBP treatment were ≤2 fold in all PCR runs, except IL-4 (Exp 1, Table 22) and IL-5 (Exp 3, Table 23). Three PCR runs (IL-10 for ConA and IL-4 & IL-5 for MBP) were repeated and similar results obtained compared to the results from the original runs regardless of response to ConA or MBP treatments (data not shown), suggesting that the results and assays were consistent. The results from this study showed unique cytokine induction profiles (inducible vs. non-inducible) and consistent induction magnitude (mild to significant) for the tested cytokines from three independent experiments, suggesting that the real-time PCR method is a reproducible method for quantitative measurement of cytokine mRNA levels in LN cells from GA-immunized mice after GA stimulation.

Conclusion

A highly sensitive quantitative real-time PCR method was validated for profiling and quantifying cytokine mRNA in LN cells from GA-immunized mice following GA stimulation in vitro. Relative quantification analysis was carried out by the comparative $C_T$ method using GAPDH as a housekeeping gene. The stimulation of GA-immunized mouse LN cells with different concentrations of GA resulted in no induction of IL-10, TNF-α, weak induction of IFN-γ, moderate induction of IL-5, and robust induction of IL-2, IL-4 and IL-13 mRNA levels compared with those in the unstimulated LN cells. The results indicate that the method is sensitive, reproducible, and efficient to measure cytokine mRNA expression in LN cells in response to GA stimulation.

Example V. Quantitative Measurement of Cytokine mRNA Levels in Mouse Lymph Node Cells after Stimulation with Test GA and Reference GA Lots Using a Real-Time Polymerase Chain Reaction A real-time polymerase chain reaction method was used to measure the expression of cytokine mRNA in GA-stimulated LN cells from GA-immunized SJL/J mice. Normalization of expression with two different housekeeping genes, GAPDH and β-actin, was tested.

Each group consisted of six female SJL/J mice immunized by injection in all four footpads with a total dose of 250 μg of one lot of GA, or mannitol and no GA. Three Copaxone batches and three GMA batches were used to immunize the mice. CFA was included in both GA and mannitol immunizations. Ten days following immunization, LN cell samples isolated from the immunized mice were each stimulated with a concentration of a Copaxone lot and a GMA lot. A positive control of 2.5 μg/mL ConA treated LN cells and a negative control of 10 μg/mL MBP treated cells were included in each group.

In the initial run, a lack of reproducibility was observed when cytokine mRNA levels were normalized to GAPDH mRNA levels. Therefore, the Q-PCR analysis was repeated on the samples, measuring levels of IL-2, IL-4, IL-5, and IL-13, using both GAPDH and β-actin as reference gene. The experimental design for the repeated run is shown in Table 28.

TABLE 28

Experimental Design Summary (GAPDH and Act-β normalization)

| | | LN Cell Stimulation | |
|---|---|---|---|
| | Mice Immunization | | Concentrations |
| Group ID | GA-C/GA-M (250 μg/mouse) + CFA | GA Solution (Lot Number) | in Wells (μg/mL) |
| 3 | GA-M2 (Mylan GMA) | GA-M2 | 0.3, 1, 2.5, 5, 10, 20 |
| | | GA-C2 | 0.3, 1, 2.5, 5, 10, 20 |
| 4 | GA-C2 (Copaxone) | GA-M2 | 0.3, 1, 2.5, 5, 10, 20 |
| | | GA-C2 | 0.3, 1, 2.5, 5, 10, 20 |

The RNA isolation and analysis procedures were similar to those described in Example IV. The expression levels of mouse IL-2, IL-4, IL-5 and IL-13 mRNA observed are summarized below in Tables 29 to 36. As shown by the data in Tables 30, 32, 34 and 36, a lack of reproducibility in the findings again was observed when cytokine mRNA levels were normalized to GAPDH mRNA for all cytokines except IL-13. However when β-actin was used as the reference housekeeping gene, comparable stimulation by COP and GMA was observed for each cytokine mRNA analyzed.

TABLE 29

Expression of Mouse IL-2 from Primary LN Cells in Response to GA Stimulation (normalized to Actβ)

| Group ID | Drug Stimulation | GA Conc. (μg/mL) | IL-2 mRNA Fold Change | Range |
|---|---|---|---|---|
| 3 | Mylan GA (M2) | 0.3 | 1.7 | 1.4-2.1 |
| | | 1 | 4.8 | 3.9-5.9 |
| | | 2.5 | 11.5 | 10.4-12.7 |
| | | 5 | 15.7 | 10.2-24.3 |
| | | 10 | 21.2 | 16.6-27.1 |
| | | 20 | 27.4 | 22.9-32.8 |
| | Copaxone (C2) | 0.3 | 1.9 | 1.8-2.1 |
| | | 1 | 5.8 | 4.7-7.2 |
| | | 2.5 | 13.6 | 8.8-20.9 |
| | | 5 | 17.5 | 16-19.2 |
| | | 10 | 23.9 | 20.1-28.3 |
| | | 20 | 27.6 | 21-36.1 |
| | MBP | 10 | 1.2 | 1-1.5 |
| | ConA | 2.5 | 123.4 | 115.9-131.4 |
| 4 | Mylan GA (M2) | 0.3 | 1.6 | 1.4-2 |
| | | 1 | 5.3 | 3.6-7.7 |
| | | 2.5 | 12.3 | 6-25.1 |
| | | 5 | 16.9 | 14.5-19.6 |
| | | 10 | 20.4 | 15.7-26.4 |
| | | 20 | 29.0 | 24.8-33.8 |
| | Copaxone (C2) | 0.3 | 1.6 | 1.5-1.8 |
| | | 1 | 4.8 | 4.1-5.5 |
| | | 2.5 | 13.3 | 11.7-15.1 |
| | | 5 | 20.0 | 18.2-22 |
| | | 10 | 23.8 | 18.8-30.2 |
| | | 20 | 29.1 | 25-33.8 |
| | MBP | 10 | 0.8 | 0.6-1 |
| | ConA | 2.5 | 105.0 | 64.2-171.7 |

TABLE 30

Expression of Mouse IL-2 from Primary LN Cells in Response to GA Stimulation (normalized to GAPDH)

| Group ID | Drug Stimulation | GA Conc. (µg/mL) | IL-2 mRNA Fold Change | Range |
|---|---|---|---|---|
| 3 | Mylan GA (M2) | 0.3 | 2.0 | 1.4-2.9 |
|   |   | 1 | 5.4 | 3.8-7.6 |
|   |   | 2.5 | 15.2 | 8.8-26.2 |
|   |   | 5 | 29.9 | 19.2-46.3 |
|   |   | 10 | 38.9 | 26.2-57.8 |
|   |   | 20 | 52.7 | 41.6-66.7 |
|   | Copaxone (C2) | 0.3 | 1.2 | 1.2-1.3 |
|   |   | 1 | 11.3 | 9-14.2 |
|   |   | 2.5 | 42.2 | 29-61.5 |
|   |   | 5 | 78.4 | 57.1-107.7 |
|   |   | 10 | 93.9 | 68.3-129.1 |
|   |   | 20 | 119.5 | 87-164.2 |
|   | MBP | 10 | 0.7 | 0.4-1.2 |
|   | ConA | 2.5 | 149.4 | 98.6-226.3 |
| 4 | Mylan GA (M2) | 0.3 | 2.1 | 1.5-3 |
|   |   | 1 | 4.5 | 3.4-5.8 |
|   |   | 2.5 | 11.9 | 10-14.2 |
|   |   | 5 | 33.5 | 23.2-48.4 |
|   |   | 10 | 58.9 | 36.3-95.4 |
|   |   | 20 | 48.4 | 28.5-82.4 |
|   | Copaxone (C2) | 0.3 | 1.5 | 1.3-1.8 |
|   |   | 1 | 6.3 | 5.2-7.6 |
|   |   | 2.5 | 16.3 | 11.8-22.5 |
|   |   | 5 | 30.0 | 23.7-38 |
|   |   | 10 | 36.2 | 25.1-52.1 |
|   |   | 20 | 43.0 | 23.7-77.8 |
|   | MBP | 10 | 1.3 | 0.7-2.2 |
|   | ConA | 2.5 | 84.8 | 71.6-100.4 |

TABLE 31

Expression of Mouse IL-4 from Primary LN Cells in Response to GA Stimulation (normalized to Actβ)

| Group ID | Drug Stimulation | GA Conc. (µg/mL) | IL-4 mRNA Fold Change | Range |
|---|---|---|---|---|
| 3 | Mylan GA (M2) | 0.3 | 2.5 | 1.7-3.7 |
|   |   | 1 | 6.9 | 3.7-13.1 |
|   |   | 2.5 | 9.0 | 5.1-15.7 |
|   |   | 5 | 18.3 | 12.3-27.2 |
|   |   | 10 | 20.2 | 15.7-26 |
|   |   | 20 | 20.8 | 15.6-27.8 |
|   | Copaxone (C2) | 0.3 | 2.6 | 1.6-4.4 |
|   |   | 1 | 8.5 | 7.2-10.1 |
|   |   | 2.5 | 15.3 | 14.4-16.3 |
|   |   | 5 | 21.8 | 18.4-26 |
|   |   | 10 | 28.6 | 22.7-36.1 |
|   |   | 20 | 33.3 | 22.9-48.3 |
|   | MBP | 10 | 0.8 | 0.5-1.2 |
|   | ConA | 2.5 | 43.6 | 28.4-66.9 |
| 4 | Mylan GA (M2) | 0.3 | 3.1 | 2.1-4.5 |
|   |   | 1 | 7.6 | 5.1-11.3 |
|   |   | 2.5 | 12.9 | 8.6-19.2 |
|   |   | 5 | 18.8 | 9.6-37.1 |
|   |   | 10 | 21.9 | 14.4-33.1 |
|   |   | 20 | 17.6 | 15-20.8 |
|   | Copaxone (C2) | 0.3 | 3.8 | 2-7 |
|   |   | 1 | 8.7 | 4.9-15.4 |
|   |   | 2.5 | 14.3 | 11.2-18.2 |
|   |   | 5 | 22.6 | 18.1-28.2 |
|   |   | 10 | 24.5 | 18.9-31.9 |
|   |   | 20 | 24.2 | 14.4-40.4 |
|   | MBP | 10 | 2.4 | 2-3 |
|   | ConA | 2.5 | 48.3 | 40.4-57.9 |

TABLE 32

Expression of Mouse IL-4 from Primary LN Cells in Response to GA Stimulation (normalized to GAPDH)

| Group ID | Drug Stimulation | GA Conc. (µg/mL) | IL-4 mRNA Fold Change | Range |
|---|---|---|---|---|
| 3 | Mylan GA (M2) | 0.3 | 3.8 | 2.8-5.2 |
|   |   | 1 | 9.2 | 7-12.1 |
|   |   | 2.5 | 22.3 | 12.7-39.4 |
|   |   | 5 | 42.8 | 28.3-64.8 |
|   |   | 10 | 47.8 | 32.6-70.2 |
|   |   | 20 | 49.6 | 38.8-63.5 |
|   | Copaxone (C2) | 0.3 | 3.7 | 2.3-6.1 |
|   |   | 1 | 24.7 | 17.9-34.1 |
|   |   | 2.5 | 64.3 | 48.2-85.8 |
|   |   | 5 | 114.8 | 83-158.8 |
|   |   | 10 | 146.6 | 116-185.3 |
|   |   | 20 | 126.1 | 107.5-147.8 |
|   | MBP | 10 | 0.7 | 0.7-0.8 |
|   | ConA | 2.5 | 87.9 | 65.7-117.5 |
| 4 | Mylan GA (M2) | 0.3 | 4.6 | 3.2-6.7 |
|   |   | 1 | 8.9 | 4.5-17.3 |
|   |   | 2.5 | 12.2 | 8.9-16.7 |
|   |   | 5 | 35.3 | 19.9-62.7 |
|   |   | 10 | 55.7 | 35.5-87.4 |
|   |   | 20 | 35.1 | 23.1-53.3 |
|   | Copaxone (C2) | 0.3 | 2.9 | 2.6-3.2 |
|   |   | 1 | 7.4 | 5.3-10.4 |
|   |   | 2.5 | 14.7 | 8.6-25.1 |
|   |   | 5 | 35.2 | 23.3-53.2 |
|   |   | 10 | 26.3 | 16.1-42.9 |
|   |   | 20 | 28.2 | 16.2-48.9 |
|   | MBP | 10 | 1.3 | 0.7-2.2 |
|   | ConA | 2.5 | 84.8 | 71.6-100.4 |

TABLE 33

Expression of Mouse IL-5 from Primary LN Cells in Response to GA Stimulation (normalized to Actβ)

| Group ID | Drug Stimulation | GA Conc. (µg/mL) | IL-5 mRNA Fold Change | Range |
|---|---|---|---|---|
| 3 | Mylan GA (M2) | 0.3 | 0.6 | 0.5-0.9 |
|   |   | 1 | 2.2 | 1.2-3.9 |
|   |   | 2.5 | 3.3 | 1.3-8.6 |
|   |   | 5 | 5.3 | 3.5-8 |
|   |   | 10 | 10.3 | 8.6-12.2 |
|   |   | 20 | 9.2 | 6.5-13 |
|   | Copaxone (C2) | 0.3 | 0.9 | 0.6-1.3 |
|   |   | 1 | 2.0 | 1.1-3.8 |
|   |   | 2.5 | 7.6 | 5.3-10.8 |
|   |   | 5 | 5.1 | 2.7-9.6 |
|   |   | 10 | 8.9 | 6.8-11.7 |
|   |   | 20 | 9.3 | 7.4-11.7 |
|   | MBP | 10 | 0.6 | 0.3-1.2 |
|   | ConA | 2.5 | 19.1 | 11.3-32.2 |
| 4 | Mylan GA (M2) | 0.3 | 0.6 | 0.5-0.7 |
|   |   | 1 | 1.1 | 0.4-2.6 |
|   |   | 2.5 | 3.7 | 1.6-8.5 |
|   |   | 5 | 3.9 | 2.4-6.4 |
|   |   | 10 | 9.9 | 8.4-11.6 |
|   |   | 20 | 6.0 | 2.9-12.7 |
|   | Copaxone (C2) | 0.3 | 0.9 | 0.7-1.2 |
|   |   | 1 | 2.6 | 2-3.5 |
|   |   | 2.5 | 2.6 | 1.4-4.5 |
|   |   | 5 | 2.4 | 1.2-4.7 |
|   |   | 10 | 4.9 | 4.1-5.9 |
|   |   | 20 | 10.3 | 7.2-14.8 |
|   | MBP | 10 | 1.1 | 0.7-1.7 |
|   | ConA | 2.5 | 27.8 | 23.3-33.2 |

TABLE 34

Expression of Mouse IL-5 from Primary LN Cells in Response to GA Stimulation (normalized to GAPDH)

| Group ID | Drug Stimulation | GA Conc. (µg/mL) | IL-5 mRNA Fold Change | Range |
|---|---|---|---|---|
| 3 | Mylan GA (M2) | 0.3 | 0.8 | 0.6-1.2 |
| | | 1 | 1.9 | 1.1-3.3 |
| | | 2.5 | 9.1 | 6.6-12.5 |
| | | 5 | 8.3 | 4.8-14.6 |
| | | 10 | 14.9 | 9.3-23.7 |
| | | 20 | 14.9 | 9.3-23.9 |
| | Copaxone (C2) | 0.3 | 1.2 | 0.5-2.6 |
| | | 1 | 4.0 | 2.2-7.3 |
| | | 2.5 | 18.9 | 11.2-31.7 |
| | | 5 | 15.5 | 9.6-25.1 |
| | | 10 | 34.4 | 28-42.1 |
| | | 20 | 29.5 | 23.6-36.9 |
| | MBP | 10 | 0.6 | 0.5-0.7 |
| | ConA | 2.5 | 21.1 | 13.7-32.5 |
| 4 | Mylan GA (M2) | 0.3 | 2.0 | 1.4-2.9 |
| | | 1 | 1.9 | 0.8-4.8 |
| | | 2.5 | 11.1 | 8.8-14 |
| | | 5 | 13.3 | 6.2-28.4 |
| | | 10 | 32.3 | 18.8-55.6 |
| | | 20 | 18.7 | 8.9-39.5 |
| | Copaxone (C2) | 0.3 | 1.3 | 0.7-2.4 |
| | | 1 | 3.1 | 2-4.9 |
| | | 2.5 | 4.7 | 2.4-9 |
| | | 5 | 10.4 | 5.6-19.3 |
| | | 10 | 9.8 | 5.2-18.8 |
| | | 20 | 15.8 | 9.3-26.7 |
| | MBP | 10 | 2.3 | 2-2.6 |
| | ConA | 2.5 | 59.4 | 48.1-73.3 |

TABLE 35

Expression of Mouse IL-13 from Primary LN Cells in Response to GA Stimulation (normalized to Actβ)

| Group ID | Drug Stimulation | GA Conc. (µg/mL) | IL-13 mRNA Fold Change | Range |
|---|---|---|---|---|
| 3 | Mylan GA (M2) | 0.3 | 0.9 | 0.6-1.3 |
| | | 1 | 4.4 | 2.9-6.7 |
| | | 2.5 | 7.2 | 4.7-11 |
| | | 5 | 11.5 | 7.7-17.2 |
| | | 10 | 15.6 | 11.4-21.2 |
| | | 20 | 14.4 | 8.2-25.5 |
| | Copaxone (C2) | 0.3 | 2.2 | 1.5-3.3 |
| | | 1 | 3.1 | 1.8-5.4 |
| | | 2.5 | 10.6 | 5-22.2 |
| | | 5 | 17.5 | 10-30.7 |
| | | 10 | 22.7 | 16.7-30.9 |
| | | 20 | 17.2 | 13.7-21.5 |
| | MBP | 10 | 0.7 | 0.4-1.2 |
| | ConA | 2.5 | 15.6 | 9.7-25.1 |
| 4 | Mylan GA (M2) | 0.3 | 1.4 | 0.9-2.1 |
| | | 1 | 3.1 | 1.5-6.1 |
| | | 2.5 | 7.5 | 4.3-13.3 |
| | | 5 | 8.6 | 6.7-11.2 |
| | | 10 | 13.6 | 9-20.5 |
| | | 20 | 10.2 | 4.5-23.2 |
| | Copaxone (C2) | 0.3 | 0.8 | 0.4-1.8 |
| | | 1 | 3.4 | 2.6-4.4 |
| | | 2.5 | 4.4 | 2.7-7.3 |
| | | 5 | 13.5 | 10.9-16.8 |
| | | 10 | 11.7 | 9.9-13.8 |
| | | 20 | 9.6 | 4.7-19.7 |
| | MBP | 10 | 1.0 | 0.4-2.1 |
| | ConA | 2.5 | 20.4 | 10.6-39.3 |

TABLE 36

Expression of Mouse IL-13 from Primary LN Cells in Response to GA Stimulation (normalized to GAPDH)

| Group ID | Drug Stimulation | GA Conc. (µg/mL) | IL-13 mRNA Fold Change | Range |
|---|---|---|---|---|
| 3 | Mylan GA (M2) | 0.3 | 0.9 | 0.7-1.1 |
| | | 1 | 3.6 | 2.4-5.4 |
| | | 2.5 | 13.7 | 8.5-21.9 |
| | | 5 | 20.9 | 13-33.5 |
| | | 10 | 26.0 | 16.4-41.1 |
| | | 20 | 23.4 | 14.1-38.8 |
| | Copaxone (C2) | 0.3 | 1.4 | 1.2-1.7 |
| | | 1 | 6.6 | 4-11 |
| | | 2.5 | 26.3 | 12.4-55.9 |
| | | 5 | 56.2 | 31.3-100.9 |
| | | 10 | 78.6 | 59.6-103.5 |
| | | 20 | 57.0 | 43.9-74 |
| | MBP | 10 | 0.5 | 0.3-0.8 |
| | ConA | 2.5 | 27.4 | 16.9-44.5 |
| 4 | Mylan GA (M2) | 0.3 | 1.9 | 1-3.9 |
| | | 1 | 4.6 | 2.7-8 |
| | | 2.5 | 10.2 | 5.4-19 |
| | | 5 | 26.5 | 20.5-34.3 |
| | | 10 | 48.4 | 26.2-89.2 |
| | | 20 | 39.6 | 24.1-65.3 |
| | Copaxone (C2) | 0.3 | 1.0 | 0.4-2.4 |
| | | 1 | 3.8 | 2.5-5.9 |
| | | 2.5 | 5.8 | 3.2-10.3 |
| | | 5 | 27.7 | 22.3-34.4 |
| | | 10 | 18.8 | 13-27.2 |
| | | 20 | 17.5 | 7.8-39.6 |
| | MBP | 10 | 1.2 | 0.9-1.7 |
| | ConA | 2.5 | 34.8 | 22.2-54.5 |

Conclusion

Use of β-actin as a housekeeping gene resulted in reproducible expression of a variety of cytokine mRNAs observed when a lot of Copaxone was compared to a lot of GMA using lymph node cells obtained from mice immunized with either Copaxone or GMA. In these experiments, stimulation of lymph node cells from mice obtained from either Copaxone or GMA-immunized animals with either Copaxone or GMA resulted in comparable levels of IL-2, IL-4, IL-5, and IL-13 mRNA.

Example VI. Evaluation of Reference Genes Using Mouse Spleen Cells Stimulated with Concanavalin a for Use in a Real-Time Polymerase Chain Reaction Method To evaluate reference genes for normalization of the real-time PCR data, the mRNA expression profiles of eight reference genes, β-Actin, Atp5b, B2m, Cyc1, Hprt, Gapdh, Ppia, and Rpl13a, were studied in CD-1 mouse spleen cells treated with different concentrations of Concanavalin A (ConA), a non-specific T-cell stimulant. The data were analyzed using the NormFinder program, and the reference genes were ranked according to their stability.

The eight reference genes tested are listed in Table 37, and the primer/probes used for amplification and detection are shown in Table 38.

TABLE 37

Reference Genes Tested

| Full Name | Abbreviation | Gene function |
|---|---|---|
| Beta Actin | Actβ or β-Actin | Cytoskeletal structural actin |

TABLE 37-continued

Reference Genes Tested

| Full Name | Abbreviation | Gene function |
| --- | --- | --- |
| ATP Synthase | Atp5b | Produce ATP from ADP |
| Beta-2 Microglobulin | B2m | Component of the major histocompatibility complex class I molecules |
| Cytochrome c-1 | Cyc1 | Transfer electrons to cytochrome c in mitochondrial respiratory chain |
| Hypoxanthine Guanine Phosphoribosyl Transferase | Hprt | Generation of purine nucleotides through the purine salvage pathway |
| Glyceraldehyde-3-Phosphate Dehydrogenase | Gapdh | Enzyme in glycolysis and nuclear functions |
| Peptidylprolyl Isomerase A (Cyclophilin A) | Ppia | Accelerate the folding of proteins |
| Ribosomal Protein L13A | Rpl13a | Structural component of the 60S ribosomal subunit |

TABLE 38

Primer/Probe Characteristics

| Gene | LifeTechnologies Cat # | ID | Amplicon Size (bp) |
| --- | --- | --- | --- |
| Actβ | 4331182 | Mm00607939_s1 | 115 |
| Atp5b | 4331182 | Mm00443967_g1 | 83 |
| B2m | 4331182 | Mm00437762_m1 | 77 |
| Cyc1 | 4331182 | Mm00470540_m1 | 56 |
| Hprt | 4331182 | Mm01545399_m1 | 81 |
| Gapdh | 4352339E | NA | 107 |
| Ppia | 4331182 | Mm03024003_g1 | 145 |
| Rpl13a | 4331182 | Mm01612986_gH | 122 |

A 1 mg/mL ConA stock solution (ConA-SS1) was prepared by reconstituting 5 mg of lyophilized powder with 5.0 mL of sterile 1×DPBS. The ConA-SS1 solution was further diluted to a 20 µg/mL (ConA-SS2) by adding 40 µL of ConA-SS1 (1 mg/mL) to 1.96 mL of DMEM-10 medium. ConA dilution samples with different concentrations were prepared. For 96-well tissue culture plate, 120 µL of each ConA sample was added in a well with 120 µL of spleen cells.

Splenocytes were obtained from four female CD-1 mice (8 weeks of age) and suspended in tissue culture medium DMEM-10. A Trypan blue exclusion method was used to determine the cell density of viable cells in the suspension. After cell counting, the spleen cell suspension was prepared in DMEM-10 medium at density of $7.5 \times 10^6$ cell/mL. ConA dilution samples (0.12 mL) were added in the assigned wells of a 96-well tissue culture plates. The same volume of prepared spleen cells (0.12 mL) were added to the assigned wells. The spleen cells with mock stimulation (DMEM-10 medium) were used to monitor the background mRNA level for each gene. Stimulations with ConA are summarized in Table 39. The plates were incubated at 37° C. in a humidified 5% $CO_2$ incubator for 6 hr.

TABLE 39

ConA Stimulation of Spleen Cells Isolated from CD-1 Mice

| # of mice | Stimulation | Concentration (µg/mL) |
| --- | --- | --- |
| 4 | ConA Solution | 0.01, 0.03, 0.1, 0.3, 1.0, 3.0 |
|  | DMEM-10 | 0 |

Total RNA was isolated from ConA treated spleen cells at 6 hours post-stimulation according to the study method XBL 12094 M01 [1]. Briefly, at the end of incubation time, treated spleen cells were washed with PBS and lysed with RNA lysis buffer. The lysate was transferred to a 96-well binding plate and total RNA was isolated using the SV 96 Total RNA Isolation System (Promega; Cat. No. Z3505). Samples were washed with RNA wash solution and treated with DNase solution. After DNase activity was stopped and samples were washed with RNA wash solution again, RNA samples were eluted with nuclease-free water to a 96-well plate by a vacuum manifold system. RNA samples were stored at ca −70° C.

cDNA was synthesized from total RNA as previously described for PHA 040-036 and PHA 040-037. Briefly, the High Capacity cDNA Reverse Transcription master mix was prepared and distributed to assigned wells in a 96-well plate. The RNA samples were transferred to each well. Reverse transcription was performed by a Thermal Cycler (2720, Applied Biosystems) according to the program in Table 40.

TABLE 40

Reverse Transcription Program

|  | Step 1 | Step 2 | Step 3 | Step 4 |
| --- | --- | --- | --- | --- |
| Temperature | 25° C. | 37° C. | 85° C. | 4° C. |
| Time | 10 min | 120 min | 5 min | ∞ |

After the reverse transcription reaction was completed, cDNA samples were either directly used for real-time PCR or stored at ca −20° C.

Real-time PCR was performed using specific primers/probe for each reference gene. Briefly, the PCR samples were prepared by mixing TaqMan Universal PCR Master Mix (Cat. #4304437), cDNA samples and primers/probe for specific reference genes. The sample plates were performed using a real-time PCR system (7500, Applied Biosystems). The program for real-time PCR is summarized in Table 41.

TABLE 41

RT-PCR Program

|  | UNG Incubation | AmpliTag Gold Activation | 40 Cycles | |
| --- | --- | --- | --- | --- |
| Temperature | 50° C. | 95° C. | 95° C. | 60° C. |
| Time | 2 min | 10 min | 15 sec | 1 min |

The NormFinder Excel macro processes data that are provided in a linear scale. Thus, $C_T$ values initially were converted to a linear scale. The lowest $C_T$ value of a sample was identified across all samples within a reference gene and was arbitrarily set to 1.0. Relative quantities (RQ) were calculated for all other samples using the following equation:

$$RQ = 1/(2^{(C_{t\_sample} - C_{t\_min})})$$

The data were processed in the NormFinder analysis following instructions from the Molecular Diagnostic Laboratory Website.

Results and Discussion

The expression levels of all eight reference genes were evaluated by real-time PCR and values were reported directly as cycle threshold ($C_T$). $C_T$ is defined as the number of cycles needed for fluorescence to reach a specific threshold level of detection and is inversely related to the amount of initial RNA template present in the sample.

Based on the expression levels in spleen cells responding to ConA stimulation, these reference genes can be divided into an abundant class (ActB with the mean $C_T$ value of 22.8), a moderately abundant class (Atp5b, B2m, GAPDH, Ppia and Rpl13a) and a low abundance class (Cyc1 and Hprt with the mean $C_T$ value of >29) (Table 42).

TABLE 42

$C_T$ Summary Table

| Gene Name | Mean ($C_T$) | Minimum ($C_T$) | Maximum ($C_T$) |
|---|---|---|---|
| ActB | 22.8 | 20.8 | 24.6 |
| Atp5b | 26.7 | 24.0 | 29.3 |
| B2m | 25.4 | 23.3 | 27.0 |
| Cyc1 | 29.1 | 26.6 | 31.9 |
| Hprt | 31.6 | 29.1 | 34.7 |
| Gapdh | 26.8 | 25.3 | 28.9 |
| Ppia | 26.4 | 23.4 | 30.3 |
| Rpl13a | 26.0 | 24.1 | 28.2 |

For each reference gene, $C_T$ values remained relatively constant from samples treated with low concentrations of ConA (0.03 to 0.1 cg/mL) compared to DMEM-10 control. $C_T$ values appeared to decrease as the ConA concentration increased (0.3 to 3 µg/mL). This pattern was observed for all reference genes in response to ConA stimulation. The decrease in $C_T$ values were slightly less for the GAPDH gene in samples treated with 1 and 3 µg/mL of ConA. The results suggested that expression of the reference genes might be upregulated in samples treated with ConA at a concentration >0.3 µg/mL.

Conclusion

Analyzing the data suggested that use of two housekeeping genes, GAPDH, which was used in all previous experiments, and β-actin, which seemed quite stable, are a reasonable option for normalizing data.

Example VII. Use of a Real-Time Polymerase Chain Reaction Method for the Quantitative Measurement of mRNA Levels of Cytokines in Mouse Lymph Node Cells after Glatiramer Acetate Stimulation in Three Identical Experiments A real-time polymerase chain reaction method was used to measure the expression of IL-2, IL-4, IL-5, and IL-13 mRNA in GA-stimulated LN cells from GA-immunized mice. Three identical experiments were carried out. In each experiment, mice were immunized with GA, and LN cells from each group of mice were stimulated with each of six concentrations of the same batch of GA used for immunization. GAPDH and β-actin were used as reference genes.

The Experimental Design is shown in Table 43. Each of the three groups consisted of four female CSJLF1/JRj (Janvier Labs) mice, approximately 8-12 weeks of age. On Day 0, mice were immunized by injection of 0.1 mL injection volume into four footpads (about 10 µL into each of the front footpad, 40 µL into each of the hind footpad). The immunization contained a total dose of 250 µg of one lot of GA (Copaxone batch P53974)+CFA (0.5 mg/mL). On Day 10 post-immunization, lymph cells were isolated from animals and stimulated with enriched DCCM-1 (mock-stimulated vehicle control), 2.5 µg/mL Concanavalin A (ConA, a positive control) or GA.

Ten days following immunization, LN cell samples isolated from the immunized mice each were stimulated with 0.3, 1, 2.5, 5, 10, or 20 µg/mL of Copaxone batch P53974 as shown in Table 43.

TABLE 43

Experimental Design Summary

| Group | LN Cells (Animal stimulated with) | Stimulation | Concentration (µg/mL) |
|---|---|---|---|
| 1 | Copaxone ® GA + CFA | Copaxone ® GA Solution | 0.3, 1, 2.5, 5, 10, 20 |
| 2 | Copaxone ® GA + CFA | ConA | 2.5 |
|  |  | Enriched DCCM-1 | 0 |
|  |  | Copaxone ® GA Solution | 0.3, 1, 2.5, 5, 10, 20 |
| 3 | Copaxone ® GA + CFA | ConA | 2.5 |
|  |  | Enriched DCCM-1 | 0 |
|  |  | Copaxone ® GA Solution | 0.3, 1, 2.5, 5, 10, 20 |
|  |  | ConA | 2.5 |
|  |  | Enriched DCCM-1 | 0 |

Total RNA was isolated from stimulated LN cells after 6 hours of incubation at about 37° C. in a humidified $CO_2$ incubator, using the SV 96 Total RNA Isolation System according to the manufacturer's protocol (Promega, Cat. #Z3500). cDNA was synthesized from each RNA sample in triplicate using High Capacity cDNA Reverse Transcription Kit (Life Technologies, formerly Applied Biosystems) according to the manufacturer's protocol. Reverse Transcription was performed with a Thermal Cycler (2720, Life Technologies) using the following program:

|  | Step 1 | Step 2 | Step 3 | Step 4 |
|---|---|---|---|---|
| Temperature (° C.) | 25 | 37 | 85 | 4 |
| Time (min) | 10 | 120 | 5 | ∞ |

Mouse primers/probes for cytokines and housekeeping genes are listed in Table 44 below (Life Technologies).

TABLE 44

Mouse Primers/Probes

| Primers | Testing Gene | Life Technologies ID |
|---|---|---|
| Actin, Beta (Actβ) | Reference Gene | Mm00607939_s1 |
| GAPDH | Reference Gene | Mm99999915_g1 |
| Cytokine IL-2 | Target Gene | Mm00434256_m1 |
| Cytokine IL-4 | Target Gene | Mm00445259_m1 |
| Cytokine IL-5 | Target Gene | Mm00439646_m1 |
| Cytokine IL-13 | Target Gene | Mm00434204_m1 |

Samples were prepared using TaqMan Universal PCR Master Mix II (Life Technologies) and run in 96-well plates using a Real-Time PCR system (7500, Life Technologies) using the following program for Real-Time PCR:

|  | UNG Incubation | AmpliTag Gold Activation | PCR for 40 Cycles | |
|---|---|---|---|---|
| Temp (° C.) | 50 | 95 | 95 | 60 |
| Time | 2 min | 10 min | 15 sec | 1 min |

The levels of cytokine mRNA were calculated using a standard $\Delta\Delta C_T$ method as described previously. The expression levels of mouse IL-2, IL-4, IL-5 and IL-13 mRNA observed are summarized below in Tables 45 to 48. The fold increases in cytokine mRNA levels following normalization by GAPDH and β-actin gene expression were comparable.

TABLE 45

Expression of mIL-2 from LN Cells in Response to GA Stimulation

| Group | Stimulation | Conc. (µg/mL) | IL-2 mRNA/GAPDH Fold Change | IL-2 mRNA/GAPDH Induction Range | IL-2 mRNA/Actβ Fold Change | IL-2 mRNA/Actβ Induction Range |
|---|---|---|---|---|---|---|
| Group 1 | GA-0.3 | 0.3 | 4.9 | 3.5-6.7 | 4.5 | 3.4-5.8 |
| | GA-1 | 1.0 | 11.1 | 8.1-15.1 | 11.9 | 9.8-14.4 |
| | GA-2.5 | 2.5 | 19.1 | 16.1-22.7 | 18.2 | 15.7-21.2 |
| | GA-5 | 5.0 | 26.1 | 17.7-38.5 | 26.5 | 19.1-36.9 |
| | GA-10 | 10 | 34.2 | 23.1-50.5 | 34.5 | 24.8-47.8 |
| | GA-20 | 20 | 46.4 | 40.3-53.5 | 44.6 | 39-50.9 |
| | DCCM1 | NA | 1.0 | 0.6-1.5 | 1.0 | 0.6-1.6 |
| | ConA | 2.5 | 102.9 | 78.4-135.2 | 157.7 | 119.1-208.7 |
| Group 2 | GA-0.3 | 0.3 | 7.3 | 6.6-8 | 6.2 | 5.7-6.7 |
| | GA-1 | 1.0 | 16.1 | 15.2-17.1 | 14.0 | 13.3-14.9 |
| | GA-2.5 | 2.5 | 26.6 | 19.3-36.5 | 22.4 | 16-31.2 |
| | GA-5 | 5.0 | 35.2 | 30.2-41 | 30.1 | 27.2-33.4 |
| | GA-10 | 10 | 49.7 | 42.7-57.9 | 42.2 | 35.6-49.9 |
| | GA-20 | 20 | 57.5 | 48.1-68.7 | 51.1 | 42.8-61 |
| | DCCM1 | NA | 1.0 | 0.8-1.3 | 1.0 | 0.8-1.2 |
| | ConA | 2.5 | 122.2 | 116.9-127.8 | 137.4 | 131.5-143.5 |
| Group 3 | GA-0.3 | 0.3 | 2.8 | 2.4-3.4 | 2.8 | 2.4-3.2 |
| | GA-1 | 1.0 | 6.9 | 6.1-7.7 | 6.3 | 5.7-7 |
| | GA-2.5 | 2.5 | 12.5 | 9.2-16.9 | 11.6 | 8.8-15.2 |
| | GA-5 | 5.0 | 16.0 | 13.1-19.4 | 14.9 | 13.6-16.4 |
| | GA-10 | 10 | 21.4 | 14.4-31.6 | 19.7 | 12.8-30.3 |
| | GA-20 | 20 | 27.4 | 20.1-37.4 | 24.4 | 17.7-33.8 |
| | DCCM1 | NA | 1.0 | 0.8-1.2 | 1.0 | 0.8-1.2 |
| | ConA | 2.5 | 55.8 | 47.1-66.2 | 91.7 | 76.8-109.5 |

TABLE 46

Expression of mIL-4 from LN Cells in Response to GA Stimulation

| Group | Stimulation | Conc. (µg/mL) | IL-4 mRNA/GAPDH Fold Change | IL-4 mRNA/GAPDH Induction Range | IL-4 mRNA/Actβ Fold Change | IL-4 mRNA/Actβ Induction Range |
|---|---|---|---|---|---|---|
| Group 1 | GA-0.3 | 0.3 | 6.8 | 5.1-9.1 | 6.2 | 5-7.7 |
| | GA-1 | 1.0 | 15.1 | 11.4-19.9 | 16.1 | 14-18.5 |
| | GA-2.5 | 2.5 | 20.9 | 14.2-30.8 | 19.9 | 13.7-29.1 |
| | GA-5 | 5.0 | 22.0 | 14.9-32.5 | 22.4 | 16-31.2 |
| | GA-10 | 10 | 31.3 | 18.1-54.1 | 31.5 | 19-52.2 |
| | GA-20 | 20 | 32.6 | 28.1-37.8 | 31.3 | 27.2-36 |
| | DCCM1 | NA | 1.0 | 0.7-1.5 | 1.0 | 0.7-1.5 |
| | ConA | 2.5 | 35.6 | 27.4-46.2 | 54.5 | 41.6-71.4 |
| Group 2 | GA-0.3 | 0.3 | 6.9 | 5.6-8.5 | 5.9 | 4.8-7.2 |
| | GA-1 | 1.0 | 13.0 | 9.9-17 | 11.3 | 8.7-14.8 |
| | GA-2.5 | 2.5 | 22.6 | 16.5-30.9 | 19.0 | 13.7-26.4 |
| | GA-5 | 5.0 | 27.5 | 23.4-32.2 | 23.5 | 21.1-26.3 |
| | GA-10 | 10 | 29.7 | 25.9-34.1 | 25.2 | 21.5-29.5 |
| | GA-20 | 20 | 29.1 | 23.9-35.4 | 25.9 | 21.3-31.5 |
| | DCCM1 | NA | 1.0 | 0.7-1.4 | 1.0 | 0.8-1.3 |
| | ConA | 2.5 | 34.2 | 29.8-39.3 | 38.5 | 33.5-44.2 |
| Group 3 | GA-0.3 | 0.3 | 6.7 | 5.8-7.7 | 6.5 | 5.9-7.2 |
| | GA-1 | 1.0 | 13.6 | 12-15.4 | 12.5 | 11.2-14 |
| | GA-2.5 | 2.5 | 22.5 | 15.5-32.6 | 20.9 | 14.8-29.5 |
| | GA-5 | 5.0 | 26.5 | 20.4-34.3 | 24.8 | 20.4-30.1 |
| | GA-10 | 10 | 34.1 | 25.7-45.2 | 31.4 | 22.5-43.9 |
| | GA-20 | 20 | 36.4 | 25.2-52.5 | 32.5 | 22 2-47 4 |
| | DCCM1 | NA | 1.0 | 0.6-1.7 | 1.0 | 0.6-1.7 |
| | ConA | 2.5 | 21.8 | 18.9-25.1 | 35.7 | 30.7-41.6 |

TABLE 47

Expression of mIL-5 from LN Cells in Response to GA Stimulation

| Group | Stimulation | Conc. (µg/mL) | IL-5 mRNA/GAPDH Fold Change | IL-5 mRNA/GAPDH Induction Range | IL-5 mRNA/Actβ Fold Change | IL-5 mRNA/Actβ Induction Range |
|---|---|---|---|---|---|---|
| Group 1 | GA-0.3 | 0.3 | 2.9 | 2.6-3.3 | 2.8 | 2.4-3.3 |
| | GA-1 | 1.0 | 6.8 | 4.4-10.6 | 7.1 | 4.8-10.7 |
| | GA-2.5 | 2.5 | 9.8 | 6.6-14.4 | 10.0 | 7.6-13.3 |
| | GA-5 | 5.0 | 9.9 | 6.1-16.1 | 9.5 | 6.1-14.5 |
| | GA-10 | 10 | 8.5 | 5.1-14.4 | 9.0 | 5.7-14.4 |
| | GA-20 | 20 | 13.8 | 11-17.2 | 12.1 | 9.3-15.7 |
| | DCCM1 | NA | 1.0 | 0.7-1.4 | 1.0 | 0.7-1.4 |
| | ConA | 2.5 | 12.0 | 9-15.9 | 16.6 | 13.4-20.5 |
| Group 2 | GA-0.3 | 0.3 | 5.3 | 4.5-6.3 | 5.1 | 4.4-6 |
| | GA-1 | 1.0 | 8.1 | 5.7-11.6 | 8.2 | 5.8-11.7 |
| | GA-2.5 | 2.5 | 15.4 | 9.3-25.8 | 14.1 | 8.8-22.6 |
| | GA-5 | 5.0 | 18.9 | 15.7-22.7 | 17.5 | 14.3-21.4 |
| | GA-10 | 10 | 21.1 | 16.1-27.7 | 19.4 | 14.5-26 |
| | GA-20 | 20 | 18.9 | 15.6-22.9 | 17.2 | 14.7-20.2 |
| | DCCM1 | NA | 1.0 | 0.9-1.1 | 1.0 | 0.9-1.1 |
| | ConA | 2.5 | 21.4 | 18.5-24.6 | 25.4 | 21.6-29.9 |
| Group 3 | GA-0.3 | 0.3 | 2.7 | 2.2-3.4 | 2.6 | 2.1-3.1 |
| | GA-1 | 1.0 | 6.7 | 5.6-8.1 | 5.8 | 5-6.9 |
| | GA-2.5 | 2.5 | 10.4 | 7.1-15.3 | 9.7 | 6.7-14 |
| | GA-5 | 5.0 | 10.2 | 6.6-15.7 | 8.9 | 5.9-13.3 |
| | GA-10 | 10 | 12.9 | 8.7-19.1 | 11.3 | 7.6-16.8 |
| | GA-20 | 20 | 14.3 | 10.7-19.1 | 11.3 | 8.7-14.7 |
| | DCCM1 | NA | 1.0 | 0.7-1.4 | 1.0 | 0.7-1.4 |
| | ConA | 2.5 | 8.6 | 7.2-10.2 | 12.4 | 9.8-15.7 |

TABLE 48

Expression of mIL-13 from LN Cells in Response to GA Stimulation

| Group | Stimulation | Conc. (μg/mL) | IL-13 mRNA/GAPDH Fold Change | IL-13 mRNA/GAPDH Induction Range | IL-13 mRNA/Actβ Fold Change | IL-13 mRNA/Actβ Induction Range |
|---|---|---|---|---|---|---|
| Group 1 | GA-0.3 | 0.3 | 4.9 | 3.8-6.2 | 4.7 | 3.6-6.1 |
| | GA-1 | 1.0 | 13.9 | 10.2-19 | 14.6 | 11.3-18.8 |
| | GA-2.5 | 2.5 | 21.3 | 13.6-33.5 | 21.9 | 15.2-31.5 |
| | GA-5 | 5.0 | 24.0 | 16.5-35 | 23.0 | 17-31 |
| | GA-10 | 10 | 26.0 | 16.9-40 | 27.5 | 19.1-39.5 |
| | GA-20 | 20 | 29.7 | 27.7-32 | 26.2 | 22.6-30.3 |
| | DCCM1 | NA | 1.0 | 0.7-1.5 | 1.0 | 0.7-1.5 |
| | ConA | 2.5 | 24.1 | 18.6-31.3 | 33.3 | 27.8-39.9 |
| Group 2 | GA-0.3 | 0.3 | 5.7 | 4.6-7 | 5.4 | 4.5-6.7 |
| | GA-1 | 1.0 | 11.9 | 9.5-15.1 | 12.1 | 9.7-15.2 |
| | GA-2.5 | 2.5 | 19.4 | 12.3-30.6 | 17.7 | 11.8-26.7 |
| | GA-5 | 5.0 | 21.7 | 20.6-23 | 20.1 | 18.3-22.1 |
| | GA-10 | 10 | 27.7 | 20.9-36.6 | 25.5 | 18.9-34.4 |
| | GA-20 | 20 | 23.3 | 17.7-30.8 | 21.3 | 16.5-27.5 |
| | DCCM1 | NA | 1.0 | 0.7-1.4 | 1.0 | 0.7-1.4 |
| | ConA | 2.5 | 23.8 | 20.4-27.8 | 28.4 | 23.9-33.8 |
| Group 3 | GA-0.3 | 0.3 | 6.1 | 5.4-6.9 | 5.8 | 5.4-6.3 |
| | GA-1 | 1.0 | 12.3 | 9-16.6 | 10.7 | 7.9-14.4 |
| | GA-2.5 | 2.5 | 20.5 | 14.4-29.2 | 19.1 | 13.6-26.7 |
| | GA-5 | 5.0 | 21.3 | 14-32.4 | 18.5 | 12.5-27.5 |
| | GA-10 | 10 | 24.8 | 16.1-38.3 | 21.8 | 14.1-33.7 |
| | GA-20 | 20 | 24.6 | 18.8-32.4 | 19.5 | 15.2-24.9 |
| | DCCM1 | NA | 1.0 | 0.7-1.3 | 1.0 | 0.8-1.3 |
| | ConA | 2.5 | 17.8 | 15.2-20.8 | 25.7 | 20.6-32.1 |

TABLE 49

Comparison of Cytokine mRNA Induction at 20 μg/mL GA Stimulation

| | Induction Fold of Cytokine mRNA by Copaxone ® (Normalized with GAPDH) | | | | Induction Fold of Cytokine mRNA by Copaxone ® (Normalized with Actβ) | | | |
|---|---|---|---|---|---|---|---|---|
| Cytokines | IL-2 | IL-4 | IL-5 | IL-13 | IL-2 | IL-4 | IL-5 | IL-13 |
| Group 1 | 46.4 | 32.6 | 13.8 | 29.7 | 44.6 | 31.3 | 12.1 | 26.2 |
| Group 2 | 57.5 | 29.1 | 18.9 | 23.3 | 51.1 | 25.9 | 17.2 | 21.3 |
| Group 3 | 27.4 | 36.4 | 14.3 | 24.6 | 24.4 | 32.5 | 11.3 | 19.5 |
| Mean | 43.8 | 32.7 | 15.7 | 25.9 | 40.0 | 29.9 | 13.5 | 22.3 |
| SD | 15.2 | 3.7 | 2.8 | 3.4 | 13.9 | 3.5 | 3.2 | 3.5 |
| CV(%) | 34.8 | 11.2 | 17.9 | 13.1 | 34.8 | 11.8 | 23.6 | 15.5 |

Levels of murine IL-2, IL-4, IL-5 and IL-13 expression in lymph node (LN) cells isolated from GA-immunized mice were measured in GA-immunized mouse LN cells stimulated with GA. The fold increases in cytokine mRNA levels following normalization by GAPDH and β-actin gene expression were comparable. Furthermore, the levels of mRNA expression of mouse cytokines IL-2, IL-4, IL-5 and IL-13 were increased in response to GA stimulation in LN cells isolated from mice immunized with GA, and these increases were dose-dependent.

Measurement of IL-2 mRNA showed the greatest variability whereas detection of IL-4, IL-5, and IL-13 mRNA in response to GA stimulation was more reproducible in these experiments. These results suggest that measurement of GA stimulated IL-4, IL-5, or IL-13 mRNA in LN cells from GA-immunized mice might provide a more reproducible and reliable assessment method than measurement of IL-2 mRNA.

Example VIII. Comparison of Cytokine mRNA Expression in Mouse LN Cells after Stimulation with Twelve Lots of GA Using a Real-Time Polymerase Chain Reaction Method A real-time polymerase chain reaction method was used to measure the expression of IL-2, IL-4, IL-5, and IL-13 mRNA in LN cells, from GA-immunized mice, following stimulation with one of twelve GA lots. One lot of GA (Copaxone P53974) was used for immunization. The GA lots used for stimulation included eight Copaxone lots (P53974, X06511, X06841, X06861, X06941, X06741, X06901, P63020), and four GMA lots (GMA/0.02/001/13, GMA/0.02/002/13, GMA/0.02/003/13, and GMA/R&D/026/11). The Experimental Design is shown in Table 50. Twenty female CSJLF1/JRj mice (Janvier Labs), approximately 8-12 weeks of age, were immunized by injection of 0.1 mL injection volume into four footpads (about 10 μL into each of the front footpad, 40 μL into each of the hind footpad) on Day 0. The immunization contained a total dose of 250 μg of one lot of GA (Copaxone batch P53974)+CFA (0.5 mg/mL). On Day 10 post-immunization, lymph cells were isolated from animals and stimulated with enriched DCCM-1 (mock-stimulated vehicle control), 2.5 μg/mL Concanavalin A (ConA, a positive control) or 0.3, 1, 2.5, 5, 10, or 20 μg/mL of Copaxone batch P53974 as shown in Table 50.

TABLE 50

Experimental Design Summary

| Group | LN Cells (Animal Stimulated with) | Plate for Stimulation | Lot ID | Stimulation | Concentration (μg/mL) | Cytokine for Real-Time PCR |
|---|---|---|---|---|---|---|
| 1 | Copaxone ® GA Lot P53974 + | Plate 1 | C1 | Copaxone ® GA Lot P53974 Solution | 0.3, 1, 2.5, 5, 10, 20 | IL-2, IL-4, IL-5, |
| | | | C2 | Copaxone ® GA Lot | 0.3, 1, 2.5, 5, | IL-13 |

TABLE 50-continued

Experimental Design Summary

| Group | LN Cells (Animal Stimulated with) | Plate for Stimulation | Lot ID | Stimulation | Concentration (μg/mL) | Cytokine for Real-Time PCR |
|---|---|---|---|---|---|---|
| | CFA | | | X06511 Solution | 10, 20 | |
| | | | C3 | Copaxone ® GA Lot X06841 Solution | 0.3, 1, 2.5, 5, 10, 20 | IL-2, IL-4, IL-5, |
| | | | M1 | XBL 3024:3518 (API Lot#: GMA/0.02/001/13) | 0.3, 1, 2.5, 5, 10, 20 | IL-13, IL-17, CD25 |
| | | | | ConA | 2.5 | |
| | | | | Enriched DCCM-1 | 0 | |
| | | Plate 2 | C4 | Copaxone ® GA Lot X06861 Solution | 0.3, 1, 2.5, 5, 10, 20 | IL-2, IL-4, IL-5, |
| | | | C5 | Copaxone ® GA Lot X06941 Solution | 0.3, 1, 2.5, 5, 10, 20 | IL-13 |
| | | | C6 | Copaxone ® GA Lot X06741 Solution | 0.3, 1, 2.5, 5, 10, 20 | IL-2, IL-4, IL-5, |
| | | | M2 | XBL 3024:3519 (API Lot#: GMA/0.02/002/13) | 0.3, 1, 2.5, 5, 10, 20 | IL-13, IL-17, CD25 |
| | | | | ConA | 2.5 | |
| | | | | Enriched DCCM-1 | 0 | |
| | | Plate 3 | C7 | Copaxone ® GA Lot X06901 Solution | 0.3, 1, 2.5, 5, 10, 20 | IL-2, IL-4, IL-5, |
| | | | C8 | Copaxone ® GA Lot P63020 Solution | 0.3, 1, 2.5, 5, 10, 20 | IL-13, IL-17, |
| | | | M3 | XBL 3024:3520 (API Lot#: GMA/0.02/003/13) | 0.3, 1, 2.5, 5, 10, 20 | CD25 |
| | | | M4 | GA Lot R&D XBL3024.02 3087A-6 (API Lot#: GMA/R&D/026/11) | 0.3, 1, 2.5, 5, 10, 20 | |
| | | | | ConA | 2.5 | |
| | | | | Enriched DCCM-1 | 0 | |

Total RNA was isolated from stimulated LN cells using the SV 96 Total RNA Isolation System according to the manufacturer's protocol (Promega, Cat. #Z3500). cDNA was synthesized from each RNA sample in triplicate using High Capacity cDNA Reverse Transcription Kit (Life Technologies, formerly Applied Biosystems) according to the manufacturer's protocol. Reverse Transcription was performed by a Thermal Cycler (2720, Life Technologies) using the following program:

| | Step 1 | Step 2 | Step 3 | Step 4 |
|---|---|---|---|---|
| Temperature (° C.) | 25 | 37 | 85 | 4 |
| Time (min) | 10 | 120 | 5 | ∞ |

Mouse primers/probes for cytokines and housekeeping genes used were from Life Technologies: β-Actin (reference gene, Cat. # Mm00607939_s1), GAPDH (reference gene, Cat. # Mm99999915_g1), IL-2 (target gene, Cat. # Mm00434256_m1), IL-4 (target gene, Cat. # Mm00445259_m1), IL-5 (target gene, Mm00439646_m1), IL-13 (target gene, Mm00434204_m1), IL-17, and CD25).

Samples were prepared using TaqMan Universal PCR Master Mix II (Life Technologies) and run in 96-well plates using a Real-Time PCR system (7500, Life Technologies) using the following RT-PCR program:

| | UNG Incubation | AmpliTaq Gold Activation | PCR for 40 Cycles | |
|---|---|---|---|---|
| Temp (° C.) | 50 | 95 | 95 | 60 |
| Time | 2 min | 10 min | 15 sec | 1 min |

The levels of cytokine mRNA were calculated using a standard $\Delta\Delta C_T$ method as described previously. The expression levels of mouse IL-2, IL-4, IL-5, IL-13, IL-17, and CD25 mRNA observed are summarized below in Tables 51 to 71.

Variations among expression levels of IL-2, IL-4, IL-5 and IL-13 in the samples stimulated with Copaxone lots C1 to C8 were observed. The variations observed among Mylan lots M1, M2 and M3 were not greater than the variations observed among the Copaxone. However, LN cells stimulated with GMA lot M4 (altered lot GMA/R&D/026/11, made by withholding tyrosine for the first five minutes of synthesis) demonstrated significantly lower levels of cytokine expression, and different induction patterns (Tables 57, 61, 65, 67 and 69).

IL-17 showed concentration-dependent induction in LN cells stimulated with four lots of Copaxone and four lots of Mylan GA (Tables 68 and 69). Stimulation of CD25 (IL-2ra) mRNA was observed in samples taken 6 hours post-stimulation but the magnitude was less and no dose response was evident. (Tables 70 and 71). The expression levels of cytokine mRNAs normalized by β-actin showed less variability than those normalized by GAPDH.

TABLE 51

Expression of Mouse IL-2 from Primary LN Cells in Response to GA Stimulation (Plate 1: C1-C3)

| GA | Stimulation | Conc. (µg/mL) | IL-2 mRNA/GAPDH Fold Change | IL-2 mRNA/GAPDH Induction Range | IL-2 mRNA/B-Actin Fold Change | IL-2 mRNA/B-Actin Induction Range |
|---|---|---|---|---|---|---|
| C1 | GA-0.3 | 0.3 | 4.4 | 3.7-5.3 | 3.8 | 3.1-4.8 |
|    | GA-1 | 1.0 | 11.5 | 10-13.2 | 9.6 | 8.2-11.4 |
|    | GA-2.5 | 2.5 | 18.7 | 13.9-25.2 | 14.6 | 11.2-19 |
|    | GA-5 | 5.0 | 29.6 | 26.4-33.1 | 23.7 | 21.8-25.7 |
|    | GA-10 | 10 | 33.1 | 25.5-42.9 | 27.6 | 23.4-32.5 |
|    | GA-20 | 20 | 44.8 | 37.8-53.1 | 34.6 | 29.2-41 |
|    | DCCM1 | NA | 1.0 | 0.8-1.3 | 1.0 | 0.7-1.3 |
|    | ConA | 2.5 | 116.9 | 104.3-130.9 | 118.1 | 108.6-128.4 |
| C2 | GA-0.3 | 0.3 | 3.8 | 2.7-5.5 | 3.4 | 2.3-5 |
|    | GA-1 | 1.0 | 9.6 | 6.8-13.5 | 8.8 | 6.3-12.4 |
|    | GA-2.5 | 2.5 | 16.4 | 12.1-22.3 | 14.1 | 10.2-19.6 |
|    | GA-5 | 5.0 | 24.7 | 18.2-33.6 | 20.1 | 14.9-27.1 |
|    | GA-10 | 10 | 31.6 | 25.5-39.2 | 27.6 | 22-34.7 |
|    | GA-20 | 20 | 40.6 | 38.7-42.5 | 33.9 | 32.3-35.5 |
|    | DCCM1 | NA | 1.0 | 0.8-1.2 | 1.0 | 0.8-1.3 |
|    | ConA | 2.5 | 103.7 | 95.7-112.3 | 111.2 | 104.7-118 |
| C3 | GA-0.3 | 0.3 | 3.4 | 2.5-4.7 | 3.3 | 2.4-4.6 |
|    | GA-1 | 1.0 | 11.4 | 9.2-14.1 | 10.4 | 9-11.9 |
|    | GA-2.5 | 2.5 | 13.0 | 9.8-17.3 | 14.6 | 10.5-20.2 |
|    | GA-5 | 5.0 | 19.8 | 18.2-21.5 | 19.0 | 17-21.3 |
|    | GA-10 | 10 | 30.5 | 20.7-45 | 27.7 | 17.8-43.2 |
|    | GA-20 | 20 | 31.1 | 22.9-42.2 | 26.9 | 22.7-31.9 |
|    | DCCM1 | NA | 1.0 | 0.7-1.3 | 1.0 | 0.8-1.3 |
|    | ConA | 2.5 | 87.6 | 69.7-110.1 | 105.2 | 83.9-131.8 |

TABLE 52

Expression of Mouse IL-2 from Primary LN Cells in Response to GA Stimulation (Plate 2: C4-C6)

| GA | Stimulation | Conc. (µg/mL) | IL-2 mRNA/GAPDH Fold Change | IL-2 mRNA/GAPDH Induction Range | IL-2 mRNA/B-Actin Fold Change | IL-2 mRNA/B-Actin Induction Range |
|---|---|---|---|---|---|---|
| C4 | GA-0.3 | 0.3 | 3.3 | 2.3-4.8 | 3.4 | 2.8-4 |
|    | GA-1 | 1.0 | 9.3 | 7.2-12 | 9.5 | 8.2-11 |
|    | GA-2.5 | 2.5 | 24.0 | 17.1-33.6 | 18.7 | 13.4-26.2 |
|    | GA-5 | 5.0 | 33.8 | 29.6-38.6 | 23.2 | 20.3-26.6 |
|    | GA-10 | 10 | 35.1 | 28.3-43.4 | 26.9 | 21.7-33.5 |
|    | GA-20 | 20 | 31.2 | 15.4-63.3 | 32.6 | 16-66.4 |
|    | DCCM1 | NA | 1.0 | 0.7-1.3 | 1.0 | 0.8-1.3 |
|    | ConA | 2.5 | 100.3 | 85.2-118 | 106.7 | 93.6-121.6 |
| C5 | GA-0.3 | 0.3 | 4.6 | 3.5-6.2 | 3.8 | 2.9-4.8 |
|    | GA-1 | 1.0 | 12.1 | 9-16.4 | 9.5 | 7.1-12.7 |
|    | GA-2.5 | 2.5 | 23.6 | 20.4-27.5 | 16.6 | 14.5-19.1 |
|    | GA-5 | 5.0 | 31.5 | 23.6-42.2 | 22.3 | 16.9-29.4 |
|    | GA-10 | 10 | 18.9 | 12.8-28 | 23.8 | 12.8-44.3 |
|    | GA-20 | 20 | 37.5 | 24.8-56.6 | 32.5 | 23.2-45.7 |
|    | DCCM1 | NA | 1.0 | 0.8-1.3 | 1.0 | 0.8-1.3 |
|    | ConA | 2.5 | 92.7 | 78.1-110 | 96.2 | 80.6-114.9 |
| C6 | GA-0.3 | 0.3 | 5.3 | 4.9-5.8 | 4.3 | 3.8-4.9 |
|    | GA-1 | 1.0 | 12.0 | 10.3-13.9 | 9.3 | 8-10.8 |
|    | GA-2.5 | 2.5 | 20.3 | 11.5-36 | 16.1 | 9.9-26.4 |
|    | GA-5 | 5.0 | 24.5 | 21.5-27.9 | 19.3 | 16.4-22.8 |
|    | GA-10 | 10 | 36.2 | 31.5-41.5 | 27.7 | 22.8-33.6 |
|    | GA-20 | 20 | 37.3 | 28.1-49.4 | 31.7 | 25.8-38.9 |
|    | DCCM1 | NA | 1.0 | 0.8-1.3 | 1.0 | 0.8-1.2 |
|    | ConA | 2.5 | 99.8 | 85.7-116.3 | 103.1 | 86.1-123.5 |

TABLE 53

Expression of Mouse IL-2 from Primary LN Cells in Response to GA Stimulation (Plate 3: C7-C8)

| GA | Stimulation | Conc. (µg/mL) | IL-2 mRNA/GAPDH Fold Change | IL-2 mRNA/GAPDH Induction Range | IL-2 mRNA/B-Actin Fold Change | IL-2 mRNA/B-Actin Induction Range |
|---|---|---|---|---|---|---|
| C7 | GA-0.3 | 0.3 | 5.8 | 3.2-10.5 | 4.1 | 3.2-5.4 |
|    | GA-1 | 1.0 | 18.5 | 14.5-23.7 | 11.5 | 10.1-13.2 |
|    | GA-2.5 | 2.5 | 28.9 | 20.1-41.6 | 18.5 | 16.2-21 |
|    | GA-5 | 5.0 | 48.2 | 32.9-70.4 | 25.2 | 16.5-38.7 |
|    | GA-10 | 10 | 55.9 | 39.7-78.6 | 30.2 | 20.4-44.8 |
|    | GA-20 | 20 | 67.9 | 42.8-107.8 | 40.3 | 26.5-61.3 |
|    | DCCM1 | NA | 1.0 | 0.7-1.4 | 1.0 | 0.7-1.5 |
|    | ConA | 2.5 | 147.4 | 114.8-189.2 | 120.5 | 105.2-138.1 |
| C8 | GA-0.3 | 0.3 | 6.8 | 5.1-8.9 | 4.4 | 3.4-5.7 |
|    | GA-1 | 1.0 | 16.6 | 13.4-20.5 | 11.0 | 8.8-13.6 |
|    | GA-2.5 | 2.5 | 31.8 | 29.5-34.3 | 20.0 | 18.6-21.6 |
|    | GA-5 | 5.0 | 46.9 | 34.8-63.4 | 29.6 | 22.5-39 |
|    | GA-10 | 10 | 52.7 | 45.1-61.5 | 35.8 | 29.3-43.7 |
|    | GA-20 | 20 | 63.7 | 58.7-69.3 | 41.6 | 39.7-43.6 |
|    | DCCM1 | NA | 1.0 | 0.7-1.4 | 1.0 | 0.7-1.5 |
|    | ConA | 2.5 | 131.3 | 86.1-200.2 | 121.8 | 89.3-166.2 |

TABLE 54

Expression of Mouse IL-4 from Primary LN Cells in Response to GA Stimulation (Plate 1: C1-C3)

| GA | Stimulation | Conc. (µg/mL) | IL-4 mRNA/GAPDH Fold Change | IL-4 mRNA/GAPDH Induction Range | IL-4 mRNA/B-Actin Fold Change | IL-4 mRNA/B-Actin Induction Range |
|---|---|---|---|---|---|---|
| C1 | GA-0.3 | 0.3 | 4.2 | 3.2-5.7 | 3.7 | 2.7-5 |
|    | GA-1 | 1.0 | 10.7 | 9.2-12.3 | 8.9 | 7.5-10.6 |
|    | GA-2.5 | 2.5 | 14.5 | 10.7-19.6 | 11.3 | 8.6-14.7 |
|    | GA-5 | 5.0 | 20.8 | 15.8-27.4 | 16.7 | 12.8-21.7 |
|    | GA-10 | 10 | 21.4 | 16-28.5 | 17.8 | 14.5-21.9 |
|    | GA-20 | 20 | 27.1 | 21.9-33.6 | 21.0 | 17-25.9 |
|    | DCCM1 | NA | 1.0 | 0.8-1.3 | 1.0 | 0.8-1.3 |
|    | ConA | 2.5 | 26.8 | 23.7-30.4 | 27.1 | 24.6-29.9 |
| C2 | GA-0.3 | 0.3 | 7.2 | 4.3-12 | 6.4 | 3.7-10.9 |
|    | GA-1 | 1.0 | 12.1 | 8.1-17.9 | 11.1 | 7.5-16.5 |
|    | GA-2.5 | 2.5 | 17.9 | 12.1-26.5 | 15.4 | 10.2-23.1 |
|    | GA-5 | 5.0 | 34.4 | 23.5-50.4 | 27.9 | 19.2-40.7 |
|    | GA-10 | 10 | 35.2 | 28.4-43.8 | 30.7 | 24.4-38.7 |
|    | GA-20 | 20 | 44.3 | 37.8-51.8 | 37.0 | 31.6-43.3 |
|    | DCCM1 | NA | 1.0 | 0.6-1.6 | 1.0 | 0.6-1.6 |
|    | ConA | 2.5 | 41.1 | 36-46.9 | 44.1 | 39.1-49.7 |
| C3 | GA-0.3 | 0.3 | 4.4 | 3.5-5.5 | 4.3 | 3.3-5.5 |
|    | GA-1 | 1.0 | 11.2 | 8.7-14.6 | 10.2 | 8.3-12.6 |
|    | GA-2.5 | 2.5 | 11.6 | 7.7-17.3 | 12.9 | 8.4-20 |
|    | GA-5 | 5.0 | 19.6 | 17.4-22.1 | 18.8 | 16.3-21.7 |
|    | GA-10 | 10 | 26.0 | 19.3-34.9 | 23.6 | 16.3-34 |
|    | GA-20 | 20 | 21.7 | 16.3-28.8 | 18.7 | 16.4-21.4 |
|    | DCCM1 | NA | 1.0 | 0.7-1.4 | 1.0 | 0.7-1.4 |
|    | ConA | 2.5 | 25.8 | 22.3-30 | 31.0 | 26.8-35.8 |

TABLE 55

Expression of Mouse IL-4 from Primary LN Cells in Response to GA Stimulation (Plate 2: C4-C6)

| GA | Stimulation | Conc. (µg/mL) | IL-4 mRNA/GAPDH Fold Change | IL-4 mRNA/GAPDH Induction Range | IL-4 mRNA/B-Actin Fold Change | IL-4 mRNA/B-Actin Induction Range |
|---|---|---|---|---|---|---|
| C4 | GA-0.3 | 0.3 | 6.9 | 4.6-10.4 | 7.1 | 5.6-9 |
|    | GA-1 | 1.0 | 16.9 | 13-22 | 17.2 | 14.6-20.3 |

TABLE 55-continued

Expression of Mouse IL-4 from Primary LN Cells in Response to GA Stimulation (Plate 2: C4-C6)

| GA | Stimulation | Conc. (µg/mL) | IL-4 mRNA/GAPDH | | IL-4 mRNA/B-Actin | |
|---|---|---|---|---|---|---|
| | | | Fold Change | Induction Range | Fold Change | Induction Range |
| | GA-2.5 | 2.5 | 32.1 | 24.6-41.7 | 25.0 | 19.3-32.4 |
| | GA-5 | 5.0 | 50.1 | 42-59.8 | 34.4 | 28.7-41.1 |
| | GA-10 | 10 | 47.2 | 36.1-61.7 | 36.3 | 27.7-47.6 |
| | GA-20 | 20 | 39.4 | 19.5-79.4 | 41.2 | 20.3-83.3 |
| | DCCM1 | NA | 1.0 | 0.7-1.4 | 1.0 | 0.7-1.4 |
| | ConA | 2.5 | 42.5 | 38-47.6 | 45.3 | 42.7-48 |
| C5 | GA-0.3 | 0.3 | 5.4 | 4.1-7.2 | 4.4 | 3.4-5.6 |
| | GA-1 | 1.0 | 12.7 | 10.1-16 | 10.0 | 8-12.4 |
| | GA-2.5 | 2.5 | 17.1 | 15.1-19.4 | 12.1 | 10.8-13.5 |
| | GA-5 | 5.0 | 28.1 | 22-36.1 | 19.9 | 15.7-25.1 |
| | GA-10 | 10 | 19.4 | 15.6-24.1 | 24.4 | 14.4-41.4 |
| | GA-20 | 20 | 25.4 | 15.2-42.5 | 22.0 | 13.9-34.8 |
| | DCCM1 | NA | 1.0 | 0.9-1.2 | 1.0 | 1-1 |
| | ConA | 2.5 | 24.7 | NA* | 25.7 | NA* |
| C6 | GA-0.3 | 0.3 | 6.8 | 5.4-8.5 | 5.5 | 4.3-7 |
| | GA-1 | 1.0 | 14.7 | 12.1-17.9 | 11.5 | 9.4-13.9 |
| | GA-2.5 | 2.5 | 22.0 | 11.5-42.2 | 17.5 | 9.8-31.3 |
| | GA-5 | 5.0 | 26.9 | 24-30.2 | 21.2 | 18.3-24.7 |
| | GA-10 | 10 | 35.5 | 28.6-44.1 | 27.2 | 21-35.2 |
| | GA-20 | 20 | 27.3 | 20.2-36.9 | 23.2 | 18.4-29.2 |
| | DCCM1 | NA | 1.0 | 0.5-2 | 1.0 | 0.5-1.9 |
| | ConA | 2.5 | 31.9 | 27.8-36.6 | 32.9 | 27.9-39 |

TABLE 56

Expression of Mouse IL-4 from Primary LN Cells in Response to GA Stimulation (Plate 3: C7-C8)

| GA | Stimulation | Conc. (µg/mL) | IL-4 mRNA/GAPDH | | IL-4 mRNA/B-Actin | |
|---|---|---|---|---|---|---|
| | | | Fold Change | Induction Range | Fold Change | Induction Range |
| C7 | GA-0.3 | 0.3 | 9.3 | 5.2-16.7 | 6.7 | 5.3-8.5 |
| | GA-1 | 1.0 | 19.4 | 14.4-26.2 | 12.1 | 9.7-15 |
| | GA-2.5 | 2.5 | 32.8 | 21.2-50.8 | 20.9 | 15.9-27.6 |
| | GA-5 | 5.0 | 48.0 | 34.1-67.5 | 25.1 | 17-37.3 |
| | GA-10 | 10 | 45.3 | 30.5-67.4 | 24.5 | 15.8-38.1 |
| | GA-20 | 20 | 54.1 | 36-81.3 | 32.1 | 22.5-45.9 |
| | DCCM1 | NA | 1.0 | 0.7-1.5 | 1.0 | 0.6-1.6 |
| | ConA | 2.5 | 43.7 | 35.3-54.1 | 35.7 | 34.4-37.1 |
| C8 | GA-0.3 | 0.3 | 9.0 | 6.5-12.4 | 5.9 | 4.4-8 |
| | GA-1 | 1.0 | 17.5 | 14.4-21.3 | 11.6 | 9.5-14.1 |
| | GA-2.5 | 2.5 | 33.4 | 27.1-41.1 | 21.0 | 17.1-25.8 |
| | GA-5 | 5.0 | 36.5 | 27.8-48 | 23.1 | 18-29.5 |
| | GA-10 | 10 | 43.0 | 36.5-50.5 | 29.2 | 23.8-35.8 |
| | GA-20 | 20 | 42.4 | 38-47.4 | 27.7 | 25.4-30.2 |
| | DCCM1 | NA | 1.0 | 0.8-1.2 | 1.0 | 0.8-1.3 |
| | ConA | 2.5 | 37.2 | 25.7-53.7 | 34.5 | 27.4-43.5 |

TABLE 57

Expression of Mouse IL-4 from Primary LN Cells in Response to GA Stimulation (Plate 1-3: M1-M4)

| GA | Stimulation | Conc. (µg/mL) | IL-4 mRNA/GAPDH | | IL-4 mRNA/B-Actin | |
|---|---|---|---|---|---|---|
| | | | Fold Change | Induction Range | Fold Change | Induction Range |
| M1 Plate 1 | GA-0.3 | 0.3 | 6.2 | 4.8-7.9 | 5.3 | 4.1-6.9 |
| | GA-1 | 1.0 | 12.6 | 10.9-14.5 | 11.1 | 9.5-13 |
| | GA-2.5 | 2.5 | 21.3 | 13.3-34.1 | 16.6 | 10.6-25.9 |
| | GA-5 | 5.0 | 26.1 | 17.1-39.9 | 21.2 | 13.8-32.6 |
| | GA-10 | 10 | 37.0 | 19.2-71.7 | 29.0 | 15.5-54.3 |
| | GA-20 | 20 | 29.4 | 24.1-36 | 24.6 | 21.4-28.3 |
| | DCCM1 | NA | 1.0 | 0.6-1.6 | 1.0 | 0.6-1.6 |
| | ConA | 2.5 | 38.0 | 34.6-41.7 | 38.0 | 35.5-40.7 |
| M2 Plate 2 | GA-0.3 | 0.3 | 8.1 | 6.3-10.3 | 6.3 | 5.5-7.1 |
| | GA-1 | 1.0 | 17.2 | 15.1-19.5 | 12.7 | 11.4-14.3 |
| | GA-2.5 | 2.5 | 27.1 | 16.1-45.6 | 19.9 | 11.7-33.7 |
| | GA-5 | 5.0 | 33.6 | 22-51.4 | 26.2 | 18.1-37.8 |
| | GA-10 | 10 | 30.9 | 22.1-43 | 24.0 | 17.8-32.1 |
| | GA-20 | 20 | 38.8 | 27.1-55.5 | 30.9 | 21.2-45 |
| | DCCM1 | NA | 1.0 | 0.6-1.7 | 1.0 | 0.6-1.7 |
| | ConA | 2.5 | 37.0 | 32.4-42.3 | 38.6 | 32.4-46 |
| M3 Plate 3 | GA-0.3 | 0.3 | 5.5 | 4.7-6.6 | 4.5 | 3.6-5.5 |
| | GA-1 | 1.0 | 12.1 | 9.4-15.7 | 9.6 | 8.3-11.1 |
| | GA-2.5 | 2.5 | 23.0 | 17-31.2 | 15.4 | 11.6-20.4 |
| | GA-5 | 5.0 | 28.6 | 18.7-43.6 | 19.8 | 13.1-29.9 |
| | GA-10 | 10 | 28.8 | 11.4-72.6 | 18.3 | 7.6-44.3 |
| | GA-20 | 20 | 32.5 | 27.9-37.9 | 21.3 | 18-25.1 |
| | DCCM1 | NA | 1.0 | 0.8-1.3 | 1.0 | 0.8-1.3 |
| | ConA | 2.5 | 26.2 | 21.8-31.4 | 27.0 | 23.6-30.8 |
| M4 Plate 4 | GA-0.3 | 0.3 | 3.9 | 2-7.5 | 2.8 | 1.6-5 |
| | GA-1 | 1.0 | 4.0 | 2.7-5.9 | 3.1 | 2.3-4.2 |
| | GA-2.5 | 2.5 | 8.7 | 4.4-17.1 | 6.2 | 3-13 |
| | GA-5 | 5.0 | 10.0 | 6.5-15.6 | 6.3 | 4.1-9.7 |
| | GA-10 | 10 | 8.6 | 4.7-15.5 | 5.6 | 3.1-10.1 |
| | GA-20 | 20 | 9.3 | 7.8-11 | 6.4 | 5.1-8 |
| | DCCM1 | NA | 1.0 | 0.8-1.3 | 1.0 | 0.7-1.3 |
| | ConA | 2.5 | 28.8 | 22.5-36.8 | 27.6 | 21.4-35.4 |

TABLE 58

Expression of Mouse IL-5 from Primary LN Cells in Response to GA Stimulation (Plate 1: C1-C3)

| GA | Stimulation | Conc. (µg/mL) | IL-5 mRNA/GAPDH | | IL-5 mRNA/B-Actin | |
|---|---|---|---|---|---|---|
| | | | Fold Change | Induction Range | Fold Change | Induction Range |
| C1 | GA-0.3 | 0.3 | 3.9 | 3.2-4.9 | 3.4 | 2.8-4.3 |
| | GA-1 | 1.0 | 8.6 | 5.6-13.2 | 6.9 | 4.6-10.4 |
| | GA-2.5 | 2.5 | 18.6 | 12.5-27.8 | 14.3 | 9.7-21.2 |
| | GA-5 | 5.0 | 19.4 | 13.1-28.9 | 15.2 | 10.3-22.6 |
| | GA-10 | 10 | 21.6 | 17.4-26.8 | 18.8 | 16.3-21.8 |
| | GA-20 | 20 | 26.5 | 21.1-33.3 | 22.2 | 17.5-28.2 |
| | DCCM1 | NA | 1.0 | 0.5-1.9 | 1.0 | 0.5-1.9 |
| | ConA | 2.5 | 25.7 | 23.3-28.3 | 26.8 | 23.8-30.2 |
| C2 | GA-0.3 | 0.3 | 3.9 | 2.4-6.3 | 3.5 | 2.2-5.8 |
| | GA-1 | 1.0 | 10.0 | 5.8-17.4 | 8.9 | 5.2-15.3 |
| | GA-2.5 | 2.5 | 15.3 | 9-26.3 | 13.2 | 7.7-22.7 |
| | GA-5 | 5.0 | 25.0 | 16.4-38.1 | 20.0 | 13-30.8 |
| | GA-10 | 10 | 26.0 | 16.7-40.4 | 22.7 | 14.6-35.2 |
| | GA-20 | 20 | 24.3 | 15.2-38.9 | 20.0 | 12.5-32.1 |
| | DCCM1 | NA | 1.0 | 0.7-1.5 | 1.0 | 0.7-1.5 |
| | ConA | 2.5 | 32.7 | 19.6-54.6 | 39.9 | 25.1-63.5 |
| C3 | GA-0.3 | 0.3 | 3.1 | 1.7-5.8 | 2.5 | 1.4-4.7 |
| | GA-1 | 1.0 | 8.5 | 4.7-15.4 | 6.8 | 3.7-12.4 |
| | GA-2.5 | 2.5 | 13.2 | 9.4-18.6 | 11.3 | 7.4-17.5 |
| | GA-5 | 5.0 | 15.9 | 12.1-20.8 | 11.9 | 9.3-15.3 |
| | GA-10 | 10 | 23.3 | 12.9-41.9 | 16.7 | 9-31 |
| | GA-20 | 20 | 19.5 | 15.4-24.7 | 15.6 | 11.3-21.5 |
| | DCCM1 | NA | 1.0 | 0.8-1.3 | 1.0 | 0.8-1.2 |
| | ConA | 2.5 | 22.2 | 20.2-24.4 | 19.8 | 16.7-23.6 |

TABLE 59

Expression of Mouse IL-5 from Primary LN Cells in Response to GA Stimulation (Plate 2: C4-C6)

| GA | Stimulation | Conc. (µg/mL) | IL-5 mRNA/GAPDH Fold Change | IL-5 mRNA/GAPDH Induction Range | IL-5 mRNA/B-Actin Fold Change | IL-5 mRNA/B-Actin Induction Range |
|---|---|---|---|---|---|---|
| C4 | GA-0.3 | 0.3 | 5.2 | 3.5-7.7 | 5.5 | 4.4-6.9 |
| | GA-1 | 1.0 | 7.9 | 5.3-11.8 | 8.0 | 5.6-11.6 |
| | GA-2.5 | 2.5 | 12.1 | 8.9-16.4 | 9.7 | 7.2-13.2 |
| | GA-5 | 5.0 | 23.4 | 16-34.2 | 17.8 | 11.8-26.7 |
| | GA-10 | 10 | 18.7 | 8.4-41.5 | 14.7 | 6.7-32.3 |
| | GA-20 | 20 | 19.9 | 18-22 | 33.9 | 21.1-54.3 |
| | DCCM1 | NA | 1.0 | 0.7-1.4 | 1.0 | 0.9-1.1 |
| | ConA | 2.5 | 20.8 | 12.7-33.9 | 35.5 | 24.9-50.7 |
| C5 | GA-0.3 | 0.3 | 5.0 | 3.4-7.2 | 3.4 | 2.4-4.9 |
| | GA-1 | 1.0 | 7.7 | 5-11.7 | 5.0 | 3.3-7.5 |
| | GA-2.5 | 2.5 | 20.4 | 11.7-35.6 | 12.8 | 7.2-22.6 |
| | GA-5 | 5.0 | 23.3 | 13.7-39.5 | 14.4 | 8.5-24.3 |
| | GA-10 | 10 | 20.6 | 12.7-33.3 | 18.5 | 12.1-28.2 |
| | GA-20 | 20 | 18.9 | 12.1-29.3 | 13.3 | 9.1-19.4 |
| | DCCM1 | NA | 1.0 | 0.8-1.2 | 1.0 | 0.9-1.2 |
| | ConA | 2.5 | 26.0 | 20.6-32.9 | 26.9 | 21.1-34.3 |
| C6 | GA-0.3 | 0.3 | 3.6 | 2.4-5.3 | 2.4 | 1.7-3.5 |
| | GA-1 | 1.0 | 7.1 | 4.5-11.4 | 4.7 | 2.9-7.4 |
| | GA-2.5 | 2.5 | 12.6 | 5.6-28.3 | 8.8 | 4.1-18.9 |
| | GA-5 | 5.0 | 19.3 | 14.5-25.9 | 14.0 | 10-19.6 |
| | GA-10 | 10 | 29.2 | 20.9-40.8 | 22.2 | 14.7-33.6 |
| | GA-20 | 20 | 28.2 | 16-49.6 | 22.1 | 13.5-36.2 |
| | DCCM1 | NA | 1.0 | 0.5-2.2 | 1.0 | 0.5-2.2 |
| | ConA | 2.5 | 25.2 | 16.8-37.9 | 27.3 | 19.5-38.3 |

TABLE 60

Expression of Mouse IL-5 from Primary LN Cells in Response to GA Stimulation (Plate 3: C7-C8)

| GA | Stimulation | Conc. (µg/mL) | IL-5 mRNA/GAPDH Fold Change | IL-5 mRNA/GAPDH Induction Range | IL-5 mRNA/B-Actin Fold Change | IL-5 mRNA/B-Actin Induction Range |
|---|---|---|---|---|---|---|
| C7 | GA-0.3 | 0.3 | 3.6 | 2-6.4 | 2.3 | 1.8-3 |
| | GA-1 | 1.0 | 15.5 | 10.2-23.4 | 9.2 | 6.5-13.1 |
| | GA-2.5 | 2.5 | 27.2 | 18-41 | 16.8 | 13.4-21.2 |
| | GA-5 | 5.0 | 32.5 | 17.3-61 | 17.2 | 9-33.1 |
| | GA-10 | 10 | 29.1 | 16.9-50.3 | 15.9 | 9-28 |
| | GA-20 | 20 | 40.2 | 23.9-67.7 | 22.9 | 14.2-36.9 |
| | DCCM1 | NA | 1.0 | 0.6-1.6 | 1.0 | 0.6-1.7 |
| | ConA | 2.5 | 30.3 | 21.3-43.1 | 24.8 | 19-32.5 |
| C8 | GA-0.3 | 0.3 | 5.7 | 3.9-8.1 | 3.5 | 2.4-5 |
| | GA-1 | 1.0 | 13.1 | 8.9-19.3 | 7.9 | 5.4-11.6 |
| | GA-2.5 | 2.5 | 23.6 | 17.9-31.2 | 13.8 | 10.7-17.9 |
| | GA-5 | 5.0 | 28.5 | 18.5-44 | 17.4 | 11.6-25.9 |
| | GA-10 | 10 | 26.6 | 17-41.7 | 16.8 | 10.4-27 |
| | GA-20 | 20 | 32.1 | 26.5-38.9 | 19.4 | 16-23.4 |
| | DCCM1 | NA | 1.0 | 0.8-1.2 | 1.0 | 0.8-1.3 |
| | ConA | 2.5 | 29.3 | 18.8-45.8 | 26.8 | 18.3-39.1 |

TABLE 61

Expression of Mouse IL-5 from Primary LN Cells in Response to GA Stimulation (Plate 1-3: M1-M4)

| GA | Stimulation | Conc. (µg/mL) | IL-5 mRNA/GAPDH Fold Change | IL-5 mRNA/GAPDH Induction Range | IL-5 mRNA/B-Actin Fold Change | IL-5 mRNA/B-Actin Induction Range |
|---|---|---|---|---|---|---|
| M1 Plate 1 | GA-0.3 | 0.3 | 4.7 | 3.1-7.2 | 4.0 | 2.6-6.2 |
| | GA-1 | 1.0 | 6.2 | 3.8-10.1 | 5.5 | 3.3-9 |
| | GA-2.5 | 2.5 | 16.7 | 10-28.2 | 13.1 | 8-21.4 |
| | GA-5 | 5.0 | 17.6 | 11.9-26 | 14.3 | 9.7-21.3 |
| | GA-10 | 10 | 19.1 | 9.2-39.7 | 14.9 | 7.4-30.2 |
| | GA-20 | 20 | 20.9 | 15.6-27.9 | 17.5 | 13.6-22.5 |
| | DCCM1 | NA | 1.0 | 0.8-1.3 | 1.0 | 0.8-1.3 |
| | ConA | 2.5 | 23.6 | 21.7-25.8 | 23.6 | 22.3-25.1 |
| M2 Plate 2 | GA-0.3 | 0.3 | 3.5 | 1.7-7 | 2.7 | 1.4-5.3 |
| | GA-1 | 1.0 | 5.8 | 4-8.3 | 4.3 | 3-6.1 |
| | GA-2.5 | 2.5 | 15.0 | 8.5-26.7 | 11.0 | 6.2-19.7 |
| | GA-5 | 5.0 | 23.7 | 14.4-39.3 | 18.5 | 11.7-29.2 |
| | GA-10 | 10 | 17.3 | 11.4-26.1 | 13.4 | 9.1-19.6 |
| | GA-20 | 20 | 21.7 | 14.9-31.7 | 17.3 | 11.7-25.6 |
| | DCCM1 | NA | 1.0 | 0.8-1.2 | 1.0 | 0.9-1.1 |
| | ConA | 2.5 | 20.0 | 16.2-24.8 | 20.9 | 16.4-26.6 |
| M3 Plate 3 | GA-0.3 | 0.3 | 4.2 | 3.2-5.5 | 3.4 | 2.5-4.5 |
| | GA-1 | 1.0 | 6.9 | 5-9.5 | 5.5 | 4.3-7 |
| | GA-2.5 | 2.5 | 16.5 | 9.4-28.9 | 11.0 | 6.4-19.1 |
| | GA-5 | 5.0 | 19.1 | 11.9-30.4 | 13.2 | 8.4-20.9 |
| | GA-10 | 10 | 32.3 | 17.6-59.3 | 20.6 | 12-35.3 |
| | GA-20 | 20 | 19.0 | 16.1-22.4 | 12.4 | 10.4-14.8 |
| | DCCM1 | NA | 1.0 | 0.7-1.4 | 1.0 | 0.7-1.4 |
| | ConA | 2.5 | 20.6 | 17.6-24.1 | 21.3 | 19.3-23.4 |
| M4 Plate 3 | GA-0.3 | 0.3 | 2.4 | 1.4-4 | 1.7 | 1.2-2.6 |
| | GA-1 | 1.0 | 3.3 | 1.7-6.5 | 2.6 | 1.4-4.8 |
| | GA-2.5 | 2.5 | 5.1 | 3-8.6 | 3.7 | 2-6.7 |
| | GA-5 | 5.0 | 3.8 | 1.9-7.6 | 2.4 | 1.2-4.7 |
| | GA-10 | 10 | 7.9 | 5.5-11.4 | 5.2 | 3.6-7.4 |
| | GA-20 | 20 | 6.9 | 4.2-11.3 | 4.8 | 2.9-8 |
| | DCCM1 | NA | 1.0 | 0.6-1.6 | 1.0 | 0.6-1.6 |
| | ConA | 2.5 | 22.3 | 18.6-26.8 | 21.4 | 17.7-25.8 |

TABLE 62

Expression of Mouse IL-13 from Primary LN Cells in Response to GA Stimulation (Plate 1: C1-C3)

| GA | Stimulation | Conc. (µg/mL) | IL-13 mRNA/GAPDH Fold Change | IL-13 mRNA/GAPDH Induction Range | IL-13 mRNA/B-Actin Fold Change | IL-13 mRNA/B-Actin Induction Range |
|---|---|---|---|---|---|---|
| C1 | GA-0.3 | 0.3 | 4.1 | 3-5.5 | 3.6 | 2.6-4.8 |
| | GA-1 | 1.0 | 13.4 | 10.4-17.3 | 10.7 | 8.6-13.4 |
| | GA-2.5 | 2.5 | 23.8 | 15.7-36.1 | 18.3 | 12.2-27.5 |
| | GA-5 | 5.0 | 23.7 | 16-35 | 18.6 | 12.6-27.4 |
| | GA-10 | 10 | 29.2 | 21.9-38.8 | 25.5 | 20.1-32.3 |
| | GA-20 | 20 | 30.8 | 25.7-36.9 | 25.8 | 21.3-31.4 |
| | DCCM1 | NA | 1.0 | 0.7-1.4 | 1.0 | 0.7-1.4 |
| | ConA | 2.5 | 26.5 | 24-29.2 | 27.7 | 24.5-31.2 |
| C2 | GA-0.3 | 0.3 | 5.2 | 3.3-8 | 4.7 | 3-7.4 |
| | GA-1 | 1.0 | 13.2 | 9.9-17.8 | 11.8 | 9-15.4 |
| | GA-2.5 | 2.5 | 19.8 | 12.6-31.1 | 17.0 | 10.8-26.9 |
| | GA-5 | 5.0 | 29.1 | 19.8-42.6 | 23.3 | 15.7-34.5 |
| | GA-10 | 10 | 27.0 | 21.7-33.5 | 23.6 | 19.2-29 |
| | GA-20 | 20 | 31.1 | 23-42.2 | 25.6 | 18.8-34.8 |
| | DCCM1 | NA | 1.0 | 0.8-1.3 | 1.0 | 0.8-1.3 |
| | ConA | 2.5 | 24.0 | 18.9-30.6 | 29.3 | 26.3-32.7 |
| C3 | GA-0.3 | 0.3 | 5.2 | 3.3-8.3 | 4.3 | 2.7-6.7 |
| | GA-1 | 1.0 | 14.8 | 9.4-23.3 | 11.9 | 7.5-18.9 |
| | GA-2.5 | 2.5 | 17.7 | 12-26.2 | 15.3 | 9.5-24.4 |
| | GA-5 | 5.0 | 25.2 | 20.2-31.4 | 19.0 | 15.7-22.9 |
| | GA-10 | 10 | 31.6 | 19.1-52.2 | 22.7 | 13.3-38.7 |
| | GA-20 | 20 | 26.6 | 20.1-35.1 | 21.2 | 14.8-30.3 |
| | DCCM1 | NA | 1.0 | 0.6-1.6 | 1.0 | 0.6-1.6 |
| | ConA | 2.5 | 28.0 | 24.9-31.5 | 25.0 | 20.8-30.2 |

TABLE 63

Expression of Mouse IL-13 from Primary LN Cells in Response to GA Stimulation (Plate 2: C4-C6)

| GA | Stimulation | Conc. (μg/mL) | IL-13 mRNA/GAPDH Fold Change | IL-13 mRNA/GAPDH Induction Range | IL-13 mRNA/B-Actin Fold Change | IL-13 mRNA/B-Actin Induction Range |
|---|---|---|---|---|---|---|
| C4 | GA-0.3 | 0.3 | 9.7 | 6.8-13.8 | 10.3 | 9.2-11.5 |
| | GA-1 | 1.0 | 17.3 | 12.3-24.4 | 17.6 | 13-23.8 |
| | GA-2.5 | 2.5 | 31.6 | 23.7-42.2 | 25.5 | 19.1-33.9 |
| | GA-5 | 5.0 | 55.7 | 49.8-62.4 | 42.3 | 35.1-50.9 |
| | GA-10 | 10 | 46.3 | 26.8-80 | 36.4 | 21.4-62 |
| | GA-20 | 20 | 29.5 | 15.7-55.5 | 50.3 | 23-109.8 |
| | DCCM1 | NA | 1.0 | 0.5-2 | 1.0 | 0.5-1.9 |
| | ConA | 2.5 | 28.9 | 20-41.8 | 49.5 | 42.9-57.1 |
| C5 | GA-0.3 | 0.3 | 9.2 | 7-12.1 | 6.3 | 4.8-8.3 |
| | GA-1 | 1.0 | 20.2 | 15.1-27 | 13.1 | 10-17.2 |
| | GA-2.5 | 2.5 | 29.8 | 26.9-33.1 | 18.7 | 16.1-21.8 |
| | GA-5 | 5.0 | 47.4 | 30.9-72.8 | 29.4 | 19.3-44.6 |
| | GA-10 | 10 | 28.5 | 15.3-53.1 | 25.5 | 14.3-45.7 |
| | GA-20 | 20 | 33.3 | 21.4-51.8 | 23.4 | 16-34.2 |
| | DCCM1 | NA | 1.0 | 0.7-1.5 | 1.0 | 0.7-1.5 |
| | ConA | 2.5 | 36.0 | 29-44.7 | 37.3 | 29.7-46.8 |
| C6 | GA-0.3 | 0.3 | 8.6 | 7-10.4 | 5.8 | 4.8-6.9 |
| | GA-1 | 1.0 | 14.7 | 11.3-19.1 | 9.6 | 7.4-12.4 |
| | GA-2.5 | 2.5 | 22.9 | 11.4-45.8 | 16.0 | 8.4-30.3 |
| | GA-5 | 5.0 | 33.0 | 28.3-38.5 | 23.9 | 19-30 |
| | GA-10 | 10 | 42.4 | 27.8-64.9 | 32.3 | 19.8-52.6 |
| | GA-20 | 20 | 35.9 | 24.6-52.3 | 28.2 | 21.9-36.3 |
| | DCCM1 | NA | 1.0 | 0.8-1.2 | 1.0 | 0.8-1.2 |
| | ConA | 2.5 | 29.6 | 20-43.8 | 32.0 | 23.2-44.2 |

TABLE 64

Expression of Mouse IL-13 from Primary LN Cells in Response to GA Stimulation (Plate 3: C7-C8)

| GA | Stimulation | Conc. (μg/mL) | IL-13 mRNA/GAPDH Fold Change | IL-13 mRNA/GAPDH Induction Range | IL-13 mRNA/B-Actin Fold Change | IL-13 mRNA/B-Actin Induction Range |
|---|---|---|---|---|---|---|
| C7 | GA-0.3 | 0.3 | 10.2 | 5.6-18.6 | 6.6 | 4.8-9.1 |
| | GA-1 | 1.0 | 32.9 | 25.4-42.7 | 19.6 | 17-22.6 |
| | GA-2.5 | 2.5 | 49.4 | 29.5-82.9 | 30.6 | 20.8-45.1 |
| | GA-5 | 5.0 | 60.6 | 39.9-92 | 32.1 | 20.5-50.3 |
| | GA-10 | 10 | 55.6 | 38.3-80.8 | 30.2 | 20.1-45.4 |
| | GA-20 | 20 | 66.8 | 45.9-97.3 | 38.1 | 27.9-52 |
| | DCCM1 | NA | 1.0 | 0.6-1.6 | 1.0 | 0.6-1.7 |
| | ConA | 2.5 | 53.4 | 41.5-68.9 | 43.8 | 39.2-48.8 |
| C8 | GA-0.3 | 0.3 | 7.0 | 5-10 | 4.4 | 3.1-6.2 |
| | GA-1 | 1.0 | 20.7 | 15.8-27 | 12.5 | 9.6-16.3 |
| | GA-2.5 | 2.5 | 37.1 | 28.7-48.1 | 21.7 | 17.1-27.5 |
| | GA-5 | 5.0 | 39.7 | 26.3-60 | 24.2 | 16.6-35.3 |
| | GA-10 | 10 | 42.5 | 30.7-58.9 | 26.8 | 18.6-38.5 |
| | GA-20 | 20 | 45.3 | 38-53.9 | 27.3 | 22.9-32.4 |
| | DCCM1 | NA | 1.0 | 0.7-1.5 | 1.0 | 0.6-1.6 |
| | ConA | 2.5 | 37.9 | 24.8-57.9 | 34.6 | 24.3-49.2 |

TABLE 65

Expression of Mouse IL-13 from Primary LN Cells in Response to GA Stimulation (Plate 1-3: M1-M4)

| GA | Stimulation | Conc. (μg/mL) | IL-13 mRNA/GAPDH Fold Change | IL-13 mRNA/GAPDH Induction Range | IL-13 mRNA/B-Actin Fold Change | IL-13 mRNA/B-Actin Induction Range |
|---|---|---|---|---|---|---|
| M1 Plate 1 | GA-0.3 | 0.3 | 6.9 | 5-9.5 | 5.7 | 4.2-7.7 |
| | GA-1 | 1.0 | 14.8 | 12.3-17.8 | 11.8 | 9.7-14.3 |
| | GA-2.5 | 2.5 | 21.0 | 12.3-35.7 | 15.7 | 9.7-25.3 |
| | GA-5 | 5.0 | 31.4 | 21.6-45.8 | 25.2 | 17.4-36.4 |
| | GA-10 | 10 | 34.0 | 16.9-68.6 | 25.7 | 13.1-50.7 |
| | GA-20 | 20 | 25.9 | 19.9-33.7 | 20.9 | 16.6-26.2 |
| | DCCM1 | NA | 1.0 | 0.7-1.4 | 1.0 | 0.7-1.4 |
| | ConA | 2.5 | 32.7 | 29.1-36.8 | 35.9 | 33.4-38.5 |
| M2 Plate 2 | GA-0.3 | 0.3 | 12.3 | 6.2-24.4 | 8.3 | 6.2-11.2 |
| | GA-1 | 1.0 | 15.4 | 11.5-20.7 | 12.4 | 9.4-16.3 |
| | GA-2.5 | 2.5 | 39.1 | 19.9-76.8 | 30.6 | 16.1-58.3 |
| | GA-5 | 5.0 | 44.1 | 25.6-75.9 | 36.5 | 22.9-58 |
| | GA-10 | 10 | 33.6 | 22.8-49.6 | 26.7 | 18.3-38.8 |
| | GA-20 | 20 | 39.4 | 27.5-56.5 | 33.6 | 24.3-46.6 |
| | DCCM1 | NA | 1.0 | 0.6-1.6 | 1.0 | 0.6-1.6 |
| | ConA | 2.5 | 38.4 | 34-43.4 | 42.6 | 36.7-49.5 |
| M3 Plate 3 | GA-0.3 | 0.3 | 7.1 | 6.2-8.1 | 5.8 | 5.5-6.3 |
| | GA-1 | 1.0 | 16.8 | 12.5-22.4 | 13.5 | 10.9-16.7 |
| | GA-2.5 | 2.5 | 30.7 | 22.1-42.5 | 19.7 | 14.6-26.7 |
| | GA-5 | 5.0 | 37.2 | 26.2-52.7 | 23.4 | 17.2-31.7 |
| | GA-10 | 10 | 32.1 | 10.4-98.6 | 21.8 | 7.3-65.3 |
| | GA-20 | 20 | 31.4 | 26.8-36.9 | 21.6 | 18.5-25.1 |
| | DCCM1 | NA | 1.0 | 0.8-1.2 | 1.0 | 0.8-1.2 |
| | ConA | 2.5 | 26.3 | 21.5-32.2 | 30.1 | 24.9-36.3 |
| M4 Plate 3 | GA-0.3 | 0.3 | 5.1 | 2.7-9.4 | 4.0 | 2.3-6.8 |
| | GA-1 | 1.0 | 5.1 | 3.3-8 | 4.5 | 3.2-6.4 |
| | GA-2.5 | 2.5 | 11.2 | 5.1-24.4 | 7.7 | 3.5-16.9 |
| | GA-5 | 5.0 | 7.3 | 4-13.2 | 4.9 | 2.9-8.3 |
| | GA-10 | 10 | 10.9 | 6.8-17.4 | 7.7 | 4.9-12 |
| | GA-20 | 20 | 12.3 | 8.3-18.1 | 8.4 | 5.9-12 |
| | DCCM1 | NA | 1.0 | 0.9-1.1 | 1.0 | 0.8-1.2 |
| | ConA | 2.5 | 27.2 | 21.2-34.9 | 29.3 | 23.6-36.5 |

TABLE 66

Expression of Mouse IL-2 from Primary LN Cells in Response to GA Stimulation (Plate 1-2: C3, C6, M1, M2)

| GA | Stimulation | Conc. (μg/mL) | IL-2 mRNA/GAPDH Fold Change | IL-2 mRNA/GAPDH Induction Range | IL-2 mRNA/B-Actin Fold Change | IL-2 mRNA/B-Actin Induction Range |
|---|---|---|---|---|---|---|
| C3 | GA-0.3 | 0.3 | 3.6 | 3.1-4.3 | 3.3 | 2.8-3.9 |
| | GA-1 | 1.0 | 11.6 | 10-13.4 | 10.2 | 8.7-12.1 |
| | GA-2.5 | 2.5 | 16.3 | 13-20.5 | 14.2 | 10.7-18.9 |
| | GA-5 | 5.0 | 24.9 | 21.4-29 | 20.5 | 17.7-23.7 |
| | GA-10 | 10 | 34.5 | 27.5-43.2 | 27.5 | 22.1-34.3 |
| | GA-20 | 20 | 39.0 | 31.6-48.2 | 32.7 | 29.2-36.7 |
| | DCCM1 | NA | 1.0 | 0.8-1.2 | 1.0 | 0.8-1.2 |
| | ConA | 2.5 | 103.2 | 94.5-112.7 | 109.3 | 97-123.2 |
| M1 | GA-0.3 | 0.3 | 4.7 | 3.8-5.8 | 4.4 | 3.6-5.3 |
| | GA-1 | 1.0 | 11.4 | 10.3-12.7 | 9.5 | 8.4-10.8 |
| | GA-2.5 | 2.5 | 22.8 | 15.6-33.3 | 17.3 | 12.3-24.3 |
| | GA-5 | 5.0 | 27.4 | 18.5-40.7 | 22.4 | 15.3-32.9 |
| | GA-10 | 10 | 37.8 | 20.8-68.6 | 30.2 | 17.1-53.5 |
| | GA-20 | 20 | 44.6 | 41.1-48.4 | 38.6 | 35.5-41.9 |
| | DCCM1 | NA | 1.0 | 0.7-1.5 | 1.0 | 0.7-1.5 |
| | ConA | 2.5 | 111.7 | 107.2-116.5 | 120.1 | 114.1-126.4 |
| C6 | GA-0.3 | 0.3 | 6.9 | 5.8-8.1 | 6.2 | 5.3-7.1 |
| | GA-1 | 1.0 | 12.9 | 8.7-19.1 | 9.7 | 6.4-14.5 |
| | GA-2.5 | 2.5 | 24.8 | 12.7-48.5 | 12.3 | 5.7-26.5 |
| | GA-5 | 5.0 | 22.3 | 13.3-37.5 | 15.6 | 9.3-26 |
| | GA-10 | 10 | 28.3 | 19-42.4 | 18.9 | 12.8-27.8 |
| | GA-20 | 20 | 32.9 | 19-56.9 | 21.7 | 13-36.3 |
| | DCCM1 | NA | 1.0 | 0.8-1.3 | 1.0 | 0.9-1.1 |
| | ConA | 2.5 | 82.0 | 61.7-109 | 75.2 | 57.9-97.7 |
| M2 | GA-0.3 | 0.3 | 4.0 | 2.6-6.2 | 3.1 | 2-4.9 |
| | GA-1 | 1.0 | 11.8 | 8.3-16.7 | 8.6 | 6.1-12.1 |

TABLE 66-continued

Expression of Mouse IL-2 from Primary LN Cells in Response to GA Stimulation (Plate 1-2: C3, C6, M1, M2)

| GA | Stimulation | Conc. (µg/mL) | IL-2 mRNA/GAPDH Fold Change | IL-2 mRNA/GAPDH Induction Range | IL-2 mRNA/B-Actin Fold Change | IL-2 mRNA/B-Actin Induction Range |
|---|---|---|---|---|---|---|
| | GA-2.5 | 2.5 | 21.6 | 17.3-26.9 | 18.6 | 12.9-26.8 |
| | GA-5 | 5.0 | 23.8 | 18.4-30.7 | 17.3 | 13.5-22.2 |
| | GA-10 | 10 | 34.1 | 20.6-56.4 | 25.8 | 15.5-43.1 |
| | GA-20 | 20 | 36.6 | 23.3-57.3 | 28.1 | 18-43.9 |
| | DCCM1 | NA | 1.0 | 0.7-1.4 | 1.0 | 0.8-1.3 |
| | ConA | 2.5 | 84.8 | 75.4-95.3 | 81.3 | 69.7-94.8 |

TABLE 67

Expression of Mouse IL-2 from Primary LN Cells in Response to GA Stimulation (Plate 3: C7-C8, M3-M4)

| GA | Stimulation | Conc. (µg/mL) | IL-2 mRNA/GAPDH Fold Change | IL-2 mRNA/GAPDH Induction Range | IL-2 mRNA/B-Actin Fold Change | IL-2 mRNA/B-Actin Induction Range |
|---|---|---|---|---|---|---|
| C7 | GA-0.3 | 0.3 | 5.6 | 3.4-9.2 | 3.9 | 3.4-4.4 |
| | GA-1 | 1.0 | 19.0 | 16.1-22.6 | 10.8 | 10.1-11.6 |
| | GA-2.5 | 2.5 | 31.4 | 22.9-43 | 19.7 | 17.7-22 |
| | GA-5 | 5.0 | 51.1 | 37.8-69.1 | 24.7 | 18.5-33 |
| | GA-10 | 10 | 58.2 | 45.4-74.7 | 29.1 | 22.2-38.2 |
| | GA-20 | 20 | 70.8 | 49.9-100.7 | 38.2 | 27.8-52.5 |
| | DCCM1 | NA | 1.0 | 0.7-1.4 | 1.0 | 0.8-1.3 |
| | ConA | 2.5 | 158.0 | 131.5-189.8 | 103.6 | 81.2-132.1 |
| C8 | GA-0.3 | 0.3 | 6.4 | 4.9-8.3 | 3.8 | 3-4.8 |
| | GA-1 | 1.0 | 15.9 | 14-18.1 | 9.4 | 8.4-10.5 |
| | GA-2.5 | 2.5 | 29.8 | 24.2-36.7 | 16.0 | 13.2-19.4 |
| | GA-5 | 5.0 | 44.3 | 34.3-57.4 | 23.3 | 18.6-29.2 |
| | GA-10 | 10 | 50.9 | 42.2-61.4 | 28.7 | 27-30.6 |
| | GA-20 | 20 | 60.4 | 55.2-66.1 | 33.7 | 31.6-35.9 |
| | DCCM1 | NA | 1.0 | 0.8-1.3 | 1.0 | 0.7-1.5 |
| | ConA | 2.5 | 127.7 | 99.5-163.8 | 101.9 | 81.4-127.4 |
| M3 | GA-0.3 | 0.3 | 4.3 | 3.9-4.8 | 3.5 | 3.2-3.8 |
| | GA-1 | 1.0 | 11.8 | 9.4-14.8 | 8.8 | 8.2-9.4 |
| | GA-2.5 | 2.5 | 27.4 | 19.5-38.5 | 17.6 | 12.8-24.1 |
| | GA-5 | 5.0 | 35.3 | 20.9-59.7 | 21.1 | 13.1-34 |
| | GA-10 | 10 | 42.3 | 33.2-53.9 | 27.7 | 20.5-37.5 |
| | GA-20 | 20 | 46.7 | 37.8-57.7 | 29.8 | 24.4-36.5 |
| | DCCM1 | NA | 1.0 | 0.8-1.2 | 1.0 | 0.8-1.3 |
| | ConA | 2.5 | 102.6 | 76.9-136.9 | 92.2 | 69.4-122.7 |
| M4 | GA-0.3 | 0.3 | 5.2 | 3.1-8.8 | 3.4 | 2.2-5.5 |
| | GA-1 | 1.0 | 7.5 | 5.6-10.1 | 5.3 | 4.6-6.2 |
| | GA-2.5 | 2.5 | 15.0 | 9.1-24.7 | 9.2 | 5.4-15.8 |
| | GA-5 | 5.0 | 16.0 | 9.4-27.3 | 8.8 | 5.1-15.1 |
| | GA-10 | 10 | 11.5 | 7.5-17.6 | 6.5 | 4.3-9.7 |
| | GA-20 | 20 | 10.4 | 7.6-14.2 | 5.9 | 4.3-8.2 |
| | DCCM1 | NA | 1.0 | 0.8-1.3 | 1.0 | 0.8-1.3 |
| | ConA | 2.5 | 127.5 | 98.3-165.3 | 98.9 | 85.3-114.6 |

TABLE 68

Expression of Mouse IL-17 from Primary LN Cells in Response to GA Stimulation (Plate 1-2: C3, C6, M1, M2)

| GA | Stimulation | Conc. (µg/mL) | IL-17 mRNA/GAPDH Fold Change | IL-17 mRNA/GAPDH Induction Range | IL-17 mRNA/B-Actin Fold Change | IL-17 mRNA/B-Actin Induction Range |
|---|---|---|---|---|---|---|
| C3 | GA-0.3 | 0.3 | 2.0 | 1.1-3.4 | 1.8 | 1-3.1 |
| | GA-1 | 1.0 | 4.8 | 3.4-6.7 | 4.2 | 3-6 |
| | GA-2.5 | 2.5 | 10.2 | 8.4-12.3 | 8.8 | 6.8-11.4 |
| | GA-5 | 5.0 | 15.7 | 11.8-20.8 | 12.9 | 9.8-17.1 |
| | GA-10 | 10 | 13.8 | 10.1-18.9 | 11.0 | 8.1-15 |
| | GA-20 | 20 | 15.7 | 10.5-23.5 | 13.2 | 9.2-18.9 |
| | DCCM1 | NA | 1.0 | 0.6-1.6 | 1.0 | 0.6-1.6 |
| | ConA | 2.5 | 125.8 | 118.7-133.2 | 133.2 | 120.6-147.2 |
| M1 | GA-0.3 | 0.3 | 3.0 | 1.9-4.8 | 2.8 | 1.8-4.4 |
| | GA-1 | 1.0 | 9.5 | 7.8-11.5 | 7.9 | 6.5-9.7 |
| | GA-2.5 | 2.5 | 14.0 | 8.9-22 | 10.6 | 6.9-16.1 |
| | GA-5 | 5.0 | 20.9 | 13.3-32.7 | 17.1 | 11-26.5 |
| | GA-10 | 10 | 21.7 | 10.9-42.9 | 17.3 | 9-33.6 |
| | GA-20 | 20 | 21.5 | 19.4-23.7 | 18.6 | 16.8-20.5 |
| | DCCM1 | NA | 1.0 | 0.7-1.5 | 1.0 | 0.7-1.5 |
| | ConA | 2.5 | 208.6 | 188.8-230.4 | 224.2 | 202-248.8 |
| C6 | GA-0.3 | 0.3 | 5.3 | 3.1-8.9 | 4.7 | 2.8-7.9 |
| | GA-1 | 1.0 | 13.1 | 7.7-22.3 | 9.8 | 5.7-16.9 |
| | GA-2.5 | 2.5 | 15.0 | 9.3-24.3 | 7.4 | 4-13.7 |
| | GA-5 | 5.0 | 20.0 | 13.1-30.4 | 13.9 | 9.2-21.1 |
| | GA-10 | 10 | 17.5 | 11.5-26.6 | 11.6 | 7.7-17.5 |
| | GA-20 | 20 | 16.6 | 8.6-31.9 | 11.0 | 5.9-20.5 |
| | DCCM1 | NA | 1.0 | 0.4-2.2 | 1.0 | 0.5-2.2 |
| | ConA | 2.5 | 139.9 | 116.5-168 | 128.3 | 111.1-148.3 |
| M2 | GA-0.3 | 0.3 | 5.2 | 3.3-8.3 | 4.1 | 2.6-6.5 |
| | GA-1 | 1.0 | 8.0 | 6.1-10.4 | 5.8 | 4.4-7.6 |
| | GA-2.5 | 2.5 | 15.6 | 11.5-21.1 | 13.4 | 8.8-20.4 |
| | GA-5 | 5.0 | 19.7 | 12.9-30.2 | 14.4 | 9.4-21.9 |
| | GA-10 | 10 | 24.1 | 17.1-34.1 | 18.3 | 12.8-26.1 |
| | GA-20 | 20 | 19.4 | 13.6-27.8 | 14.9 | 10.5-21.3 |
| | DCCM1 | NA | 1.0 | 0.6-1.7 | 1.0 | 0.6-1.6 |
| | ConA | 2.5 | 213.0 | 206.8-219.3 | 204.1 | 183.9-226.6 |

TABLE 69

Expression of Mouse IL-17 from Primary LN Cells in Response to GA Stimulation (Plate 3: C7-C8, M3-M4)

| GA | Stimulation | Conc. (µg/mL) | IL-17 mRNA/GAPDH Fold Change | IL-17 mRNA/GAPDH Induction Range | IL-17 mRNA/B-Actin Fold Change | IL-17 mRNA/B-Actin Induction Range |
|---|---|---|---|---|---|---|
| C7 | GA-0.3 | 0.3 | 1.9 | 1-3.7 | 1.3 | 0.8-2.1 |
| | GA-1 | 1.0 | 6.4 | 2.8-15.1 | 3.7 | 1.6-8.5 |
| | GA-2.5 | 2.5 | 7.2 | 4.8-10.9 | 4.5 | 3.4-6 |
| | GA-5 | 5.0 | 10.1 | 6.5-15.9 | 4.9 | 3.2-7.6 |
| | GA-10 | 10 | 12.9 | 10.3-16 | 6.4 | 5-8.2 |
| | GA-20 | 20 | 13.0 | 8.4-20.2 | 7.0 | 4.7-10.6 |
| | DCCM1 | NA | 1.0 | 0.5-2.1 | 1.0 | 0.4-2.2 |
| | ConA | 2.5 | 102.6 | 78.6-133.7 | 67.2 | 49.3-91.6 |
| C8 | GA-0.3 | 0.3 | 4.7 | 2.9-7.8 | 2.8 | 1.7-4.6 |
| | GA-1 | 1.0 | 7.4 | 5.3-10.4 | 4.4 | 3.1-6.1 |
| | GA-2.5 | 2.5 | 11.9 | 9-15.7 | 6.4 | 4.9-8.3 |
| | GA-5 | 5.0 | 14.2 | 8.6-23.4 | 7.5 | 4.6-12.1 |
| | GA-10 | 10 | 12.5 | 9.3-16.8 | 7.1 | 5.6-8.9 |
| | GA-20 | 20 | 11.0 | 9.1-13.2 | 6.1 | 5.2-7.3 |
| | DCCM1 | NA | 1.0 | 0.5-1.9 | 1.0 | 0.5-2.1 |
| | ConA | 2.5 | 104.0 | 89.1-121.4 | 83.0 | 74.4-92.5 |
| M3 | GA-0.3 | 0.3 | 1.6 | 1.1-2.3 | 1.3 | 0.9-1.8 |
| | GA-1 | 1.0 | 4.1 | 2.9-5.8 | 3.0 | 2.3-4 |
| | GA-2.5 | 2.5 | 8.2 | 4.9-13.7 | 5.3 | 3.2-8.7 |
| | GA-5 | 5.0 | 8.0 | 5.5-11.7 | 4.8 | 3.5-6.5 |
| | GA-10 | 10 | 8.9 | 6.7-11.9 | 5.8 | 4.2-8.2 |
| | GA-20 | 20 | 8.0 | 5.8-11 | 5.1 | 3.7-7 |
| | DCCM1 | NA | 1.0 | 0.7-1.5 | 1.0 | 0.6-1.5 |
| | ConA | 2.5 | 78.8 | 53.4-116.3 | 70.9 | 48.1-104.3 |
| M4 | GA-0.3 | 0.3 | 1.8 | 0.9-3.8 | 1.2 | 0.6-2.4 |
| | GA-1 | 1.0 | 2.3 | 1.7-3.2 | 1.7 | 1.4-1.9 |
| | GA-2.5 | 2.5 | 6.6 | 4.4-9.8 | 4.0 | 2.6-6.3 |
| | GA-5 | 5.0 | 9.4 | 4.5-19.8 | 5.2 | 2.5-10.9 |

TABLE 69-continued

Expression of Mouse IL-17 from Primary LN Cells in
Response to GA Stimulation (Plate 3: C7-C8, M3-M4)

| GA | Stimulation | Conc. (μg/mL) | IL-17 mRNA/GAPDH | | IL-17 mRNA/B-Actin | |
|---|---|---|---|---|---|---|
| | | | Fold Change | Induction Range | Fold Change | Induction Range |
| | GA-10 | 10 | 3.1 | 1.2-7.6 | 1.7 | 0.7-4.2 |
| | GA-20 | 20 | 3.5 | 3-4.2 | 2.0 | 1.6-2.5 |
| | DCCM1 | NA | 1.0 | 0.7-1.4 | 1.0 | 0.7-1.4 |
| | ConA | 2.5 | 83.6 | 64.5-108.4 | 64.8 | 55.9-75.2 |

TABLE 70

Expression of Mouse CD25 from Primary LN Cells in Response
to GA Stimulation (Plate 1-2: C3, C6, M1, M2)

| GA | Stimulation | Conc. (μg/mL) | CD25 mRNA/GAPDH | | CD25 mRNA/B-Actin | |
|---|---|---|---|---|---|---|
| | | | Fold Change | Induction Range | Fold Change | Induction Range |
| C3 | GA-0.3 | 0.3 | 1.5 | 1.2-1.9 | 1.5 | 1.2-1.9 |
| | GA-1 | 1.0 | 2.1 | 1.5-3 | 2.2 | 1.5-3.1 |
| | GA-2.5 | 2.5 | 2.0 | 1.5-2.6 | 1.7 | 1.3-2.2 |
| | GA-5 | 5.0 | 2.0 | 1.4-2.9 | 1.8 | 1.3-2.4 |
| | GA-10 | 10 | 2.2 | 1.5-3.2 | 1.9 | 1.4-2.7 |
| | GA-20 | 20 | 2.0 | 1.6-2.5 | 1.7 | 1.5-2 |
| | DCCM1 | NA | 1.0 | 0.7-1.4 | 1.0 | 0.7-1.4 |
| | ConA | 2.5 | 3.6 | 3.1-4.3 | 4.1 | 3.5-4.7 |
| M1 | GA-0.3 | 0.3 | 1.7 | 1.3-2.2 | 1.5 | 1.1-2 |
| | GA-1 | 1.0 | 1.9 | 1.7-2.2 | 1.6 | 1.4-1.8 |
| | GA-2.5 | 2.5 | 2.3 | 1.6-3.2 | 1.7 | 1.2-2.5 |
| | GA-5 | 5.0 | 2.5 | 1.5-4 | 2.0 | 1.3-3 |
| | GA-10 | 10 | 2.4 | 1.5-3.8 | 2.1 | 1.1-3.9 |
| | GA-20 | 20 | 2.4 | 1.8-3.1 | 2.5 | 2.1-3 |
| | DCCM1 | NA | 1.0 | 0.7-1.4 | 1.0 | 0.7-1.4 |
| | ConA | 2.5 | 4.4 | 3.2-6 | 5.6 | 4.3-7.3 |
| C6 | GA-0.3 | 0.3 | 1.6 | 1.5-1.7 | 1.3 | 1.2-1.5 |
| | GA-1 | 1.0 | 1.9 | 1.1-3.1 | 1.5 | 1-2.3 |
| | GA-2.5 | 2.5 | 2.0 | 1.1-3.7 | 1.6 | 1-2.7 |
| | GA-5 | 5.0 | 2.2 | 2.1-2.3 | 1.7 | 1.7-1.8 |
| | GA-10 | 10 | 2.2 | 1.6-2.9 | 1.7 | 1.2-2.2 |
| | GA-20 | 20 | 2.0 | 1.7-2.3 | 1.6 | 1.4-1.7 |
| | DCCM1 | NA | 1.0 | 0.8-1.2 | 1.0 | 0.8-1.3 |
| | ConA | 2.5 | 4.5 | 2.9-6.9 | 4.7 | 3.2-6.9 |
| M2 | GA-0.3 | 0.3 | 1.6 | 1-2.5 | 1.3 | 0.8-2 |
| | GA-1 | 1.0 | 2.1 | 1.4-3 | 1.6 | 1.1-2.2 |
| | GA-2.5 | 2.5 | 3.1 | 1.6-5.9 | 2.6 | 1.3-5.2 |
| | GA-5 | 5.0 | 1.9 | 1.1-3.4 | 1.6 | 0.9-2.8 |
| | GA-10 | 10 | 2.5 | 1.6-3.7 | 2.1 | 1.5-2.9 |
| | GA-20 | 20 | 2.5 | 1.6-3.8 | 2.1 | 1.4-3.4 |
| | DCCM1 | NA | 1.0 | 0.8-1.3 | 1.0 | 0.9-1.2 |
| | ConA | 2.5 | 4.5 | 3.3-6.1 | 5.2 | 3.7-7.2 |

TABLE 71

Expression of Mouse CD25 from Primary LN Cells in
Response to GA Stimulation (Plate 3: C7-C8, M3-M4)

| GA | Stimulation | Conc. (μg/mL) | CD25 mRNA/GAPDH | | CD25 mRNA/B-Actin | |
|---|---|---|---|---|---|---|
| | | | Fold Change | Induction Range | Fold Change | Induction Range |
| C7 | GA-0.3 | 0.3 | 2.0 | 1.2-3.4 | 1.4 | 1-1.8 |
| | GA-1 | 1.0 | 3.1 | 2.5-3.9 | 1.8 | 1.7-1.9 |
| | GA-2.5 | 2.5 | 3.0 | 1.6-5.7 | 2.1 | 1.5-2.8 |
| | GA-5 | 5.0 | 3.9 | 2-7.7 | 2.1 | 1.2-3.9 |
| | GA-10 | 10 | 3.5 | 2.5-4.8 | 1.9 | 1.3-2.6 |
| | GA-20 | 20 | 3.7 | 3.1-4.4 | 2.3 | 1.9-2.9 |
| | DCCM1 | NA | 1.0 | 0.7-1.4 | 1.0 | 0.6-1.6 |
| | ConA | 2.5 | 5.6 | 3.6-8.6 | 5.0 | 3.3-7.5 |
| C8 | GA-0.3 | 0.3 | 2.3 | 1.4-4 | 1.6 | 1.1-2.5 |
| | GA-1 | 1.0 | 2.9 | 2.1-4.1 | 1.8 | 1.3-2.3 |
| | GA-2.5 | 2.5 | 3.4 | 2-5.8 | 1.9 | 1.1-3.1 |
| | GA-5 | 5.0 | 3.1 | 2.1-4.6 | 1.6 | 1.1-2.3 |
| | GA-10 | 10 | 3.2 | 2.5-3.9 | 1.8 | 1.5-2.1 |
| | GA-20 | 20 | 3.0 | 2-4.3 | 1.7 | 1.2-2.4 |
| | DCCM1 | NA | 1.0 | 0.8-1.3 | 1.0 | 0.8-1.2 |
| | ConA | 2.5 | 4.8 | 3.1-7.5 | 4.1 | 2.8-6 |
| M3 | GA-0.3 | 0.3 | 1.9 | 1.7-2.1 | 1.5 | 1.3-1.7 |
| | GA-1 | 1.0 | 2.4 | 1.8-3.3 | 1.9 | 1.5-2.5 |
| | GA-2.5 | 2.5 | 2.6 | 1.6-4.2 | 1.7 | 1.1-2.7 |
| | GA-5 | 5.0 | 2.7 | 1.7-4.4 | 1.7 | 1-2.7 |
| | GA-10 | 10 | 2.7 | 2.0-3.7 | 1.8 | 1.2-2.5 |
| | GA-20 | 20 | 2.8 | 1.5-5.4 | 1.8 | 1-3.5 |
| | DCCM1 | NA | 1.0 | 0.8-1.2 | 1.0 | 0.7-1.3 |
| | ConA | 2.5 | 4.6 | 3.6-5.9 | 5.1 | 4.4-6.1 |
| M4 | GA-0.3 | 0.3 | 1.9 | 1.2-3.1 | 1.4 | 0.9-2.1 |
| | GA-1 | 1.0 | 1.7 | 1.2-2.6 | 1.2 | 0.9-1.6 |
| | GA-2.5 | 2.5 | 1.9 | 1.1-3.3 | 1.2 | 0.6-2.1 |
| | GA-5 | 5.0 | 2.0 | 0.9-4.5 | 1.2 | 0.5-2.6 |
| | GA-10 | 10 | 1.9 | 1-3.6 | 1.1 | 0.6-2 |
| | GA-20 | 20 | 2.1 | 1.5-2.9 | 1.3 | 1-1.7 |
| | DCCM1 | NA | 1.0 | 0.9-1.1 | 1.0 | 0.9-1.1 |
| | ConA | 2.5 | 4.7 | 3.3-6.8 | 4.7 | 3.4-6.6 |

Conclusion

Levels of murine IL-2, IL-4, IL-5, IL-13, IL-17, and CD25 mRNA expression in lymph node (LN) cells isolated from GA-immunized mice were measured in GA-immunized mouse LN cells stimulated with GA in vitro. Twelve different GA lots were used for stimulation, including an altered manufacturing batch of GMA. Variations among expression levels of IL-2, IL-4, IL-5 and IL-13 mRNA in the samples stimulated with Copaxone® lots C1 to C8 were observed. The variations observed among Mylan lots M1, M2 and M3 were within the magnitude of the variations observed among the Copaxone® lots. LN cells stimulated with GMA lot M4 (altered lot GMA/R&D/026/11, made by withholding tyrosine for the first five minutes of synthesis) showed significantly lower levels of cytokine mRNA expression, and different induction patterns. IL-17 showed concentration-dependent induction in LN cells stimulated with four lots of Copaxone® and four lots of Mylan GA.

Example IX. Determination of the Potency of a
Test Lot of Glatiramer Acetate by Measuring a
Panel of Response Biomarker mRNAs in T-Cells
from GA-Immunized CSJLF1/JRj Mice Following
Challenge with Glatiramer Acetate As described in Example III, CSJLF1/JRj mice are each immunized with 250 μg of a reference standard lot of GA (Copaxone, Teva Pharmaceuticals USA, Inc.). On Day 10 post-immunization, lymph node cells are isolated from the animals and separate samples are stimulated with Myelin Basic Protein (MBP, a negative control), Concanavalin A (ConA, a positive control) a test lot of GA (GMA, Mylan Pharmaceuticals, Inc., at 0.5 μg/mL, 1 μg/mL, 2.5 μg/mL, 5 μg/mL, 10 μg/mL, and 15 μg/mL) and the reference standard lot of GA (at 0.5 μg/mL, 1 μg/mL, 2.5 μg/mL, 5 μg/mL, 10 μg/mL, and 15 μg/mL).

After 4 and 6 hours, the cells in each sample are lysed, total RNA isolated, cDNA synthesized and the amounts of GA response biomarker mRNAs IL-4, IL-5, IL-13, IL-17 are measured by Real Time PCR as described previously. The amount of each biomarker mRNA measured in the cells from GMA-immunized mice is compared to the amount measured in Copaxone-immunized mice to determine the relative potency.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A process for determining the relative potency of a test lot of glatiramer acetate (GA) and a reference standard lot of GA, the process comprising:
   a. culturing lymph node cells removed from a test animal immunized with a defined amount of the GA reference standard lot;
   b. incubating at least one sample containing a predetermined number of the cultured lymph node cells in the presence of a predetermined amount of the GA reference standard lot, and at least one sample containing a predetermined number of the cultured lymph node cells in the presence of a predetermined amount of the test lot of GA;
   c. measuring an amount of at least one GA response biomarker mRNA species in the lymph node cells incubated with the predetermined amount of the GA reference standard lot, and measuring the amount of the same at least one GA response biomarker mRNA species in the lymph node cells incubated with the predetermined amount of the test lot of GA, wherein the measuring of the at least one GA response biomarker mRNA species in the lymph node cells incubated with the predetermined amount of the GA reference standard lot, and the measuring of the at least one GA response biomarker mRNA species in the lymph node cells incubated with the predetermined amount of the test lot of GA, are carried out using the same measurement method, and;
   d. comparing the amount of the least one GA response biomarker mRNA species measured in the lymph node cells incubated with the predetermined amount of the test lot of GA with the amount of the same at least one GA response biomarker mRNA species measured in the lymph node cells incubated with the predetermined amount of the GA reference standard lot, wherein the comparing comprises dividing the amount of the at least one GA response biomarker mRNA species measured in the lymph node cells incubated with the predetermined amount of the test lot of GA by the amount of the least one GA response biomarker mRNA species measured in the lymph node cells incubated with the predetermined amount of the GA reference standard lot, to obtain the relative potency of the test lot of GA and the reference standard lot of GA.

2. The process of claim 1, wherein the test animal is a mouse.

3. The process of claim 1, wherein the at least one GA response biomarker mRNA species measured in the lymph node cells incubated with the GA reference lot and measured in the lymph node cells incubated with the GA test lot is transcribed from a gene encoding a cytokine, an activation marker or a cytokine receptor, or a chemokine.

4. The process of claim 3, wherein the at least one GA response biomarker mRNA species measured is:
   a) transcribed from a gene encoding a cytokine, wherein the cytokine is selected from the group consisting of: IL-2, IL-4, IL-5, IL-6, IL-10, IL-13, or IL-17, IL-18, IL-21, IL-22, IFN-γ, TNF-α (TNF), TNF-β (LT), TGF-β, and IL-1β;
   b) transcribed from a gene encoding an activation marker or a cytokine receptor, wherein the activation marker or a cytokine receptor is selected from the group consisting of: CD25, CD69, CD71, CD86, CD137, CD154, CD278, CD279, GATA3, Tbx21, HLA-DMA, HLA-DMB, IFN-γR2, IL-12RB1, IL-2RA, IL-2RG, IL-4R, IL-6R, IL-10RB, TGFBR2, FOXP3, and HLA-DR; or
   c) transcribed from a gene encoding a chemokine, wherein the chemokine is selected from the group consisting of: IL-8 (CXCL8), RANTES (CCL5), CCL1, CXCL4, and CXCL7.

5. The process of claim 4, wherein the at least one GA response biomarker mRNA species measured is transcribed from a gene encoding IL-2, IL-4, IL-5, IL-6, IL-10, IL-13, IL-17, IL-22, IFN-γ, TNF-α, CD25, or IL1-β.

6. The process of claim 5, wherein the at least one GA response biomarker mRNA species measured is transcribed from a gene encoding CD25, IL-4, or IL-13.

7. The process of claim 6, wherein at least two GA response biomarker mRNA species are measured, wherein each of the at least two measured GA response biomarker mRNA species is transcribed from a gene encoding CD25, IL-4, or IL-13.

8. The process of claim 1 further comprising determining whether the relative potency obtained is a desired relative potency.

9. The process of claim 8 wherein the desired relative potency is about 90% to about 125% of the potency of the GA reference standard lot.

10. The process of claim 9 wherein the desired relative potency is about 95% to about 125% of the potency of the GA reference standard lot.

11. The process of claim 1, wherein the at least one response biomarker mRNA is measured by Real-Time PCR.

12. The process of claim 1, wherein the at least one GA response biomarker mRNA species is measured at about 4 to about 6 hours after the incubation is initiated.

13. The process of claim 1, wherein a protein synthesis inhibitor is added to the incubation of the lymph node cells with the GA reference standard lot, and to the incubation of the lymph node cells with the test lot of GA.

14. The process of claim 1, wherein the reference standard lot is a batch of the released commercial GA product of Teva Pharmaceuticals USA, Inc.

15. A process for preparing a pharmaceutical composition containing GA, wherein during the process a test lot of GA is tested to determine whether it has a desired potency relative to the potency of the GA reference standard lot, the process comprising:
   determining the potency of the test lot of GA and comparing it to the potency of the reference standard lot, wherein the potencies of the test lot of GA and the reference standard lot are determined by measuring the amount of at least one GA response biomarker mRNA species produced in a cell of a culture of lymph node cells removed from a test mammal that has been immunized with a defined amount of a GA reference standard lot, wherein at least one sample containing a predetermined number of the cultured lymph node cells is incubated in the presence of a predetermined amount of the GA reference standard lot, wherein at least one sample containing a substantially identical predetermined number of the cultured lymph node cells is incubated in the presence of the same predetermined amount of the test lot of GA, wherein the measuring of the at least one GA response biomarker mRNA species produced in the lymph node cells incubated with the predetermined amount of the GA reference standard lot, and the measuring of the at least one GA response biomarker mRNA species produced in the lymph node cells incubated with the predetermined amount of the test lot of GA, are carried out using the same measurement method, wherein the comparing comprises dividing the amount of the at least one GA response biomarker mRNA species measured in the lymph node cells incubated with the predetermined amount of the test lot of GA by the amount of the least one GA response biomarker mRNA species measured in the lymph node cells incubated with the predetermined amount of the GA reference standard lot, to obtain the relative potency of the test lot of GA and the reference standard lot of GA; and admixing the test lot of GA into the pharmaceutical composition only if the test lot of GA is determined to have the desired potency relative to the potency of the reference standard lot.

16. The process of claim 15, wherein the test mammal is a mouse.

17. The process of claim 15, wherein the at least one GA response biomarker mRNA species measured in the lymph node cells incubated with the GA reference lot and measured in the lymph node cells incubated with the GA test lot is transcribed from a gene encoding a cytokine, an activation marker or a cytokine receptor, or a chemokine.

18. The process of claim 17, wherein the at least one GA response biomarker mRNA species measured is:
a) transcribed from a gene encoding a cytokine, wherein the cytokine is selected from the group consisting of: IL-2, IL-4, IL-5, IL-6, IL-10, IL-13, or IL-17, IL-18, IL-21, IL-22, IFN-γ, TNF-α (TNF), TNF-β (LT), TGF-β, and IL-1β;
b) transcribed from a gene encoding an activation marker or a cytokine receptor, wherein the activation marker or a cytokine receptor is selected from the group consisting of: CD25, CD69, CD71, CD86, CD137, CD154, CD278, CD279, GATA3, Tbx21, HLA-DMA, HLA-DMB, IFN-γR2, IL-12RB1, IL-2RA, IL-2RG, IL-4R, IL-6R, IL-10RB, TGFBR2, FOXP3, and HLA-DR; or
c) transcribed from a gene encoding a chemokine, wherein the chemokine is selected from the group consisting of: IL-8 (CXCL8), RANTES (CCL5), CCL1, CXCL4, and CXCL7.

19. The process of claim 18, wherein the at least one GA response biomarker mRNA species measured is transcribed from a gene encoding IL-2, IL-4, IL-5, IL-6, IL-10, IL-13, IL-17, IL-22, IFN-γ, TNF-α, CD25, or IL1-β.

20. The process of claim 19, wherein the at least one GA response biomarker mRNA species measured is transcribed from a gene encoding CD25, IL-4, or IL-13.

21. The process of claim 20, wherein at least two GA response biomarker mRNA species are measured, wherein each of the at least two measured GA response biomarker mRNA species is transcribed from a gene encoding CD25, IL-4, or IL-13.

22. The process of claim 15, wherein the desired relative potency is about 90% to about 125% of the potency of the GA reference standard lot.

23. The process of claim 22, wherein the desired relative potency is about 95% to about 125% of the potency of the GA reference standard lot.

24. The process of claim 15, wherein the at least one GA response biomarker mRNA is measured by Real-Time PCR.

25. The process of claim 15, wherein the response biomarker mRNA is measured at about 4 to about 6 hours after the incubation is initiated.

26. The process of claim 15, wherein a protein synthesis inhibitor is added to the incubation of the lymph node cells with the GA reference standard lot, and to the incubation of the lymph node cells with the test lot of GA.

27. The process of claim 15, wherein the reference standard lot is the released commercial GA product of Teva Pharmaceuticals USA, Inc.

28. A process for determining the potency and cross-potency of a test lot of GA relative to a GA reference standard lot, the process comprising:
a) immunizing a first test animal with a defined amount of the GA reference standard lot;
b) immunizing a second test animal with a defined amount of the GA test lot;
c) culturing lymph node cells removed from the immunized first test animal, and separately culturing lymph node cells removed from the immunized second test animal;
d) incubating at least one sample containing a predetermined number of the cultured lymph node cells from the immunized first test animal in the presence of a predetermined amount of the GA reference standard lot, and at least one sample containing a predetermined number of the cultured lymph node cells from the immunized first test animal in the presence of a predetermined amount of a test lot of GA;
e) incubating at least one sample containing a predetermined number of the cultured lymph node cells from the immunized second test animal in the presence of a predetermined amount of the GA reference standard lot, and at least one sample containing a predetermined number of the cultured lymph node cells from the immunized second test animal in the presence of a predetermined amount of a test lot of GA;
f) measuring the amount of (i) at least one GA response biomarker mRNA species in the lymph node cells from the immunized first test animal incubated with the predetermined amount of the GA reference standard lot, and (ii) the same at least one GA response biomarker mRNA species in the lymph node cells from the immunized first test animal incubated with the predetermined amount of the test lot of GA, wherein the measuring of the at least one GA response biomarker mRNA species in the lymph node cells from the immunized first test animal incubated with the predetermined amount of the GA reference standard lot, and the measuring of the at least one GA response biomarker mRNA species in the lymph node cells from the immunized first test animal incubated with the predetermined amount of the test lot of GA, are carried out using the same measurement method;
g) measuring the amount of (i) the at least one GA response biomarker mRNA species in the lymph node cells from the immunized second test animal incubated with the predetermined amount of the GA reference standard lot, and (ii) the at least one GA response biomarker mRNA species in the lymph node cells from the immunized second test animal incubated with the predetermined amount of the test lot of GA, wherein the measuring of the at least one GA response biomarker mRNA species in the lymph node cells from the immunized second test animal incubated with the predetermined amount of the GA reference standard lot, and the measuring of the at least one GA response biomarker mRNA species in the lymph node cells from the immunized second test animal incubated with the predetermined amount of the test lot of GA, are carried out using the same measurement method;

h) comparing the amount of the least one GA response biomarker mRNA species measured in the lymph node cells from the immunized first test animal incubated with the predetermined amount of the test lot of GA with the amount of the least one GA response biomarker mRNA species measured in the lymph node cells from the immunized first test animal incubated with the predetermined amount of the GA reference standard lot, thereby determining the relative potency of the test lot of GA and the GA reference standard lot, wherein the comparing comprises dividing the amount of the at least one GA response biomarker mRNA species measured in the lymph node cells from the immunized first test animal incubated with the predetermined amount of the test lot of GA by the amount of the least one GA response biomarker mRNA species measured in the lymph node cells from the immunized first test animal incubated with the predetermined amount of the GA reference standard lot, to obtain the relative potency of the test lot of GA and the reference standard lot of GA in cells from the immunized first test animal;

i) comparing the amount of the least one GA response biomarker mRNA species measured in the lymph node cells from the immunized second test animal incubated with the predetermined amount of the test lot of GA with the amount of the least one GA response biomarker mRNA species measured in the lymph node cells from the immunized second test animal incubated with the predetermined amount of the GA reference standard lot, thereby determining the relative potency of the reference standard lot of GA and the GA reference standard lot, wherein the comparing comprises dividing the amount of the at least one GA response biomarker mRNA species measured in the lymph node cells from the immunized second test animal incubated with the predetermined amount of the test lot of GA by the amount of the least one GA response biomarker mRNA species measured in the lymph node cells from the immunized second test animal incubated with the predetermined amount of the GA reference standard lot, to obtain the relative potency of the test lot of GA and the reference standard lot of GA in cells from the immunized second test animal;

j) comparing the amount of the least one GA response biomarker mRNA measured in the lymph node cells from the immunized first test animal incubated with the predetermined amount of the test lot of GA with the amount of the least one GA response biomarker mRNA measured in the lymph node cells from the immunized second test animal incubated with the predetermined amount of the GA test lot, wherein the comparing comprises dividing the amount of the at least one GA response biomarker mRNA species measured in the lymph node cells from the immunized first test animal incubated with the predetermined amount of the test lot of GA by the amount of the least one GA response biomarker mRNA species measured in the lymph node cells from the immunized second test animal incubated with the predetermined amount of the test lot of GA; thereby determining the cross-potency of the test lot of GA.

29. The process of claim 28, wherein the first test animal and the second test animal are mice selected from: mice of the same mouse strain: HLA-matched mice; littermates, and; twins.

30. The process of claim 29, wherein the at least one GA response biomarker mRNA species measured in steps (f)(i), (f)(ii), (g)(i), and (g)(ii), in the lymph node cells incubated with the GA reference lot and measured in the lymph node cells incubated with the GA test lot is transcribed from a gene encoding a cytokine, an activation marker or a cytokine receptor, or a chemokine.

31. The process of claim 30, wherein the at least one GA response biomarker mRNA species measured is:
   a) transcribed from a gene encoding a cytokine, wherein the cytokine is selected from the group consisting of: IL-2, IL-4, IL-5, IL-6, IL-10, IL-13, or IL-17, IL-18, IL-21, IL-22, IFN-γ, TNF-α (TNF), TNF-β (LT), TGF-β, and IL-1β;
   b) transcribed from a gene encoding an activation marker or a cytokine receptor, wherein the activation marker or a cytokine receptor is selected from the group consisting of: CD25, CD69, CD71, CD86, CD137, CD154, CD278, CD279, GATA3, Tbx21, HLA-DMA, HLA-DMB, IFN-γR2, IL-12RB1, IL-2RA, IL-2RG, IL-4R, IL-6R, IL-10RB, TGFBR2, FOXP3, and HLA-DR; or
   c) transcribed from a gene encoding a chemokine, wherein the chemokine is selected from the group consisting of: IL-8 (CXCL8), RANTES (CCL5), CCL1, CXCL4, and CXCL7.

32. The process of claim 31, wherein the at least one GA response biomarker mRNA species measured is transcribed from a gene encoding IL-2, IL-4, IL-5, IL-6, IL-10, IL-13, IL-17, IL-22, IFN-γ, TNF-α, CD25, or IL1-β.

33. The process of claim 32, wherein the at least one GA response biomarker mRNA species measured is transcribed from a gene encoding CD25, IL-4, or IL-13.

34. The process of claim 33, wherein at least two GA response biomarker mRNA species are measured, and wherein each of the at least two measured GA response biomarker mRNA species is transcribed from a gene encoding CD25, IL-4, or IL-13.

35. The process of claim 28 further comprising determining whether the test lot of GA has a desired relative potency, a desired cross-potency, or both.

36. The process of claim 35 wherein the desired relative potency, desired relative cross-potency, or both, of the test lot of GA is about 75% to about 125%.

37. The process of claim 36 wherein the desired relative potency, desired relative cross-potency, or both, is about 80% to about 120%.

38. The process of claim 28, wherein the at least one GA response biomarker mRNA species is measured by Real-Time PCR.

39. The process of claim 28, wherein the GA response biomarker mRNA species is measured at about 4 to about 6 hours after the incubation is initiated.

40. The process of claim 28, wherein a protein synthesis inhibitor is added to the incubation of the lymph node cells with the GA reference standard lot, and to the incubation of the lymph node cells with the test lot of GA.

41. The process of claim 28, wherein the reference standard lot is the released commercial GA product of Teva Pharmaceuticals USA, Inc.

42. A process for determining the relative potency of a second lot of GA to a first GA lot, the process comprising:
  immunizing a test animal with a defined amount of the first GA lot;
  culturing lymph node cells removed from the immunized test animal;
  incubating at least one sample containing a predetermined number of the cultured lymph node cells in the presence of a predetermined amount of the first GA lot, and at least one sample containing a predetermined number of the cultured lymph node cells in the presence of a predetermined amount of the second lot of GA;
  measuring the amount of at least one GA response biomarker mRNA in the lymph node cells incubated with the predetermined amount of the first GA lot, and the amount of the least one GA response biomarker mRNA in the lymph node cells incubated with the predetermined amount of the second lot of GA, wherein the measuring of the at least one GA response biomarker mRNA species in the lymph node cells incubated with the predetermined amount of the first GA lot, and the measuring of the at least one GA response biomarker mRNA species in the lymph node cells incubated with the predetermined amount of the second lot of GA, are carried out using the same measurement method, and;
  comparing the amount of the least one GA response biomarker mRNA measured in the lymph node cells incubated with the predetermined amount of the second lot of GA with the amount of the least one GA response biomarker mRNA measured in the lymph node cells incubated with the predetermined amount of the first GA lot, wherein the comparing comprises dividing the amount of the at least one GA response biomarker mRNA species measured in the lymph node cells incubated with the predetermined amount of the second lot of GA by the amount of the least one GA response biomarker mRNA species measured in the lymph node cells incubated with the predetermined amount of the first GA lot, to obtain the relative potency of the second lot of GA and the first GA lot;
thereby determining the relative potency of the second lot of GA to the first GA lot.

43. The process of claim 42 wherein the first GA lot is the released commercial GA product of Teva Pharmaceuticals USA, Inc., the second GA lot is the released commercial GA product of Teva Pharmaceuticals USA, Inc., or both.

44. The process of claim 1, wherein:
  step (b) comprises incubating each of at least three samples containing a predetermined number of the cultured lymph node cells in the presence of a predetermined amount of the GA reference standard lot, and each of at least three samples containing a predetermined number of the cultured lymph node cells in the presence of a predetermined amount of a test lot of GA;
  step (c) comprises measuring the amount of a different GA response biomarker mRNA species in each of the at least three samples of the cultured lymph node cells incubated with the predetermined amount of the GA reference standard lot, and the amount of the same GA response biomarker mRNA species in each of the at least three samples of the cultured lymph node cells incubated with the predetermined amount of the test lot of GA, wherein at least one of the GA response biomarker mRNA species is transcribed from a gene encoding a Th1-associated cytokine, at least one of the GA response biomarker mRNA species is transcribed from a gene encoding a Th2-associated cytokine, and at least one of the GA response biomarker mRNA species is transcribed from a gene encoding a Th17-associated cytokine, and;
  step d) comprises comparing the amount of each GA response biomarker mRNA species measured in the lymph node cells incubated with the predetermined amount of the test lot of GA with the amount of the same GA response biomarker mRNA species measured in the lymph node cells incubated with the predetermined amount of the GA reference standard lot.

45. The process of claim 44, wherein at least one of the GA response biomarker mRNA species is transcribed from a gene encoding a $T_{FH}$-associated cytokine.

46. The process of claim 45, wherein the $T_{FH}$-associated cytokine is IL-21.

47. The process of claim 44, wherein the Th1-associated cytokine is selected from: IFN-γ, IL-2, IL-1β, TNF-α, and CXCL1.

48. The process of claim 44, wherein the Th2-associated cytokine is selected from: IL-4, IL-5, IL-10, and IL-13.

49. The process of claim 44, wherein the Th17-associated cytokine is selected from: IL-17 and IL-22.

50. The process of claim 8, further comprising admixing the test lot of GA into a pharmaceutical composition if the test lot of GA is determined to have the desired potency relative to the potency of the reference standard lot.

* * * * *